(12) United States Patent
Nicolae et al.

(10) Patent No.: US 12,295,746 B2
(45) Date of Patent: May 13, 2025

(54) ADJUSTABLE STRAP FOR WEARABLE MONITOR

(71) Applicant: Whoop, Inc., Boston, MA (US)

(72) Inventors: Aurelian Nicolae, Brookline, MA (US); Benjamin August Rothenberg Peterson, Cambridge, MA (US); Anahis Kechejian, Boston, MA (US)

(73) Assignee: Whoop, Inc., Boston, MA (US)

( * ) Notice: Subject to any disclaimer, the term of this patent is extended or adjusted under 35 U.S.C. 154(b) by 631 days.

(21) Appl. No.: 17/508,468

(22) Filed: Oct. 22, 2021

(65) Prior Publication Data

US 2022/0117558 A1 Apr. 21, 2022

Related U.S. Application Data

(63) Continuation of application No. PCT/US2021/055325, filed on Oct. 16, 2021.

(Continued)

(51) Int. Cl.
*A61B 5/00* (2006.01)
*A44C 5/14* (2006.01)
(Continued)

(52) U.S. Cl.
CPC ............... *A61B 5/681* (2013.01); *A44C 5/14* (2013.01); *A44C 5/147* (2013.01); *A61B 5/0004* (2013.01); *A61B 5/0205* (2013.01); *A61B 5/6804* (2013.01); *A61B 5/6831* (2013.01); *A61B 5/02055* (2013.01); *A61B 5/02416* (2013.01); *A61B 2560/0214* (2013.01);

(Continued)

(58) Field of Classification Search
CPC ..... A61B 5/681; A61B 5/0205; A61B 5/6831; A61B 2560/0214; A44C 5/20; A44C 5/24; A44C 5/147; A44C 5/14; A44C 5/15; Y10T 24/4782; Y10T 24/4736; A44B 11/006
See application file for complete search history.

(56) References Cited

U.S. PATENT DOCUMENTS 1,467,465 A * 9/1923 Wiedmann ........... A44C 5/2085
63/3
8,190,229 B2 5/2012 Lowery et al.
(Continued)

FOREIGN PATENT DOCUMENTS

AU 359687 1/2015
AU 2015100951 A4 * 8/2015 ......... A44B 11/2596
(Continued)

OTHER PUBLICATIONS

Smith, "Whoop Strap 2.0 review", Jan. 18, 2017, Wareable (Year: 2017).*

(Continued)

*Primary Examiner* — Pamela M. Bays
*Assistant Examiner* — Christine Sison
(74) *Attorney, Agent, or Firm* — Strategic Patents, P.C.

(57) ABSTRACT

A strap for a wearable physiological monitor can be adjusted to a desired tension. The strap may include a buckle that retains a length of the strap as the strap is removed from and replaced to the wearable physiological monitor. In this manner, one or more straps may be removed and replaced without requiring readjustment of strap length for a particular user.

20 Claims, 21 Drawing Sheets

Related U.S. Application Data

(60) Provisional application No. 63/210,836, filed on Jun. 15, 2021, provisional application No. 63/137,993, filed on Jan. 15, 2021, provisional application No. 63/093,020, filed on Oct. 16, 2020.

(51) Int. Cl.
*A61B 5/0205* (2006.01)
*A61B 5/024* (2006.01)
*H02J 7/34* (2006.01)

(52) U.S. Cl.
CPC .......... *A61B 2562/0219* (2013.01); *A61B 2562/0271* (2013.01); *H02J 7/342* (2020.01); *Y10T 24/4736* (2015.01); *Y10T 24/4755* (2015.01); *Y10T 24/4782* (2015.01)

(56) References Cited

U.S. PATENT DOCUMENTS

| | | |
|---|---|---|
| D747,077 S | 1/2016 | Jayalath et al. |
| 9,498,128 B2 | 11/2016 | Jayalath et al. |
| D777,331 S | 1/2017 | Jayalath et al. |
| D779,167 S | 2/2017 | Morenstein et al. |
| D786,538 S | 5/2017 | Morenstein et al. |
| 9,913,611 B2 | 3/2018 | Wiebe et al. |
| 10,092,228 B2 | 10/2018 | Wiese et al. |
| 10,105,098 B2 | 10/2018 | Wiebe et al. |
| 10,143,405 B2 | 12/2018 | Jayalath et al. |
| D842,481 S | 3/2019 | Jayalath et al. |
| 10,264,982 B2 | 4/2019 | Ahmed et al. |
| 10,292,652 B2 | 5/2019 | Berg et al. |
| 10,321,832 B2 | 6/2019 | Berg et al. |
| 10,357,688 B2 | 7/2019 | Wiebe et al. |
| 10,362,993 B2 | 7/2019 | Wiebe et al. |
| 10,398,376 B2 | 9/2019 | Berg et al. |
| 10,413,219 B2 | 9/2019 | Jayalath et al. |
| 10,524,734 B2 | 1/2020 | Korzinov et al. |
| 10,617,354 B2 | 4/2020 | Berg et al. |
| 2008/0287770 A1 | 11/2008 | Kurzweil et al. |
| 2015/0359485 A1 | 12/2015 | Berg et al. |
| 2017/0055205 A1 | 2/2017 | Morris et al. |
| 2017/0079868 A1 | 3/2017 | Reid, Jr. et al. |
| 2017/0173391 A1 | 6/2017 | Wiebe et al. |
| 2017/0231566 A1 | 8/2017 | Klimek et al. |
| 2018/0049698 A1 | 2/2018 | Berg et al. |
| 2018/0140902 A1 | 5/2018 | Wiebe et al. |
| 2018/0279951 A1 | 10/2018 | Asnis et al. |
| 2018/0307314 A1 | 10/2018 | Connor |
| 2019/0046086 A1 | 2/2019 | Jayalath et al. |
| 2019/0046107 A1 | 2/2019 | Jang et al. |
| 2019/0046839 A1 | 2/2019 | Jang et al. |
| 2019/0076699 A1 | 3/2019 | Wiebe et al. |
| 2019/0116944 A1* | 4/2019 | Dickerson ............. G06F 1/1628 |
| 2019/0151713 A1 | 5/2019 | Berg et al. |
| 2019/0261874 A1 | 8/2019 | Berg et al. |
| 2019/0282856 A1 | 9/2019 | Wiebe et al. |
| 2019/0307404 A1 | 10/2019 | Wiebe et al. |
| 2019/0343459 A1 | 11/2019 | Korzinov et al. |
| 2019/0344121 A1 | 11/2019 | Wells et al. |
| 2020/0000378 A1 | 1/2020 | Jayalath et al. |
| 2020/0008746 A1 | 1/2020 | Berg et al. |
| 2020/0151595 A1 | 5/2020 | Jayalath et al. |

FOREIGN PATENT DOCUMENTS

| | | | |
|---|---|---|---|
| AU | 364377 | 9/2015 | |
| AU | 364708 | 10/2015 | |
| AU | 2015277767 | 1/2017 | |
| AU | 2015323905 | 4/2017 | |
| DE | 19620838 A1 * | 12/1996 | .......... A44C 5/2052 |
| EP | 3158569 | 4/2017 | |
| EP | 3200635 | 8/2017 | |
| WO | WO-2015195209 | 12/2015 | |
| WO | WO-2016054057 | 4/2016 | |
| WO | WO-2016057823 | 4/2016 | |
| WO | WO-2017048580 | 3/2017 | |
| WO | WO-2017106781 | 6/2017 | |
| WO | WO-2019036389 | 2/2019 | |
| WO | WO-2019213114 | 11/2019 | |
| WO | WO-2022082077 | 4/2022 | |

OTHER PUBLICATIONS

Chin, "WHOOP revolutionizes way elite athletes, like lebron james, reduce injury + predict peak performance", Aug. 17, 2016, designboom (Year: 2016).*

WIPO, "PCT Application No. PCT/US21/55325 International Preliminary Report on Patentability mailed Apr. 27, 2023", 12 pages.

ISA/US, "PCT Application No. PCT/US21/55325 International Search Report and Written Opinion mailed Mar. 3, 2022", 16 pages.

EPO, "EP Application No. 21881247.7 Extended Search Report mailed Sep. 9, 2024", 7 pages.

* cited by examiner

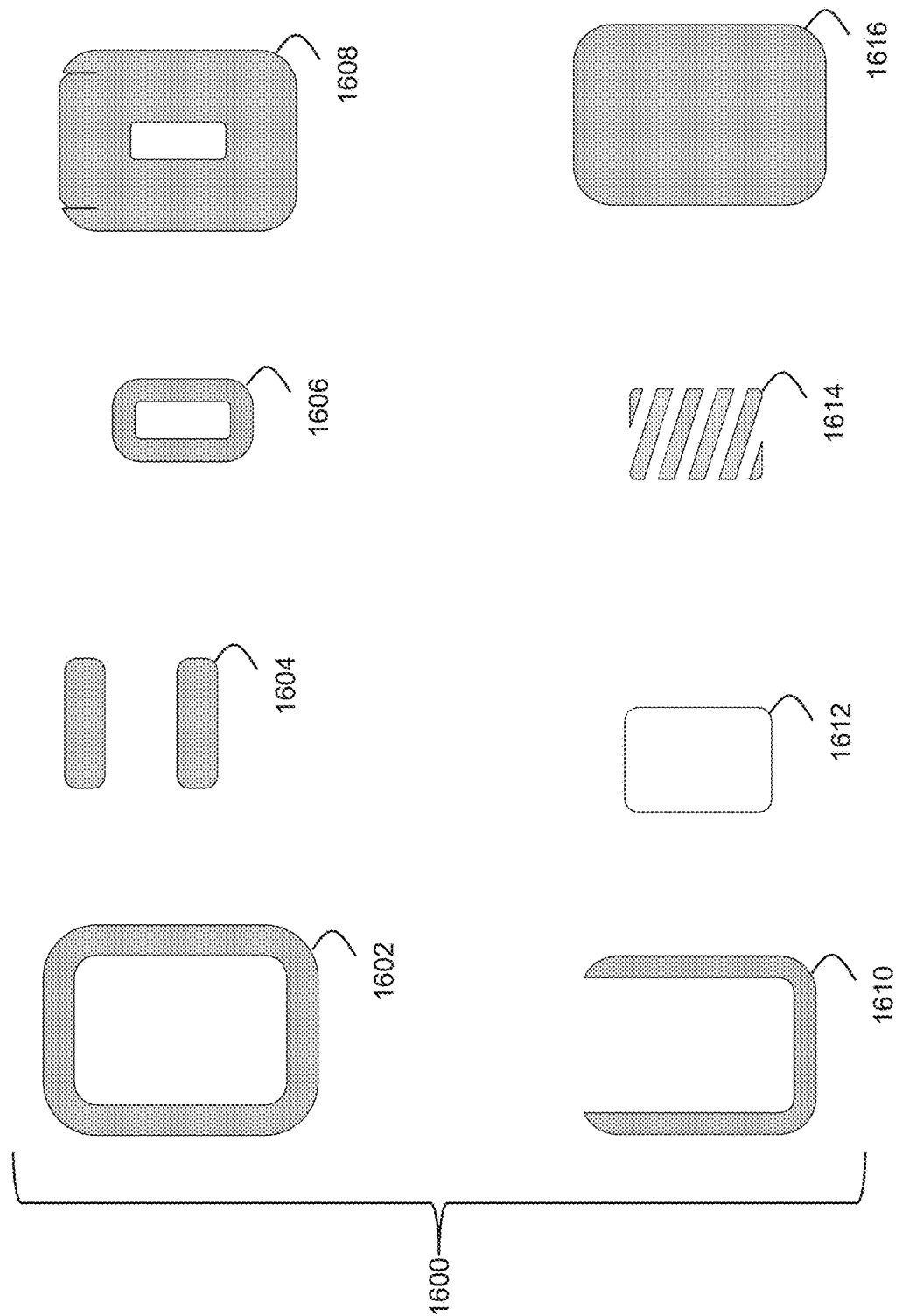

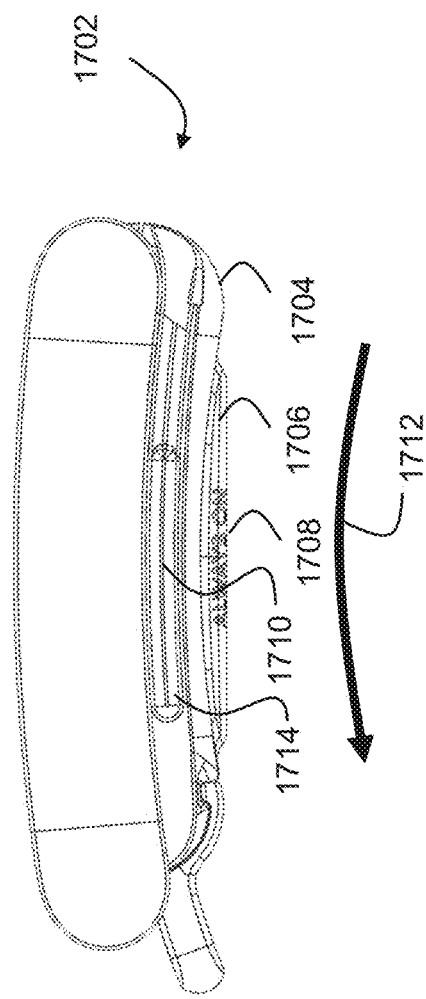
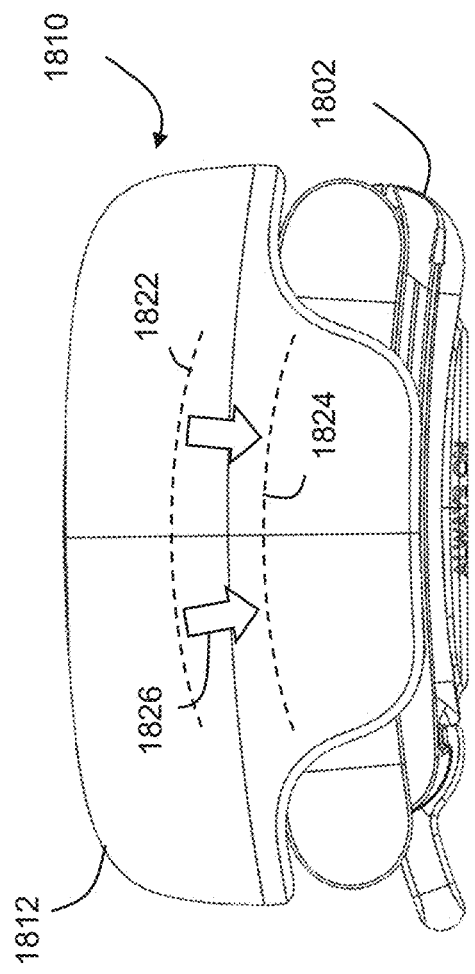

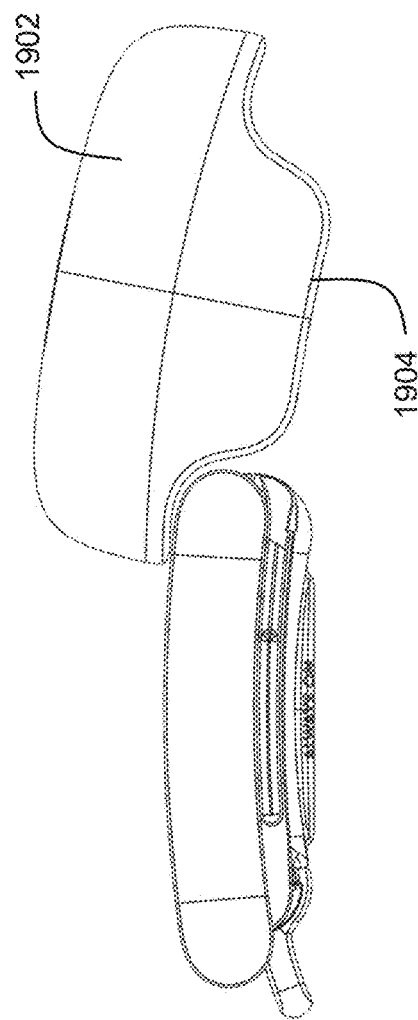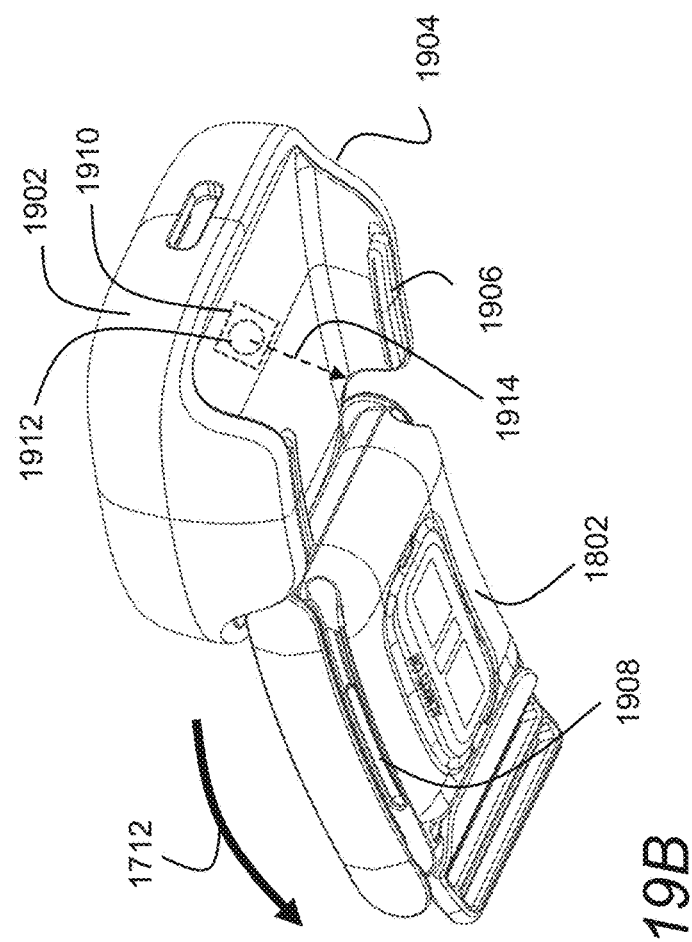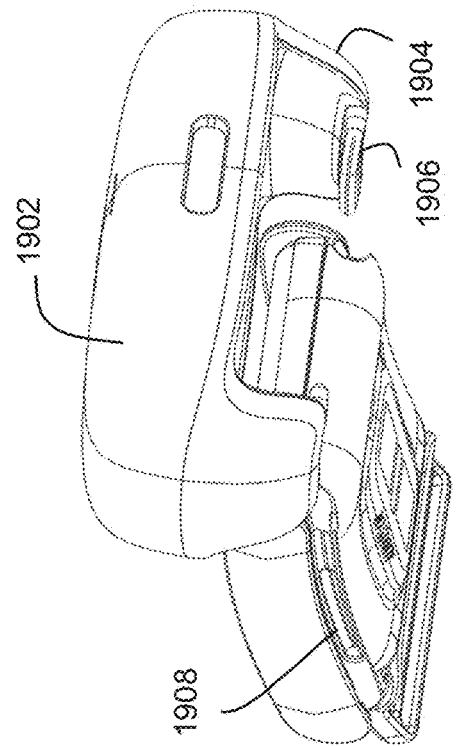
Fig. 19A
Fig. 19B

ADJUSTABLE STRAP FOR WEARABLE MONITOR

CROSS-REFERENCE TO RELATED APPLICATIONS

This application is a bypass continuation that claims priority to International Patent Application No. PCT/US21/55325 filed on Oct. 16, 2021, which claims priority to U.S. Provisional Patent App. No. 63/093,020 filed on Oct. 16, 2020, U.S. Provisional Patent App. No. 63/137,993 filed on Jan. 15, 2021, and U.S. Provisional Patent No. 63/210,836 filed on Jun. 15, 2021. The entire content of each of the foregoing applications is hereby incorporated by reference.

TECHNICAL FIELD

The present disclosure generally relates to physiological monitoring systems and arrangements for deploying and using same.

BACKGROUND

Wearable physiological monitors can provide a wealth of physiological data from a wearer. There remains a need for improved physiological monitors to better support and augment continuous monitoring for a wide range of users and activities.

SUMMARY

The present teachings include physiological monitoring systems and arrangements for deploying and using same, including devices, systems, and methods to support continuous monitoring. For example, the present disclosure includes a garment that provides infrastructure for using one or more physiological monitoring devices. To this end, the present disclosure also includes a pocket for a removable and replaceable physiological monitoring device that can be incorporated into an article of clothing and configured to retain the device in a position for monitoring during physical activity. Moreover, the present disclosure includes a wireless battery that can be removably and replaceably coupled to a physiological monitoring device in a manner that securely retains the wireless recharging battery in a precise location relative to a corresponding wireless power interface of the monitoring device. The present disclosure further includes a strap for a wearable physiological monitor that can be adjusted to a desired tension.

A garment provides infrastructure for using one or more physiological monitoring devices. This may include connecting infrastructure such as physical restrains to securely retain monitoring devices during use, supporting infrastructure such as an intra-garment communications bus, external communications infrastructure, power sources, and the like, as well as augmentation infrastructure to augment monitors with, e.g., processing power, geolocation services, user interfaces, additional sensors, and so forth.

In an aspect, a system disclosed herein may include: a module including one or more sensors for physiological monitoring; a garment having a pocket shaped and sized to removably and replaceably receive the module, the pocket positioned to retain the module at a location on a wearer of the garment and the pocket configured to retain the module with a predetermined contact force against a skin of the wearer; and an infrastructure component coupled to the garment for using the module in a physiological monitoring system.

Implementations may include one or more of the following features. The module may include a fixture for attaching to an adjustable wrist strap configured to secure the module as a wrist-worn physiological monitor. The module may detect the location and adapt a data acquisition algorithm applied to data from one or more sensors based on the location. The pocket may include a window facilitating direct physical contact between a sensing region of the module and the wearer. The pocket may be positioned within an elastic band of the garment. The pocket may be positioned over an artery of the wearer suitable for acquiring photoplethysmography data. The garment may include a plurality of pockets for retaining a plurality of modules. The system may further include two or more modules in the plurality of pockets, each of the two or more modules configured to monitor a different physiological parameter. One or more of the sensors may include at least one of an optical sensor, a light emitting diode, an accelerometer, a gyroscope, a conductivity sensor, a capacitive sensor, a skin temperature sensor, and an environmental sensor. The infrastructure component may include a location identifier for the pocket. The infrastructure component may include a power supply for the module. The infrastructure component may include a communication system. The infrastructure component may include a wired intra-garment network. The infrastructure component may include a processor. The infrastructure component may include a Global Positioning System. The infrastructure component may include a timing device for synchronizing signals from two or more modules. The infrastructure component may include a beacon for synchronizing signals among two or more modular sensing devices. The physiological monitoring system may monitor one or more of a heart rate, a body temperature, a muscle activity, and a respiration rate. The system may further include a remote processing resource coupled in a communicating relationship with the module in the garment. The remote processing resource may be configured to receive data from the module including the location of the module and physiological data from one or more sensors, and the remote processing resource may be further configured to adapt processing of the physiological data based on the location. The system may further include a plurality of garments each providing data from at least one garment-coupled module. The system may further include a processor coupled in a communicating relationship with the module and configured to detect the location of the module and adapt processing of data from one or more sensors according to the location. The system may further include a processor coupled in a communicating relationship with the module and configured to detect the location of the module and select a motion-based activity recognition model based on the location. The system may further include a processor coupled in a communicating relationship with the module and configured to perform a differential analysis based on signals from two or more modules. The system may further include a processor configured to detect when the garment does not properly fit the wearer for acquisition of physiological data from the wearer. The module may have at least two sensors for detecting contact with the wearer including a first sensor for detecting contact when the module is in the pocket and a second sensor for detecting contact when the module is worn on a wrist of the wearer. The system may further include two or more modules at two or more locations on the garment, the physiological monitoring system configured to detect the two or more locations and obtain synchronous measurements from the two or more modules at the two or more locations. The system may further include two or more modules at two or more locations on the garment, the physiological monitoring system configured to detect the two or more locations and obtain concurrent measurements from the two or more modules at the two or more locations.

In an aspect, a smart garment system disclosed herein may include: a garment structurally configured for wearing by a user, the garment including one or more designated areas for sensing a physiological parameter of the user; a plurality of modules sized and shaped for placement at one or more designated areas of the garment, each of the plurality of modules including one or more physiological sensors and a communications interface configured to transmit data from the one or more physiological sensors; and a controller configured to determine a location of a first module of the plurality of modules proximal to one of the designated areas of the garment, and based on the location, control operation of the first module.

Implementations may include one or more of the following features. The controller may be configured to control one or more of (i) sensing performed by one or more physiological sensors of the first module and (ii) processing by the first module of the data received from one or more physiological sensors. The system may further include a processor and a memory, the memory bearing computer executable code configured to be executed by the processor to perform processing of the data received from the first module. The memory may store one or more algorithms to transform data received from the first module. An algorithm of the one or more algorithms may be selected based on the location of the first module. An algorithm of the one or more algorithms may be selected at least in part based on metadata received from one of the first module and the garment. The metadata may include at least one of a sex of the user, a weight of the user, a height of the user, an age of the user, and data associated with the garment. The metadata may include data associated with the garment including at least one of a type of garment, a size of the garment, a gender configuration of the garment, a manufacturer, a model number, a serial number, a material, and fit information. The garment may include garment metadata transmittable to one or more of the plurality of modules and the controller. The processor may be configured to assess quality of the data received from the first module. The processor may be configured to provide, based on the quality of the data, a recommendation regarding at least one of the location of the first module and the garment. The processor may be configured to provide a recommendation regarding a different garment. One or more of the processor and the memory may be included on at least one of the plurality of modules. One or more of the processor and the memory may be remote relative to each of the plurality of modules. Data received from the first module may include at least one of heart rate data, muscle oxygen saturation data, temperature data, and movement data. The controller may be included on at least one of the plurality of modules. The controller may be remote relative to each of the plurality of modules. The system may further include selecting a processing algorithm based on the location of the first module. Determining the location of the first module may include receiving a sensed location for the first module. The sensed location may be provided by one or more of a near-field-communication (NFC) tag, a capacitance sensor, a magnetic sensor, an electrical contact, and a mechanical contact. The sensed location may be provided by an NFC tag disposed on or within the garment for communication with the first module. Determining the location of the first module may be at least in part based on interpretation of data received from the first module. Determining the location of the first module may include receiving input from the user. The location of the first module may be transmitted for storage and analysis to a remote processing facility. The system may further include reconciling one or more sources of location of information. A designated area of the one or more designated areas may include a pocket structurally configured to receive a module therein. A designated area of the one or more designated areas may include a first fastener configured to cooperate with a second fastener disposed on a module. One or more of the first fastener and the second fastener may include at least one of a hook-and-loop fastener, a button, a clamp, a clip, a snap, a magnet, a projection, and a void. The one or more designated areas may include at least one of a torso region, a spinal region, an extremity region, a waistband region, a head region, and a cuff region. The one or more designated areas may include at least a region adjacent to one or more muscle groups of the user. The one or more muscle groups may include at least one of the pectoralis major, latissimus dorsi, and biceps brachii. The garment may be an undergarment. One or more of the plurality of modules may be removable and replaceable relative to the garment. One or more of the plurality of modules may be configured to sense data using one or more physiological sensors in a plurality of one or more designated areas of the garment.

A pocket for a removable and replaceable physiological monitoring device can be incorporated into an article of clothing and configured to retain the device in a position for monitoring during physical activity, while facilitating removal and replacement of the device as needed.

In an aspect, a system disclosed herein may include: a monitoring device having a top surface with a sensor for contact with a target surface, a bottom surface opposing the top surface, and sides forming a perimeter of the monitoring device; an article of clothing; and a pocket securing the monitoring device in the article of clothing. The pocket may include: a retaining ring formed of a first material, the retaining ring shaped to surround the perimeter of the monitoring device and raised above a surface of the article of clothing to inhibit lateral movement of the bottom surface of the monitoring device along the surface of the article of clothing when the monitoring device is placed for use in the pocket; a window formed of a second material, the window sized and positioned along an interior region of the article of clothing to expose the sensor to the target surface when the monitoring device is placed for use in the pocket; and a wall formed of a third material, the wall coupling the retaining ring to the window, the third material being an elastic sheet material having a higher elasticity than the window.

Implementations may include one or more of the following features. The system may further include a high-friction surface on an interior surface of the pocket bounded by the retaining ring, the high-friction surface selected to inhibit lateral movement of the monitoring device along the interior surface of the pocket when the monitoring device is placed for use within the pocket. The system may further include an access port along an edge of the pocket, the access port sized to receive the monitoring device and the access port including a seal configured to apply a force on the monitoring device inducing elastic deformation of the wall of the pocket. The seal may include a hook-and-loop fastener along the access port. The pocket may include an interior surface bounded by the retaining ring and separated from the window by the wall of the third material, where the interior surface is formed of a fourth material having a lower elasticity than the third material, where, when the access port is closed, the wall yields elastically about the perimeter of the monitoring device to urge the monitoring device away from the interior surface of the pocket and toward the target surface for the sensor. The access port may be accessible through a first surface on an interior of the article of clothing contacting a wearer when the article of clothing is in use. The access port may be accessible through a second surface on an exterior of the article of clothing facing away from a wearer when the article of clothing is in use. The window may be smaller than a projection of the monitoring device through a plane of the window when the monitoring device is placed for use. The window may be formed of sheet material that is substantially inelastic, relative to the fourth material of an interior surface of the pocket, within the plane of the window. The article of clothing may include an athletic undergarment. The article of clothing may include one or more of a bicep band, a sock, a calf band, and a chest band.

In an aspect, a pocket for securing a modular physiological monitoring device within an article of clothing disclosed herein may include: a first surface providing a substrate for a monitoring device when inserted into the pocket, the first surface formed of a first sheet material having a first elasticity; a retaining ring formed of a second material, the retaining ring forming a raised perimeter to inhibit movement of a device in the pocket along the first surface; a wall formed of a third material having a higher elasticity than the first sheet material, the wall including an opening positioned to expose a sensor of a device when placed for use in the pocket, and the third material selected to elastically yield to the device when inserted into the pocket; a window formed of a fourth material positioned around the opening, the fourth material having a lower elasticity than the third material of the wall; and an access port configured to receive the device into the pocket when opened, and configured to secure the device within the pocket against an elastic force of the wall when closed.

Implementations may include one or more of the following features. The first sheet material may include a high friction surface facing an interior of the pocket, the high friction surface having a greater coefficient of sliding friction than other interior surfaces of the pocket in order to inhibit lateral movement of a device within the pocket along the first surface. The pocket may further include a high friction surface treatment for the first sheet material on the first surface, the high friction surface treatment having a greater coefficient of sliding friction than other interior surfaces of the pocket in order to inhibit lateral movement of a device within the pocket along the first surface. The retaining ring may be formed of neoprene. The retaining ring may have a thickness of between about 0.5 and about 1.5 millimeters. The third material of the wall may include a nylon blend woven material. The first sheet material may include neoprene. The window may be sized smaller than a projection of the device normal to a plane of the window when the device is placed for use in the pocket. The access port may include a seal, the seal including one or more of a zipper, a snap, and a hook-and-loop fastener.

A wireless recharging battery can be removably and replaceably coupled to a physiological monitoring device in a manner that securely retains the wireless recharging battery in a precise location relative to a corresponding wireless power interface of the monitoring device, while facilitating intuitive and easy removal and replacement of the wireless recharging battery by a user.

In an aspect, a device disclosed herein may include: a monitoring device including a first housing, where the first housing includes a first waterproof enclosure for a first battery and sensing circuitry powered by the first battery, the first housing including a pair of functional guide surfaces on opposing sides thereof, each of the functional guide surfaces forming a curved draw path, and each of the functional guide surfaces including a curved detent; and a recharging battery including a second housing, where the second housing includes a second waterproof enclosure for a second battery and wireless power transfer circuitry, the rechargeable battery including a pair of wings each having a curved flange shaped to guide the rechargeable battery along the curved draw path by following a respective one of the functional guide surfaces, the curved flange further shaped to mate with the curved detent of the monitoring device to secure the recharging battery in a predetermined position relative to the monitoring device for wirelessly transferring power from the second battery to the first battery through the wireless power transfer circuitry.

Implementations may include one or more of the following features. The functional guide surfaces may create maximum insertion force for coupling the recharging battery to the monitoring device along the curved draw path of about 8 Newtons. The functional guide surfaces may create maximum insertion force for coupling the recharging battery to the monitoring device along the curved draw path of about 5 Newtons to about 15 Newtons. The functional guide surfaces may create a maximum removal force for uncoupling the recharging battery from the monitoring device along the curved draw path of about 18 Newtons. The functional guide surfaces may create a maximum removal force for uncoupling the recharging battery from the monitoring device along the curved draw path of about 10 Newtons to about 35 Newtons. Each of the functional guide surfaces may include a ramp progressively displacing a corresponding one of the wings to receive the recharging battery along the curved draw path. The ramp of each of the functional guide surfaces may displace one of the wings of the recharging battery about 0.5 millimeters in a direction away from the monitoring device. Each of the functional guide surfaces may include a second ramp progressively displacing the corresponding one of the wings to release the recharging battery from the curved detent when removing the recharging battery along the curved draw path. Each of the functional guide surfaces may include a hard stop preventing movement of the recharging battery beyond the curved detents that receive the curved flanges when attaching the recharging battery to the monitoring device along the curved draw path. Each of the curved flanges of the wings yield apart from one another about 0.5 millimeters in response to an outward force of about 20 Newtons. Each of the curved flanges require at least 100 Newtons of outward force to separate from the functional guide surfaces of the monitoring device in a direction off the curved draw path. The second waterproof enclosure may prevent ingress of water in harmful quantities during immersion in water to at least one meter for at least thirty minutes. The first waterproof enclosure may prevent ingress of water in harmful quantities during immersion in water to at least one meter for at least thirty minutes. The curved draw path may have a radius of curvature of about 227 millimeters. The curved draw path may have a radius of curvature of between about 200 millimeters and about 260 millimeters. The second housing may be formed of a polycarbonate blend. The pair of wings may be symmetrical about an axis normal to the draw path to facilitate bidirectional coupling of the recharging battery to the monitoring device. The recharging battery may be configured for bidirectional mechanical and electromagnetic coupling to the monitoring device.

In an aspect, a device disclosed herein may include: a battery; a wireless power transfer circuit including an antenna having a normal axis; a housing enclosing the battery and the wireless power transfer circuit, where the housing encloses the battery and the wireless power transfer circuit to prevent ingress of water in harmful quantities during immersion in water to at least one meter for at least thirty minutes; and two wings extending from the housing parallel to the normal axis of the antenna, each wing having a curved flange extending toward an opposing one of the two wings, where each of the wings yields about 0.5 millimeters to an outward force of between about ten and about thirty Newtons, and where each of the curved flanges has a radius of curvature of between about two hundred and about two hundred fifty millimeters.

Implementations may include one or more of the following features. The two wings may be formed of a polycarbonate blend. The antenna may be a planar antenna shaped and sized for non-contact power transfer. The antenna may conform to a lateral surface of a right cylinder. The lateral surface may have a curvature corresponding to the radius of curvature of the curved flanges. The device may further include a physiological monitoring device having a second antenna for non-contact power transfer, the second antenna having a curvature corresponding to the radius of curvature of the curved flanges.

A strap for a wearable physiological monitor can be adjusted to a desired tension. The strap may include a buckle that retains a length of the strap as the strap is removed from and replaced to the wearable physiological monitor. In this manner, one or more straps may be removed and replaced without requiring readjustment of strap length for a particular user.

In an aspect, a physiological monitoring system disclosed herein may include: a monitoring device including a housing for a battery and sensing circuitry powered by the battery; a clasp pivotally mounted to a first end of the monitoring device on a first end of the clasp at a rotation axis, a second end of the clasp rotatable between a first position adjacent to a second end of the monitoring device and a second position away from the second end of the monitoring device, the clasp including a cross member on the second end of the clasp having an axis aligned to the rotation axis for the clasp; a band of an elastic material, the band having a first end and a second end; a hook rotatably coupled to the cross member on the second end of the clasp, and rotatable around the rotation axis to decouple the hook from the cross member; and a buckle, the buckle linearly removable from and replaceable to the second end of the monitoring device along a second axis parallel to the rotation axis for the clasp, the buckle including a fixture providing an overlapping path for adjustably retaining a length of the band of the elastic material between the hook and the buckle.

Implementations may include one or more of the following features. The housing may enclose the battery and sensing circuitry in a waterproof enclosure that prevents ingress of water in harmful quantities during immersion in water to at least one meter for at least thirty minutes. The band of the elastic material may include an elastic woven material. The band of the elastic material may include a high friction material on a surface contacting the monitoring device when the clasp is in the first position. The monitoring device may include a spring bar with protruding surfaces to retain the clasp in the first position. The clasp may include a pair of arms extending from the first end of the clasp to the second end of the clasp, the pair of arms securing the buckle against displacement along the second axis when the clasp is in the first position. The pair of arms may rotate away from the second end of the monitoring device when in the second position to permit linear movement of the buckle along the second axis to decouple the buckle from the monitoring device. A circumferential tension along the band of the elastic material may secure the hook in a rotational orientation that prevents decoupling of the hook from the cross member of the clasp when the clasp is in the first position. The buckle may have a c-shaped cross section along the second axis shaped and sized to couple to a partially cylindrical surface on the second end of the monitoring device. The c-shaped cross section may include a tooth shaped and sized to engage an indent in the second end of the monitoring device when the buckle is aligned for use along the second axis.

In an aspect, an adjustable band disclosed herein may include: a band of an elastic material, the band having a first end and a second end; a hook affixed to the first end of the band; and a buckle coupled to the second end of the band, the buckle having a pair of arms forming a c-shaped cross section along an axis transverse to the band, each of the arms having a flange for engaging the buckle with a device under a circumferential tension on the band, the buckle including a fixture providing an overlapping path for adjustably securing the band in the buckle to retain a length of the band of the elastic material between the hook and the buckle under the circumferential tension on the band.

Implementations may include one or more of the following features. The adjustable band may further include a clasp pivotally mounted to an end of the device on a first end of the clasp at a rotation axis, a second end of the clasp rotatable between a first position and a second position. The band of the elastic material may include a high friction material on a surface contacting the device when the clasp is in the first position. The device may include a spring bar with protruding surfaces to retain the clasp in the first position. A circumferential tension along the band of the elastic material may secure the hook in a rotational orientation that prevents decoupling of the hook from a cross member of the clasp when the clasp is in the first position. The band of the elastic material may include an elastic woven material. The hook may include a crimp permitting the hook to fold with a low profile and lie flush with the band. The fixture may include two adjacent slits along the overlapping path. The pair of arms may overlap ends of the buckle when in a closed position. The pair of arms may generally rotate away from an end of the device when in an open position.

BRIEF DESCRIPTION OF THE DRAWINGS

The foregoing and other objects, features, and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein. In the drawings, like reference numerals generally identify corresponding elements.

FIG. 16 illustrates a layer-based fabrication process for a pocket.

FIG. 17 illustrates a physiological monitoring device.

FIG. 18 illustrates a wireless battery coupled to a physiological monitoring device.

FIG. 19A illustrates a recharging battery aligned for coupling to a monitoring device.

FIG. 19B illustrates wings extending from the recharging battery for coupling the recharging battery to a monitoring device.

DESCRIPTION

Figure 1:
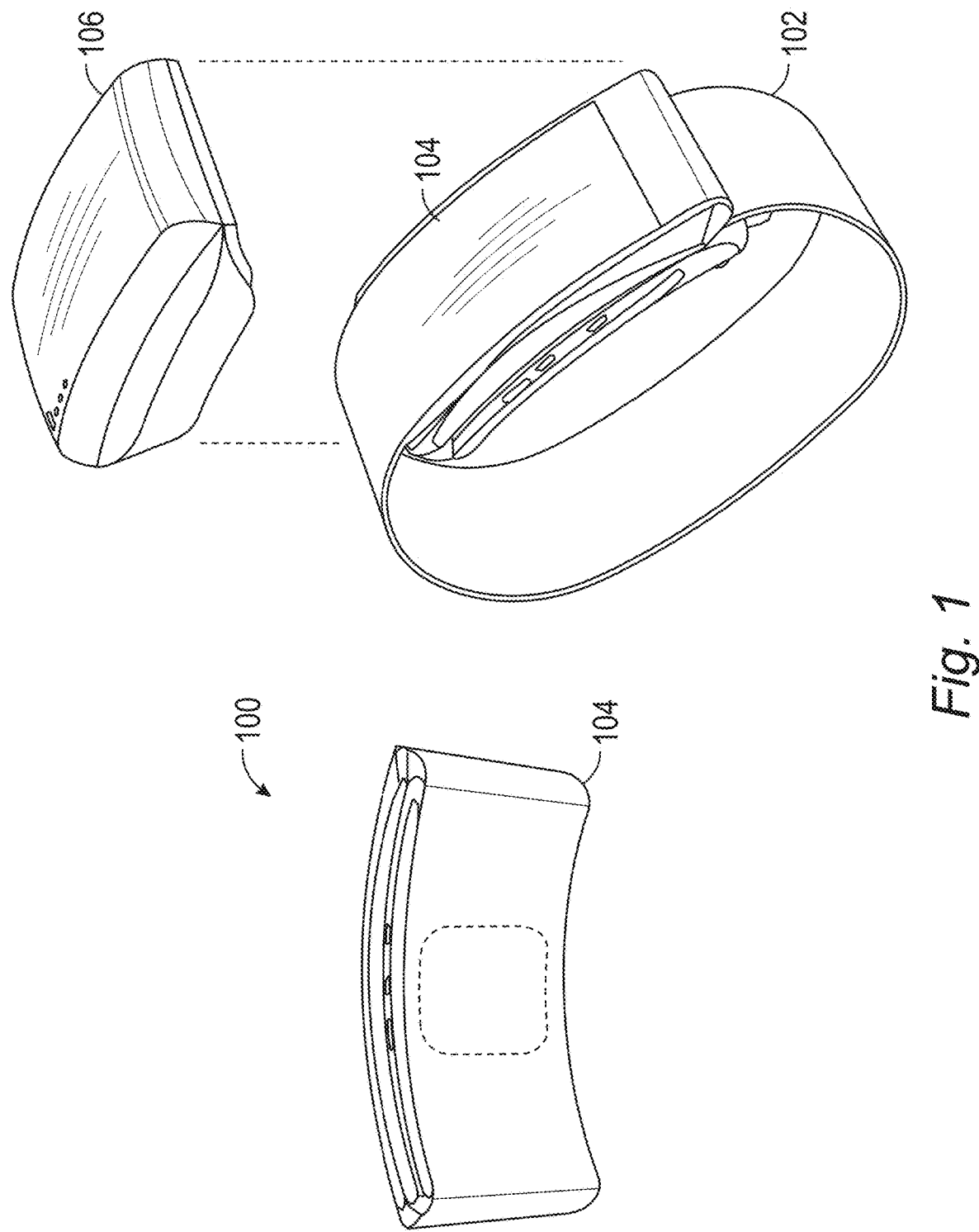
FIG. 1 illustrates front and back perspective views of a wearable system configured as a bracelet including one or more straps.

The embodiments will now be described more fully hereinafter with reference to the accompanying figures, in which preferred embodiments are shown. The foregoing may, however, be embodied in many different forms and should not be construed as limited to the illustrated embodiments set forth herein. Rather, these illustrated embodiments are provided so that this disclosure will convey the scope to those skilled in the art.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately" or the like, when accompanying a numerical value, are to be construed as indicating a deviation as would be appreciated by one of ordinary skill in the art to operate satisfactorily for an intended purpose. Similarly, words of approximation such as "approximately" or "substantially" when used in reference to physical characteristics, should be understood to contemplate a range of deviations that would be appreciated by one of ordinary skill in the art to operate satisfactorily for a corresponding use, function, purpose, or the like. Ranges of values and/or numeric values are provided herein as examples only, and do not constitute a limitation on the scope of the described embodiments. Where ranges of values are provided, they are also intended to include each value within the range as if set forth individually, unless expressly stated to the contrary. The use of any and all examples, or exemplary language ("e.g.," "such as," or the like) provided herein, is intended merely to better describe the embodiments and does not pose a limitation on the scope of the embodiments. No language in the specification should be construed as indicating any unclaimed element as essential to the practice of the embodiments.

In the following description, it is understood that terms such as "first," "second," "top," "bottom," "up," "down," "above," "below," and the like, are words of convenience and are not to be construed as limiting terms unless specifically stated to the contrary.

The term "user" as used herein, refers to any type of animal, human or non-human, whose physiological information may be monitored using an exemplary wearable physiological monitoring system.

The term "continuous," as used herein in connection with heart rate data collection, refers to collection of heart rate data at a sufficient frequency to enable detection of every heartbeat and also refers to collection of heart rate data continuously throughout the day and night.

The term "computer-readable medium," as used herein, refers to a non-transitory storage hardware, non-transitory storage device or non-transitory computer system memory that may be accessed by a controller, a microcontroller, a microprocessor, a computational system, or a module of a computational system to encode thereon computer-executable instructions or software programs. The "computer-readable medium" may be accessed by a computational system or a module of a computational system to retrieve and/or execute the computer-executable instructions or software programs encoded on the medium. The non-transitory computer-readable media may include, but are not limited to, one or more types of hardware memory, non-transitory tangible media (for example, one or more magnetic storage disks, one or more optical disks, one or more USB flash drives), computer system memory or random access memory (such as, DRAM, SRAM, EDO RAM) and the like.

I. Exemplary Wearable Physiological Measurement Systems

Exemplary embodiments provide wearable physiological measurements systems that are configured to provide continuous measurement of heart rate. Exemplary systems are configured to be continuously wearable on an appendage, for example, a wrist or an ankle, and do not rely on electrocardiography or chest straps in detection of heart rate. The exemplary system includes one or more light emitters for emitting light at one or more desired frequencies toward the user's skin, and one or more light detectors for received light reflected from the user's skin. The light detectors may include a photo-resistor, a photo-transistor, a photo-diode, and the like. As light from the light emitters (for example, green light) pierces through the skin of the user, the blood's natural absorbance or transmittance for the light provides fluctuations in the photo-resistor readouts. These waves have the same frequency as the user's pulse since increased absorbance or transmittance occurs only when the blood flow has increased after a heartbeat. The system includes a processing module implemented in software, hardware, or a combination thereof for processing the optical data received at the light detectors and continuously determining the heart rate based on the optical data. The optical data may be combined with data from one or more motion sensors, e.g., accelerometers and/or gyroscopes, to minimize or eliminate noise in the heart rate signal caused by motion or other artifacts (or with other optical data of another wavelength).

FIG. 1 illustrates front and back perspective views of one embodiment of a wearable system configured as a bracelet 100 including one or more straps 102. The bracelet 100 may be sleek and lightweight, thereby making it appropriate for continuous wear. The bracelet 100 may or may not include a display screen, e.g., user interface 106 such as a light emitting diode (LED) display for displaying any desired data (e.g., instantaneous heart rate).

As shown in the non-limiting embodiment in FIG. 1, the strap 102 of the bracelet 100 may have a wider side and a narrower side. In one embodiment, a user may simply insert the narrower side into the thicker side and squeeze the two together until the strap 102 is tight around the wrist. To remove the strap 102, a user may push the strap 102 further inwards, which unlocks the strap 102 and allows it to be released from the wrist. In other embodiments, various other fastening means may be provided. For example, the fastening mechanism may include, without limitation, a clasp, clamp, clip, dock, friction fit, hook and loop, latch, lock, pin, screw, slider, snap, button, spring, yoke, and so on.

In some embodiments, the strap 102 of the bracelet 100 may be a slim elastic band formed of any suitable elastic material, for example, rubber. Certain embodiments of the wearable system may be configured to have one size that fits all. Other embodiments may provide the ability to adjust for different wrist sizes. In one aspect, a combination of constant module strap material, a spring-loaded, floating optical system and a silicon-rubber finish may be used to achieve coupling while maintaining the strap's comfort for continuous use. Use of medical-grade materials to avoid skin irritations may be utilized.

As shown in FIG. 1, the wearable system (e.g., the bracelet 100) may include components configured to provide various functions such as data collection and streaming functions of the system. In some embodiments, the wearable system may include a button underneath the wearable system. In some embodiments, the button may be configured such that, when the wearable system is properly tightened to one's wrist, the button may press down and activate the system to begin storing information. In other embodiments, the button may be disposed and configured such that it may be pressed manually at the discretion of a user to begin storing information or otherwise to mark the start or end of an activity period. In some embodiments, the button may be held to initiate a time stamp and held again to end a time stamp, which may be transmitted, directly or through a mobile communication device application, to a website as a time stamp.

The wearable system may include a heart rate monitor. The wearable system may be configured such that, when a user wears it around their wrist and tightens it, the sensor portion of the wearable system is secured over the user's radial artery or other blood vessel. Secure connection and placement of the pulse sensor over the radial artery or other blood vessel may allow measurement of heart rate and pulse. It will be understood that this configuration is provided by way of example only, and that other sensors, sensor positions, and monitoring techniques may also or instead be employed without departing from the scope of this disclosure.

In some embodiments, the pulse or heart rate may be taken using an optical sensor coupled with one or more light emitting diodes (LEDs), all directly in contact with the user's wrist. The LEDs are provided in a suitable position from which light can be emitted into the user's skin. In one example, the LEDs mounted on a side or top surface of a circuit board in the system to prevent heat buildup on the LEDs and to prevent burns on the skin. The circuit board may be designed with the intent of dissipating heat, e.g., by including thick conductive layers, exposed copper, heatsink, or similar. In one aspect, the pulse repetition frequency is such that the amount of power thermally dissipated by the LED is negligible.

In some embodiments, the wearable system may be configured to record other physiological parameters including, but not limited to, skin temperature (using a thermometer), galvanic skin response (using a galvanic skin response sensor), motion (using one or more multi-axes accelerometers and/or gyroscope), and the like, and environmental or contextual parameters, e.g., ambient temperature, humidity, time of day, and the like. In an implementation, sensors are used to provide at least one of continuous motion detection, environmental temperature sensing, electrodermal activity (EDA) sensing, galvanic skin response (GSR) sensing, and the like. In this manner, an implementation can identify the cause of a detected physiological event. Reflectance PhotoPlethysmoGraphy (RPPG) may be used for the detection of cardiac activity, which may provide for non-intrusive data collection, usability in wet, dusty, and otherwise harsh environments, and low power requirements. For example, as explained herein, using the physiological readouts of the device and the analytics described herein, an "Intensity Score" (e.g., 0-21) (e.g., that measures a user's recent exertion), a "Recovery Score" (e.g., 0-100%), and "Sleep Score" (e.g., 0-100) may together measure readiness for physical and psychological exertion.

The wearable system may include one or more sources of battery life, e.g., two or more batteries. In some embodiments, it may have a battery that can slip onto and off of the head of the wearable system and can be recharged using an accessory. Additionally, the wearable system may have a built-in battery that is less powerful. When the more powerful battery is being charged, the user does not need to remove the wearable system and can still record data (during sleep, for example) using the built-in battery. The wearable system may perform numerous related functions, such as automatically detecting when the user is asleep, awake but at rest and exercising based on physiological data collected by the system.

The strap 102 of a physiological measurement system may be provided with a set of components that enables continuous monitoring of at least a heart rate of the user so that it is independent and fully self-sufficient in continuously monitoring the heart rate without requiring the modular head portion 104. In one embodiment, the strap 102 includes a plurality of light emitters for emitting light toward the user's skin, a plurality of light detectors for receiving light reflected from the user's skin, an electronic circuit board comprising a plurality of electronic components configured for analyzing data corresponding to the reflected light to automatically and continually determine a heart rate of the user, and a first set of one or more batteries for supplying electrical power to the light emitters, the light detectors and the electronic circuit board. In some embodiments, the strap 102 may also detect one or more other physiological characteristics of the user including, but not limited to, temperature, galvanic skin response, and the like. The strap may include one or more slots for permanently or removably coupling batteries to the strap 102.

Certain exemplary systems may be configured to be coupled to any desired part of a user's body so that the system may be moved from one portion of the body (e.g., wrist) to another portion of the body (e.g., ankle) without affecting its function and operation. An exemplary system may include an electronic circuit board comprising a plurality of electronic components configured for analyzing data corresponding to the reflected light to automatically and continually determine a heart rate of the user. The electronic circuit board may implement a processing module configured to detect an identity of a portion of the user's body, for example, an appendage like a wrist or an ankle, to which the strap is coupled based on one or more signals associated with the heart rate of the user, and based on the identity of the appendage, may adjust data analysis of the reflected light to determine the heart rate of the user.

In one embodiment, the identity of the portion of the user's body to which the wearable system is attached may be determined based on one or more parameters including, but not limited to, absorbance level of light as returned from the user's skin, reflectance level of light as returned from the user's skin, motion sensor data (e.g., accelerometer and/or gyroscope), altitude of the wearable system, and the like.

In some embodiments, the processing module may be configured to determine that the wearable system has been taken off from the user's body. In one example, the processing module may determine that the wearable system has been taken off if data from the galvanic skin response sensor indicates data atypical of a user's skin. If the wearable system is determined to be taken off from the user's body, the processing module may be configured to deactivate the light emitters and the light detectors and cease monitoring of the heart rate of the user to conserve power.

Exemplary systems include a processing module configured to filter the raw photoplethysmography data received from the light detectors to minimize contributions due to motion, and subsequently process the filtered data to detect peaks in the data that correspond with heart beats of a user. The overall algorithm for detecting heart beats may take as input the analog signals from optical sensors (mV) and accelerometer, and may output an implied beats per minute (heart rate) of the signal accurate within a few beats per minute as that determined by an electrocardiography machine even during motion.

In one aspect, using multiple LEDs with different wavelengths reacting to movement in different ways may allow for signal recovery with standard signal processing techniques. The availability of accelerometer information may also be used to compensate for coarse movement signal corruption. In order to increase the range of movements that the algorithm can successfully filter out, an aspect may utilize techniques that augment the algorithm already in place. For example, filtering violent movements of the arm during very short periods of time, such as boxing as exercising, may be utilized by the system. By selective sampling and interpolating over these impulses, an aspect may account for more extreme cases of motion. Additionally, an investigation into different LED wavelengths, intensities, and configurations may allow the systems described herein to extract a signal across a wide spectrum of skin types and wrist sizes. In other words, motion filtering algorithms and signal processing techniques may assist in mitigating the risk caused by movement.

Figure 2:
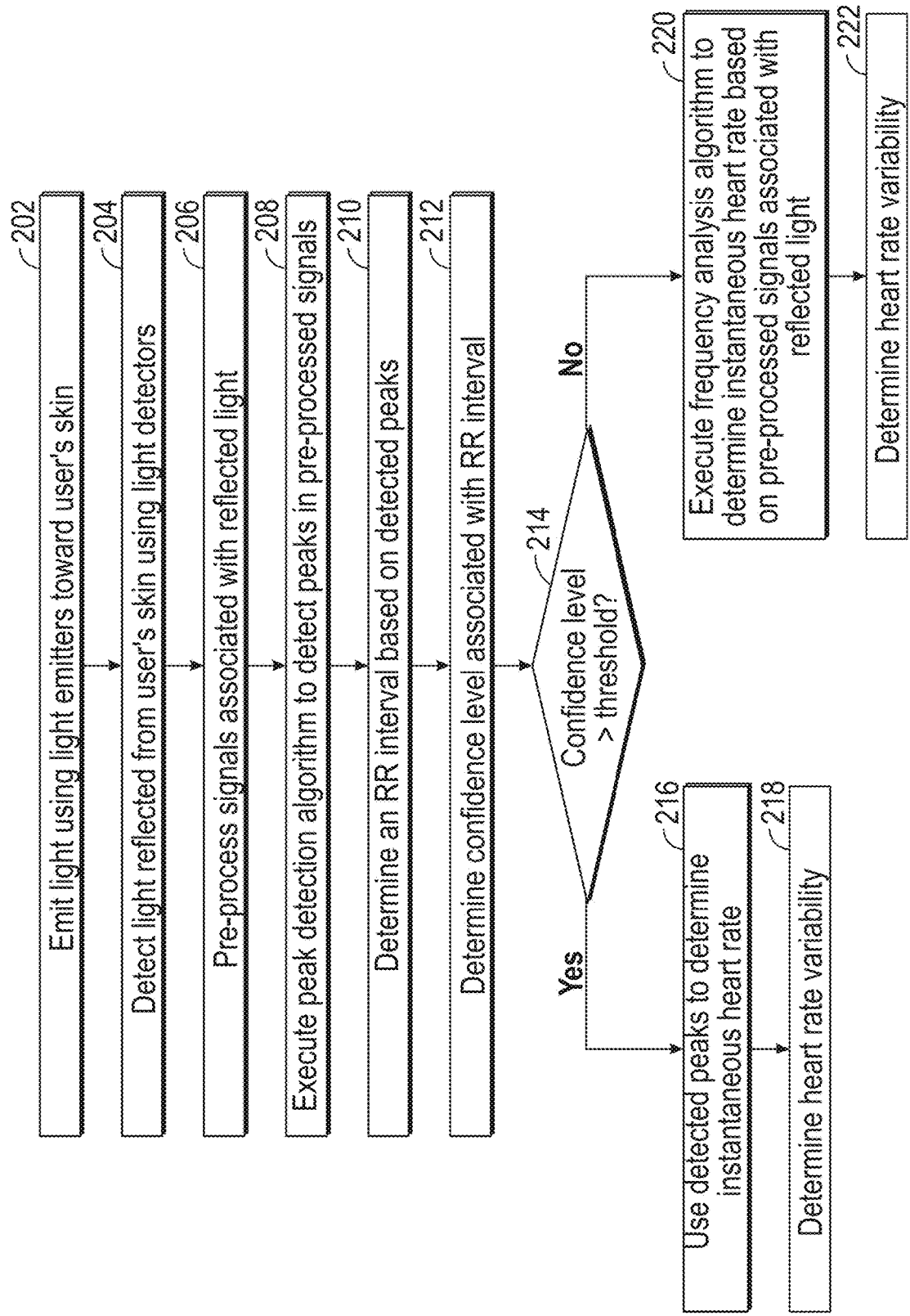
FIG. 2 is a flow chart illustrating a signal processing algorithm for generating a sequence of heart rates for every detected heartbeat that may be embodied in computer-executable instructions stored on one or more non-transitory computer-readable media.

FIG. 2 is a flow chart illustrating an exemplary signal processing algorithm for generating a sequence of heart rates for every detected heartbeat that is embodied in computer-executable instructions stored on one or more non-transitory computer-readable media. In step 202, light emitters of a wearable physiological measurement system may emit light toward a user's skin. In step 204, light reflected from the user's skin may be detected at the light detectors in the system. In step 206, signals or data associated with the reflected light may be pre-processed using any suitable technique to facilitate detection of heart beats. In step 208, a processing module of the system may execute one or more computer-executable instructions associated with a peak detection algorithm to process data corresponding to the reflected light to detect a plurality of peaks associated with a plurality of beats of the user's heart. In step 210, the processing module may determine an RR interval based on the plurality of peaks detected by the peak detection algorithm. In step 212, the processing module may determine a confidence level associated with the RR interval.

Based on the confidence level associated with the RR interval estimate, the processing module may select either the peak detection algorithm or a frequency analysis algorithm to process data corresponding to the reflected light to determine the sequence of instantaneous heart rates of the user. The frequency analysis algorithm may process the data corresponding to the reflected light based on the motion of the user detected using, for example, an accelerometer. The processing module may select the peak detection algorithm or the frequency analysis algorithm regardless of a motion status of the user. It is advantageous to use the confidence in the estimate in deciding whether to switch to frequency-based methods as certain frequency-based approaches are unable to obtain accurate RR intervals for heart rate variability analysis. Therefore, an implementation maintains the ability to obtain the RR intervals for as long as possible, even in the case of motion, thereby maximizing the information that can be extracted.

For example, in step 214, it may be determined whether the confidence level associated with the RR interval is above (or equal to or above) a threshold. In certain embodiments, the threshold may be predefined, for example, about 50%-90% in some embodiments and about 80% in one non-limiting embodiment. In other embodiments, the threshold may be adaptive, i.e., the threshold may be dynamically and automatically determined based on previous confidence levels. For example, if one or more previous confidence levels were high in value (i.e., above a certain level), the system may determine that a present confidence level that is relatively low compared to the previous levels is indicative of a less reliable signal. In this case, the threshold may be dynamically adjusted to be higher so that a frequency-based analysis method may be selected to process the less reliable signal.

If the confidence level is above (or equal to or above) the threshold, in step 216, the processing module may use the plurality of peaks to determine an instantaneous heart rate of the user. On the other hand, in step 220, based on a determination that the confidence level associated with the RR interval is equal to or below the predetermined threshold, the processing module may execute one or more computer-executable instructions associated with the frequency analysis algorithm to determine an instantaneous heart rate of the user. The confidence threshold may be dynamically set based on previous confidence levels.

In some embodiments, in steps 218 or 222, the processing module may determine a heart rate variability of the user based on the sequence of the instantaneous heart rates/beats.

The system may include a display device configured to render a user interface for displaying the sequence of the instantaneous heart rates of the user, the RR intervals and/or the heart rate variability determined by the processing module. The system may include a storage device configured to store the sequence of the instantaneous heart rates, the RR intervals and/or the heart rate variability determined by the processing module.

In one aspect, the system may switch between different analytical techniques for determining a heart rate such as a statistical technique for detecting a heart rate and a frequency domain technique for detecting a heart rate. These two different modes have different advantages in terms of accuracy, processing efficiency, and information content, and as such may be useful at different times and under different conditions. Rather than selecting one such mode or technique as an attempted optimization, the system may usefully switch back and forth between these differing techniques, or other analytical techniques, using a predetermined criterion. For example, where statistical techniques are used, a confidence level may be determined and used as a threshold for switching to an alternative technique such as a frequency domain technique. The threshold may also or instead depend on historical, subjective, and/or adapted data for a particular user. For example, selection of a threshold may depend on data for a particular user including without limitation subjective information about how a heart rate for a particular user responds to stress, exercise, and so forth. Similarly, the threshold may adapt to changes in fitness of a user, context provided from other sensors of the wearable system, signal noise, and so forth.

An exemplary statistical technique may employ probabilistic peak detection. In this technique, a discrete probabilistic step may be set, and a likelihood function may be established as a mixture of a Gaussian random variable and a uniform. The heart of the likelihood function encodes the assumption that with a first probability (p) the peak detection algorithm has produced a reasonable initial estimate, but with a second probability (1−p) it has not. In a subsequent step, Bayes' rule is applied to determine the posterior density on the parameter space, of which the maximum is taken (that is, the argument (parameter) that maximizes the posterior distribution). This value is the estimate for the heart rate. In a subsequent step, the previous two steps may be reapplied for the rest of the sample. There is some variance in the signal due to process noise, which is dependent on the length of the interval. This process noise may become the variance in the Gaussians used for the likelihood function. Then, the estimate may be obtained as the maximum a posteriori on the new posterior distribution. A confidence value may be recorded for the estimate which, for some precision measurement, the posterior value may be summed at points in the parameter space centered at our estimate+/−the precision.

The beats per minute (BPM) parameter space, θ, may range between about 20 and about 240, corresponding to the empirical bounds on human heart rates. In an exemplary method, a probability distribution may be calculated over this parameter space, at each step declaring the mode of the distribution to be the heart rate estimate. A discrete uniform prior may be set:

$$\pi_1 \sim DiscUnif(\theta)$$

The un-normalized, univariate likelihood is defined by a mixture of a Gaussian function and a uniform:

$$l_1 \sim IG + (1-I)U, \ G \sim N(\gamma_1 \sigma^2), \ I \sim Ber(p)$$

where $$U \sim DiscUnif(\theta)$$

and where σ and p are predetermined constants.

Bayes' rule may be applied to determine the posterior density on θ, for example, by component-wise multiplying the prior density vector $(\pi_1(\theta))_{\theta \in \Theta}$ with the likelihood vector $(l_1(\theta))_{\theta \in \Theta}$ to obtain the posterior distribution $\eta_1$. Then, the following is set:

$$\beta_1 = \mathrm{argmax}_{\theta \in \Theta} \eta_1(\theta)$$

For k≥2, the variance in signal S(t) due to process noise may be determined. Then, the following variable may be set to imbue temporally long RR intervals with more process/interpeak noise and set the post-normalization convolution:

$$\pi_k = \eta_{k-1} * f_{N(o, \lambda_k^2)|\theta}$$

where $f$ is a density function of the following:

$$Z \sim N(o, \lambda_k^2)$$

Then, the following expressions may be calculated:

$$l_k \sim pG_k + (1-p)U, \; G_k \sim N(\lambda k, \sigma^2)$$

The expression may then be normalized and recorded:

$$\beta_k = \mathrm{argmax}_{\theta \in \Theta} \eta_k(\theta)$$

Finally, the confidence level of the above expression for a particular precision threshold may be determined:

$$C_k = \sum_{\theta \in [\beta_k - e_1, \beta_k + e] \cap \Theta} \eta_k.$$

An exemplary frequency analysis algorithm used in an implementation may isolate the highest frequency components of the optical data, check for harmonics common in both the accelerometer data and the optical data, and perform filtering of the optical data. The algorithm may take as input raw analog signals from the accelerometer (3-axis) and pulse sensors, and output heart rate values or beats per minute (BPM) for a given period of time related to the window of the spectrogram.

The isolation of the highest frequency components may be performed in a plurality of stages, gradually winnowing the window-sizes of consideration, thereby narrowing the range of errors. In one implementation, a spectrogram of 2^15 samples with overlap 2^13 samples of the optical data may be generated. The spectrogram may be restricted to frequencies in which heart rate can lie. These restriction boundaries may be updated when smaller window sizes are considered. The frequency estimate may be extracted from the spectrogram by identifying the most prominent frequency component of the spectrogram for the optical data. The frequency may be extracted using the following exemplary steps. The most prominent frequency of the spectrogram may first be identified in the signal. It may be determined whether the frequency estimate is a harmonic of the true frequency. The frequency estimate may then be replaced with the true frequency if the estimate is a harmonic of the true frequency. It may be determined if the current frequency estimate is a harmonic of the motion sensor data. The frequency estimate may then be replaced with a previous temporal estimate if it is a harmonic of the motion sensor data. The upper and lower bounds on the frequency obtained may be saved. A constant value may be added or subtracted in some cases. In subsequent steps, the constant added or subtracted may finally be reduced to provide narrower searches. Any number of the previous steps may be repeated one or more times, e.g., three times, except taking 2^{15-i} samples for the window size and 2^{13-i} for the overlap in the spectrogram where i is the current number of iterations. The final output may be the average of the final symmetric endpoints of the frequency estimation.

The table below demonstrates the performance of the algorithm disclosed herein. To arrive at the results below, experiments were conducted in which a subject wore an exemplary wearable physiological measurement system and a 3-lead ECG which were both wired to the same microcontroller (e.g., Arduino) to provide time-synced data. Approximately 50 data sets were analyzed, which included the subject standing still, walking, and running on a treadmill.

TABLE 1

Performance of signal processing algorithm disclosed herein

| | Clean data error (mean, std) in BPM | Noisy data error (mean, std) in BPM |
| --- | --- | --- |
| 4-level spectrogram (80 second blocks) | 0.2, 2.3 | 0.8, 5.1 |

The algorithm's performance comes from a combination of a probabilistic and frequency based approach. The three difficulties in creating algorithms for heart rate calculations from the PPG data are 1) false detections of beats, 2) missed detections of real beats, and 3) errors in the precise timing of the beat detection. The algorithms disclosed herein provide improvements in these three sources of error and, in some cases, the error is bound to within 2 BPM of ECG values at all times even during the most motion intense activities.

The exemplary wearable system may compute heart rate variability (HRV) to obtain an understanding of the recovery status of the body. These values may be captured right before a user awakes or when the user is not moving, in both cases photoplethysmography (PPG) variability yielding equivalence to the ECG HRV. HRV is traditionally measured using an ECG machine and obtaining a time series of R-R intervals. Because an exemplary wearable system utilizes photoplethysmography (PPG), it does not obtain the electric signature from the heart beats; instead, the peaks in the obtained signal may correspond to arterial blood volume. At rest, these peaks may be directly correlated with cardiac cycles, which enables the calculation of HRV via analyzing peak-to-peak intervals (the PPG analog of RR intervals). It has been demonstrated that these peak-to-peak intervals, the "PPG variability," are identical to the ECG HRV while at rest.

Exemplary physiological measurement systems may be configured to minimize power consumption so that the systems may be worn continuously without requiring power recharging at frequent intervals. The majority of current draw in an exemplary system may be allocated to power the light emitters, e.g., LEDs, the wireless transceiver, the microcontroller, and peripherals. In one embodiment, the circuit board of the system may include a boost converter that runs a current of about 10 mA through each of the light emitters with an efficiency of about 80% and may draw power directly from the batteries at substantially constant power. With exemplary batteries at about 3.7 V, the current draw from the battery may be about 40 mW. In some embodiments, the wireless transceiver may draw about 10-20 mA of current when it is actively transferring data. In some embodiments, the microcontroller and peripherals may draw about 5 mA of current.

An exemplary system may include a processing module that is configured to automatically adjust one or more operational characteristics of the light emitters and/or the light detectors to minimize power consumption while ensuring that all heart beats of the user are reliably and continuously detected. The operational characteristics may include, but are not limited to, a frequency of light emitted by the light emitters, the number of light emitters activated, a duty cycle of the light emitters, a brightness of the light emitters, a sampling rate of the light detectors, and the like.

The processing module may adjust the operational characteristics based on one or more signals or indicators obtained or derived from one or more sensors in the system including, but not limited to, a motion status of the user, a sleep status of the user, historical information on the user's physiological and/or habits, an environmental or contextual condition (e.g., ambient light conditions), a physical characteristic of the user (e.g., the optical characteristics of the user's skin), and the like.

In one embodiment, the processing module may receive data on the motion of the user using, for example, an accelerometer. The processing module may process the motion data to determine a motion status of the user which indicates the level of motion of the user, for example, exercise, light motion (e.g., walking), no motion or rest, sleep, and the like. The processing module may then adjust the duty cycle of one or more light emitters and the corresponding sampling rate of the one or more light detectors based on the motion status. For example, upon determining that the motion status indicates that the user is at a first higher level of motion, the processing module may activate the light emitters at a first higher duty cycle and sample the reflected light using light detectors sampling at a first higher sampling rate. Upon determining that the motion status indicates that the user is at a second lower level of motion, the processing module may then activate the light emitters at a second lower duty cycle and sample the reflected light using light detectors sampling at a second lower sampling rate. That is, the duty cycle of the light emitters and the corresponding sampling rate of the light detectors may be adjusted in a graduated or continuous manner based on the motion status or level of motion of the user. This adjustment ensures that heart rate data is detected at a sufficiently high frequency during motion to reliably detect all the heart beats of the user.

In non-limiting examples, the light emitters may be activated at a duty cycle ranging from about 1% to about 100%. In another example, the light emitters may be activated at a duty cycle ranging from about 20% to about 50% to minimize power consumption. Certain exemplary sampling rates of the light detectors may range from about 50 Hz to about 1000 Hz, but are not limited to these exemplary rates. Certain non-limiting sampling rates are, for example, about 100 Hz, 200 Hz, 500 Hz, and the like.

In one non-limiting example, the light detectors may sample continuously when the user is performing an exercise routine so that the error standard deviation is kept within 5 beats per minute (BPM). When the user is at rest, the light detectors may be activated for about a 1% duty cycle—10 milliseconds each second (i.e., 1% of the time) so that the error standard deviation is kept within 5 BPM (including an error standard deviation in the heart rate measurement of 2 BPM and an error standard deviation in the heart rate changes between measurement of 3 BPM). When the user is in light motion (e.g., walking), the light detectors may be activated for about a 10% duty cycle—100 milliseconds each second (i.e., 10% of the time) so that the error standard deviation is kept within 6 BPM (including an error standard deviation in the heart rate measurement of 2 BPM and an error standard deviation in the heart rate changes between measurement of 4 BPM).

The processing module may adjust the brightness of one or more light emitters by adjusting the current supplied to the light emitters. For example, a first level of brightness may be set by current ranging between about 1 mA to about 10 mA, but is not limited to this exemplary range. A second higher level of brightness may be set by current ranging from about 11 mA to about 30 mA, but is not limited to this exemplary range. A third higher level of brightness may be set by current ranging from about 80 mA to about 120 mA, but is not limited to this exemplary range. In one non-limiting example, first, second and third levels of brightness may be set by current of about 5 mA, about 20 mA and about 100 mA, respectively.

Shorter-wavelength LEDs may require more power than is required by other types of heart rate sensors, such as, a piezo-sensor or an infrared sensor. Therefore, an exemplary wearable system may provide and use a unique combination of sensors—one or more light detectors for periods where motion is expected and one or more piezo and/or infrared sensors for low motion periods (e.g., sleep)—to save battery life. Certain other embodiments of a wearable system may exclude piezo-sensors and/or infrared sensors.

For example, upon determining that the motion status indicates that the user is at a first higher level of motion (e.g., exercising), one or more light emitters may be activated to emit light at a first wavelength. Upon determining that the motion status indicates that the user is at a second lower level of motion (e.g., at rest), non-light based sensors may be activated. The threshold levels of motion that trigger adjustment of the type of sensor may be based on one or more factors including, but are not limited to, skin properties, ambient light conditions, and the like.

The system may determine the type of sensor to use at a given time based on the level of motion (e.g., via an accelerometer) and whether the user is asleep (e.g., based on movement input, skin temperature and heart rate). Based on a combination of these factors the system may selectively choose which type of sensor to use in monitoring the heart rate of the user. Common symptoms of being asleep are periods of no movement or small bursts of movement (such as shifting in bed), lower skin temperature (although it is not a dramatic drop from normal), drastic GSR changes, and heart rate that is below the typical resting heart rate when the user is awake. These variables depend on the physiology of a person and thus a machine learning algorithm may be trained with user-specific input to determine when the user is awake/asleep and determine from that the exact parameters that cause the algorithm to deem the user asleep.

In an exemplary configuration, the light detectors may be positioned on the underside of the wearable system while all the heart rate sensors may be positioned adjacent to each other. For example, the low power sensor(s) may be adjacent to the high power sensor(s) as the sensors may be chosen and placed where the strongest signal occurs. In one example configuration, a 3-axis accelerometer may be used that is located on the top part of the wearable system.

In some embodiments, the processing module may be configured to automatically adjust a rate at which data is transmitted by the wireless transmitter to minimize power consumption while ensuring that raw and processed data generated by the system is reliably transmitted to external computing devices. In one embodiment, the processing module may determine an amount of data to be transmitted (e.g., based on the amount of data generated since the time of the last data transmission), and may select the next data transmission time based on the amount of data to be transmitted. For example, if it is determined that the amount of data exceeds (or is equal to or greater than) a threshold level, the processing module may transmit the data or may schedule a time for transmitting the data. On the other hand, if it is determined that the amount of data does not exceed (or is equal to or lower than) the threshold level, the processing module may postpone data transmission to minimize power consumption by the transmitter. In one non-limiting example, the threshold may be set to the amount of data that may be sent in two seconds under current conditions. Exemplary data transmission rates may range from about 50 kbytes per second to about 1 MByte per second but are not limited to this exemplary range.

More generally, the above description contemplates a variety of techniques for sensing conditions relating to heart rate monitoring or related physiological activity either directly (e.g., confidence levels or accuracy of calculated heart rate) or indirectly (e.g., motion detection, temperature). However measured, these sensed conditions may be used to intelligently select from among a number of different modes, including hardware modes, software modes, and combinations of the foregoing, for monitoring heart rate based on, e.g., accuracy, power usage, detected activity states, and so forth. Thus, there is disclosed herein techniques for selecting from among two or more different heart rate monitoring modes according to a sensed condition.

II. Exemplary Physiological Analytics System

Exemplary embodiments provide an analytics system for providing qualitative and quantitative monitoring of a user's body, health, and physical training. The analytics system is implemented in computer-executable instructions encoded on one or more non-transitory computer-readable media. The analytics system may rely on and use continuous data on one or more physiological parameters including, but not limited to, heart rate. The continuous data used by the analytics system may be obtained or derived from an exemplary physiological measurement system disclosed herein, or may be obtained or derived from a derived source or system, for example, a database of physiological data. In some embodiments, the analytics system may compute, store, and display one or more indicators or scores relating to the user's body, health and physical training including, but not limited to, an intensity score and a recovery score. The scores may be updated in real-time and continuously or at specific time periods, for example, the recovery score may be determined every morning upon waking up, the intensity score may be determined in real-time or after a workout routine or for an entire day.

In certain exemplary embodiments, a fitness score may be automatically determined based on the physiological data of two or more users of exemplary wearable systems.

An intensity score or indicator may provide an accurate indication of the cardiovascular intensities experienced by the user during a portion of a day, during the entire day or during any desired period of time (e.g., during a week or month). The intensity score may be customized and adapted for the unique physiological properties of the user and may take into account, for example, the user's age, gender, anaerobic threshold, resting heart rate, maximum heart rate, and the like. If determined for an exercise routine, the intensity score may provide an indication of the cardiovascular intensities experienced by the user continuously throughout the routine. If determined for a period of including and beyond an exercise routine, the intensity score may provide an indication of the cardiovascular intensities experienced by the user during the routine as well as the activities the user performed after the routine (e.g., resting on the couch, active day of shopping) that may affect their recovery or exercise readiness.

Figure 3:
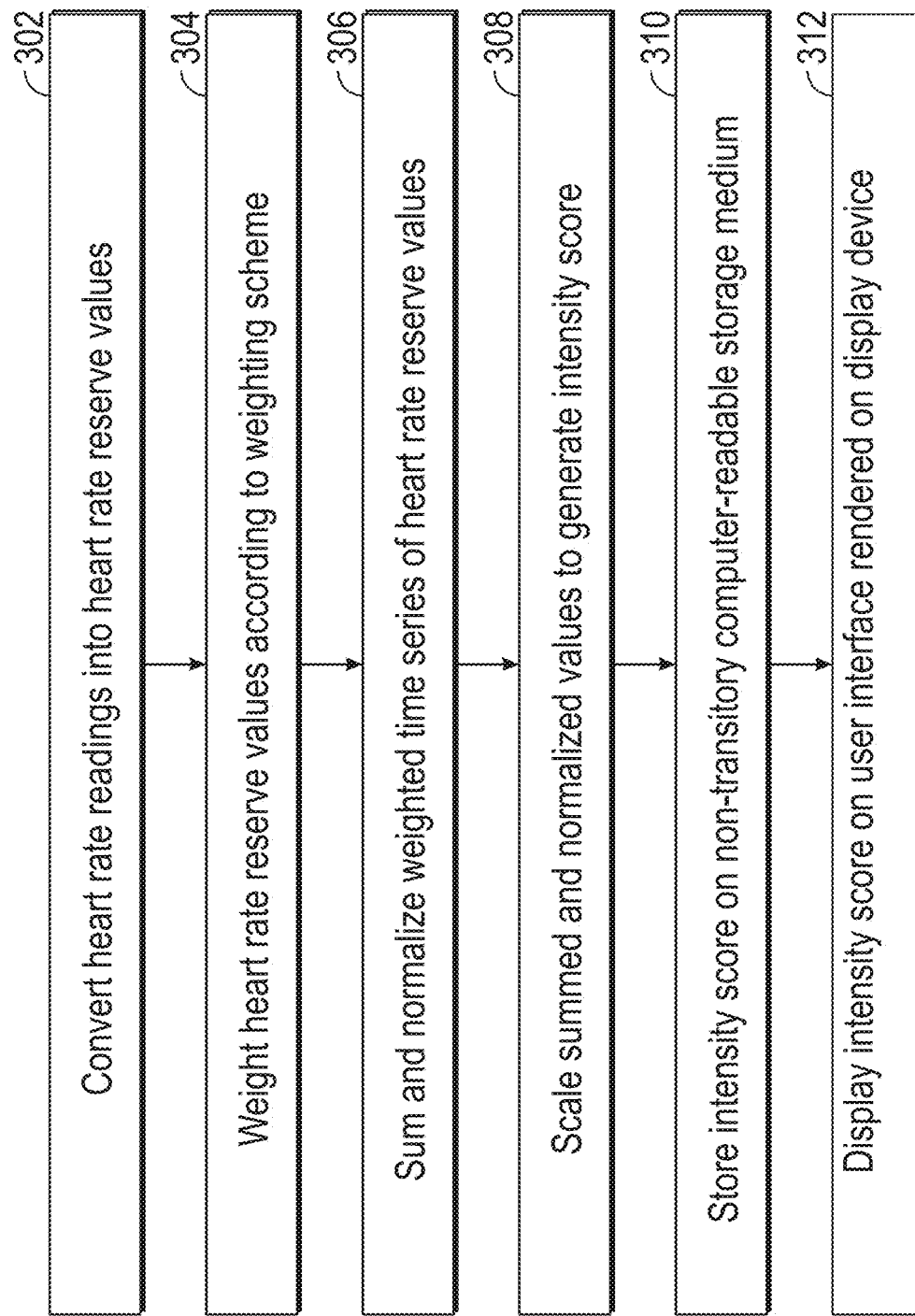
FIG. 3 is a flow chart illustrating a method of determining an intensity score.

FIG. 3 is a flow chart illustrating an exemplary method of determining an intensity score. In exemplary embodiments, the intensity score may be calculated based on the user's heart rate reserve (HRR) as detected continuously throughout the desired time period, for example, throughout the entire day. In one embodiment, the intensity score may be an integral sum of the weighted HRR detected continuously throughout the desired time period.

In step 302, continuous heart rate readings may be converted to HRR values. A time series of heart rate data used in step 302 may be denoted as:

$$H \in T$$

A time series of HRR measurements, v(t), may be defined in the following expression in which MHR is the maximum heart rate and RHR is the resting heart rate of the user:

$$v(t) = \frac{H(t) - RHR}{MHR - RHR}$$

In step 304, the HRR values may be weighted according to a suitable weighting scheme. Cardiovascular intensity, indicated by an intensity score, may be defined in the following expression in which w is a weighting function of the HRR measurements:

$$I(t_o, t_1) \int_{t_0}^{t_1} w(v(t)) dt$$

In step 306, the weighted time series of HRR values may be summed and normalized.

$$I_t = \int_T w(v(t)) dt \leq w(1)|T|$$

Thus, the weighted sum may be normalized to the unit interval, i.e., [0, 1]:

$$N_T = \frac{I_T}{w(1) \cdot 24 \text{ hr}}$$

In step 308, the summed and normalized values may be scaled to generate user-friendly intensity score values. That is, the unit interval may be transformed to have any desired distribution in a scale (e.g., a scale including 21 points from 0 to 21), for example, arctangent, sigmoid, sinusoidal, and the like. In certain distributions, the intensity values may increase at a linear rate along the scale, and in others, at the highest ranges the intensity values may increase at more than a linear rate to indicate that it is more difficult to climb in the scale toward the extreme end of the scale. In some embodiments, the raw intensity scores may be scaled by fitting a curve to a selected group of "canonical" exercise routines that are predefined to have particular intensity scores.

In one embodiment, monotonic transformations of the unit interval may be achieved to transform the raw HRR values to user-friendly intensity scores. An exemplary scaling scheme, expressed as $f: [0, 1] \rightarrow [0, 1]$, may be performed using the following function:

$$(x, N, p) = 0.5\left(\frac{\arctan(N(x-p))}{\pi/2} + 1\right)$$

To generate an intensity score, the resulting value may be multiplied by a number based on the desired scale of the intensity score. For example, if the intensity score is graduated from zero to 21, then the value may be multiplied by 21.

In step 310, the intensity score values may be stored on a non-transitory storage medium for retrieval, display and usage. In step 312, the intensity score values may be, in some embodiments, displayed on a user interface rendered on a visual display device. The intensity score values may be displayed as numbers and/or with the aid of graphical tools, e.g., a graphical display of the scale of intensity scores with current score, and the like. In some embodiments, the intensity score may be indicated by audio. In step 312, the intensity score values may be, in some embodiments, displayed along with one or more quantitative or qualitative pieces of information on the user including, but not limited to, whether the user has exceeded his/her anaerobic threshold, the heart rate zones experienced by the user during an exercise routine, how difficult an exercise routine was in the context of the user's training, the user's perceived exertion during an exercise routine, whether the exercise regimen of the user should be automatically adjusted (e.g., made easier if the intensity scores are consistently high), whether the user is likely to experience soreness the next day and the level of expected soreness, characteristics of the exercise routine (e.g., how difficult it was for the user, whether the exercise was in bursts or activity, whether the exercise was tapering, etc.), and the like. In one embodiment, the analytics system may automatically generate, store, and display an exercise regimen customized based on the intensity scores of the user.

Step 306 may use any of a number of exemplary static or dynamic weighting schemes that enable the intensity score to be customized and adapted for the unique physiological properties of the user. In one exemplary static weighting scheme, the weights applied to the HRR values may be based on static models of a physiological process. The human body employs different sources of energy with varying efficiencies and advantages at different HRR levels. For example, at the anaerobic threshold (AT), the body shifts to anaerobic respiration in which the cells produce two adenosine triphosphate (ATP) molecules per glucose molecule, as opposed to 36 at lower HRR levels. At even higher HRR levels, there is a further subsequent threshold (CPT) at which creatine triphosphate (CTP) is employed for respiration with even less efficiency.

In order to account for the differing levels of cardiovascular exertion and efficiency at the different HRR levels, in one embodiment, the possible values of HRR may be divided into a plurality of categories, sections or levels (e.g., three) dependent on the efficiency of cellular respiration at the respective categories. The HRR parameter range may be divided in any suitable manner, such as, piecewise, including piecewise-linear, piecewise-exponential, and the like. An exemplary piecewise-linear division of the HRR parameter range may enable weighting each category with strictly increasing values. This scheme captures an accurate indication of the cardiovascular intensity experienced by the user because it is more difficult to spend time at higher HRR values, which suggests that the weighting function should increase at the increasing weight categories.

In one non-limiting example, the HRR parameter range may be considered a range from zero (0) to one (1) and divided into categories with strictly increasing weights. In one example, the HRR parameter range may be divided into a first category of a zero HRR value and may assign this category a weight of zero; a second category of HRR values falling between zero (0) and the user's anaerobic threshold (AT) and may assign this category a weight of one (1); a third category of HRR values falling between the user's anaerobic threshold (AT) and a threshold at which the user's body employs creatine triphosphate for respiration (CPT) and may assign this category a weight of 18; and a fourth category of HRR values falling between the creatine triphosphate threshold (CPT) and one (1) and may assign this category a weight of 42, although other numbers of HRR categories and different weight values are possible. That is, in this example, the weights are defined as:

$$w(v) = \begin{cases} 0 & : v = 0 \\ 1 & : v \in (0, AT] \\ 18 & : v \in (AT, CPT] \\ 42 & : v \in (CPT, 1] \end{cases}$$

In another exemplary embodiment of the weighting scheme, the HRR time series may be weighted iteratively based on the intensity scores determined thus far (e.g., the intensity score accrued thus far) and the path taken by the HRR values to get to the present intensity score. The path may be detected automatically based on the historical HRR values and may indicate, for example, whether the user is performing high intensity interval training (during which the intensity scores are rapidly rising and falling), whether the user is taking long breaks between bursts of exercise (during which the intensity scores are rising after longer periods), and the like. The path may then be used to dynamically determine and adjust the weights applied to the HRR values. For example, in the case of high intensity interval training, the weights applied may be higher than in the case of a more traditional exercise routine.

In another exemplary embodiment of the weighting scheme, a predictive approach may be used by modeling the weights or coefficients to be the coefficient estimates of a logistic regression model. In this scheme, a training data set may be obtained by continuously detecting the heart rate time series and other personal parameters of a group of individuals. The training data set may be used to train a machine learning system to predict the cardiovascular intensities experienced by the individuals based on the heart rate and other personal data. The trained system may model a regression in which the coefficient estimates correspond to the weights or coefficients of the weighting scheme. In the training phase, user input on perceived exertion and the intensity scores may be compared. The learning algorithm may also alter the weighs based on the improving or declining health of a user as well as their qualitative feedback. This yields a unique algorithm that incorporates physiology, qualitative feedback, and quantitative data. In determining a weighting scheme for a specific user, the trained machine learning system may be run by executing computer-executable instructions encoded on one or more non-transitory computer-readable media, and may then generate the coefficient estimates which are then used to weight the user's HRR time series.

One of ordinary skill in the art will recognize that two or more aspects of any of the disclosed weighting schemes may be applied separately or in combination in an exemplary method for determining an intensity score.

In one aspect, heart rate zones may quantify the intensity of workouts by weighing and comparing different levels of heart activity as percentages of maximum heart rate. Analysis of the amount of time an individual spends training at a certain percentage of his/her MHR may reveal his/her state of physical exertion during a workout. This intensity, developed from the heart rate zone analysis, motion, and activity, may then indicate his/her need for rest and recovery after the workout, e.g., to minimize delayed onset muscle soreness (DOMS) and prepare him/her for further activity. As discussed above, MHR, heart rate zones, time spent above the anaerobic threshold, and HRV in RSA (Respiratory Sinus Arrhythmia) regions—as well as personal information (gender, age, height, weight, etc.) may be utilized in data processing.

A recovery score or indicator may provide an accurate indication of the level of recovery of a user's body and health after a period of physical exertion. The human autonomic nervous system controls the involuntary aspects of the body's physiology and is typically subdivided into two branches: parasympathetic (deactivating) and sympathetic (activating). Heart rate variability (HRV), i.e., the fluctuation in inter-heartbeat interval time, is a commonly studied result of the interplay between these two competing branches. Parasympathetic activation reflects inputs from internal organs, causing a decrease in heart rate. Sympathetic activation increases in response to stress, exercise, and disease, causing an increase in heart rate. For example, when high intensity exercise takes place, the sympathetic response to the exercise persists long after the completion of the exercise. When high intensity exercise is followed by insufficient recovery, this imbalance lasts typically until the next morning, resulting in a low morning HRV. This result should be taken as a warning sign as it indicates that the parasympathetic system was suppressed throughout the night. While suppressed, normal repair and maintenance processes that ordinarily would occur during sleep were suppressed as well. Suppression of the normal repair and maintenance processes results in an unprepared state for the next day, making subsequent exercise attempts more challenging.

The recovery score may be customized and adapted for the unique physiological properties of the user and may take into account, for example, the user's heart rate variability (HRV), resting heart rate, sleep quality and recent physiological strain (indicated, in one example, by the intensity score of the user). In one exemplary embodiment, the recovery score may be a weighted combination of the user's heart rate variability (HRV), resting heart rate, sleep quality indicated by a sleep score, and recent strain (indicated, in one example, by the intensity score of the user). In an exemplar, the sleep score combined with performance readiness measures (such as, morning heart rate and morning heart rate variability) may provide a complete overview of recovery to the user. By considering sleep and HRV alone or in combination, the user can understand how exercise-ready he/she is each day and to understand how he/she arrived at the exercise-readiness score each day, for example, whether a low exercise-readiness score is a predictor of poor recovery habits or an inappropriate training schedule. This insight aids the user in adjusting his/her daily activities, exercise regimen and sleeping schedule therefore obtain the most out of his/her training.

In some cases, the recovery score may take into account perceived psychological strain experienced by the user. In some cases, perceived psychological strain may be detected from user input via, for example, a questionnaire on a mobile device or web application. In other cases, psychological strain may be determined automatically by detecting changes in sympathetic activation based on one or more parameters including, but not limited to, heart rate variability, heart rate, galvanic skin response, and the like.

Regarding the user's HRV used in determining the recovery score, suitable techniques for analyzing HRV may include, but are not limited to, time-domain methods, frequency-domain methods, geometric methods, and non-linear methods. In one embodiment, the HRV metric of the root-mean-square of successive differences (RMSSD) of RR intervals may be used. The analytics system may consider the magnitude of the differences between 7-day moving averages and 3-day moving averages of these readings for a given day. Other embodiments may use Poincaré Plot analysis or other suitable metrics of HRV.

The recovery score algorithm may take into account RHR along with history of past intensity and recovery scores.

Regarding the user's resting heart rate, moving averages of the resting heart rate may be analyzed to determine significant deviations. Consideration of the moving averages is important since day-to-day physiological variation is quite large even in healthy individuals. Therefore, the analytics system may perform a smoothing operation to distinguish changes from normal fluctuations.

Although an inactive condition, sleep is a highly active recovery state during which a major portion of the physiological recovery process takes place. Nonetheless, a small, yet significant, amount of recovery can occur throughout the day by rehydration, macronutrient replacement, lactic acid removal, glycogen re-synthesis, growth hormone production and a limited amount of musculoskeletal repair. In assessing the user's sleep quality, the analytics system may generate a sleep score using continuous data collected by an exemplary physiological measurement system regarding the user's heart rate, skin conductivity, ambient temperature, and accelerometer/gyroscope data throughout the user's sleep. Collection and use of these four streams of data enable an understanding of sleep previously only accessible through invasive and disruptive over-night laboratory testing. For example, an increase in skin conductivity when ambient temperature is not increasing, the wearer's heart rate is low, and the accelerometer/gyroscope shows little motion, may indicate that the wearer has fallen asleep. The sleep score indicates and is a measure of sleep efficiency (how good the user's sleep was) and sleep duration (if the user had sufficient sleep). Each of these measures may be determined by a combination of physiological parameters, personal habits, and daily stress/strain (intensity) inputs. The actual data measuring the time spent in various stages of sleep may then be combined with the wearer's recent daily history and a longer-term data set describing the wearer's personal habits to assess the level of sleep sufficiency achieved by the user. The sleep score is designed to model sleep quality in the context of sleep duration and history. It thus takes advantage of the continuous monitoring nature of the exemplary physiological measurement systems disclosed herein by considering each sleep period in the context of biologically-determined sleep needs, pattern-determined sleep needs and historically-determined sleep debt.

The recovery and sleep score values may be stored on a non-transitory storage medium for retrieval, display and usage. The recovery and/or sleep score values may be, in some embodiments, displayed on a user interface rendered on a visual display device. The recovery and/or sleep score values may be displayed as numbers and/or with the aid of graphical tools, e.g., a graphical display of the scale of recovery scores with current score, and the like. In some embodiments, the recovery and/or sleep score may be indicated by audio. The recovery score values are, in some embodiments, displayed along with one or more quantitative or qualitative pieces of information on the user including, but not limited to, whether the user has recovered sufficiently, what level of activity the user is prepared to perform, whether the user is prepared to perform an exercise routine a particular desired intensity, whether the user should rest and the duration of recommended rest, whether the exercise regimen of the user should be automatically adjusted (e.g., made easier if the recovery score is low), and the like. In one embodiment, the analytics system may automatically generate, store, and display an exercise regimen customized based on the recovery scores of the user alone or in combination with the intensity scores.

As discussed above, the sleep performance metric may be based on parameters like the number of hours of sleep, sleep onset latency, and the number of sleep disturbances. In this manner, the score may compare a tactical athlete's duration and quality of sleep in relation to the tactical athlete's evolving sleep need (e.g., a number of hours based on recent strain, habitual sleep need, signs of sickness, and sleep debt). By way of example, a soldier may have a dynamically changing need for sleep, and it may be important to consider the total hours of sleep in relation to the amount of sleep that may have been required. By providing an accurate sensor for sleep and sleep performance, an aspect may evaluate sleep in the context of the overall day and lifestyle of a specific user.

Figure 4:
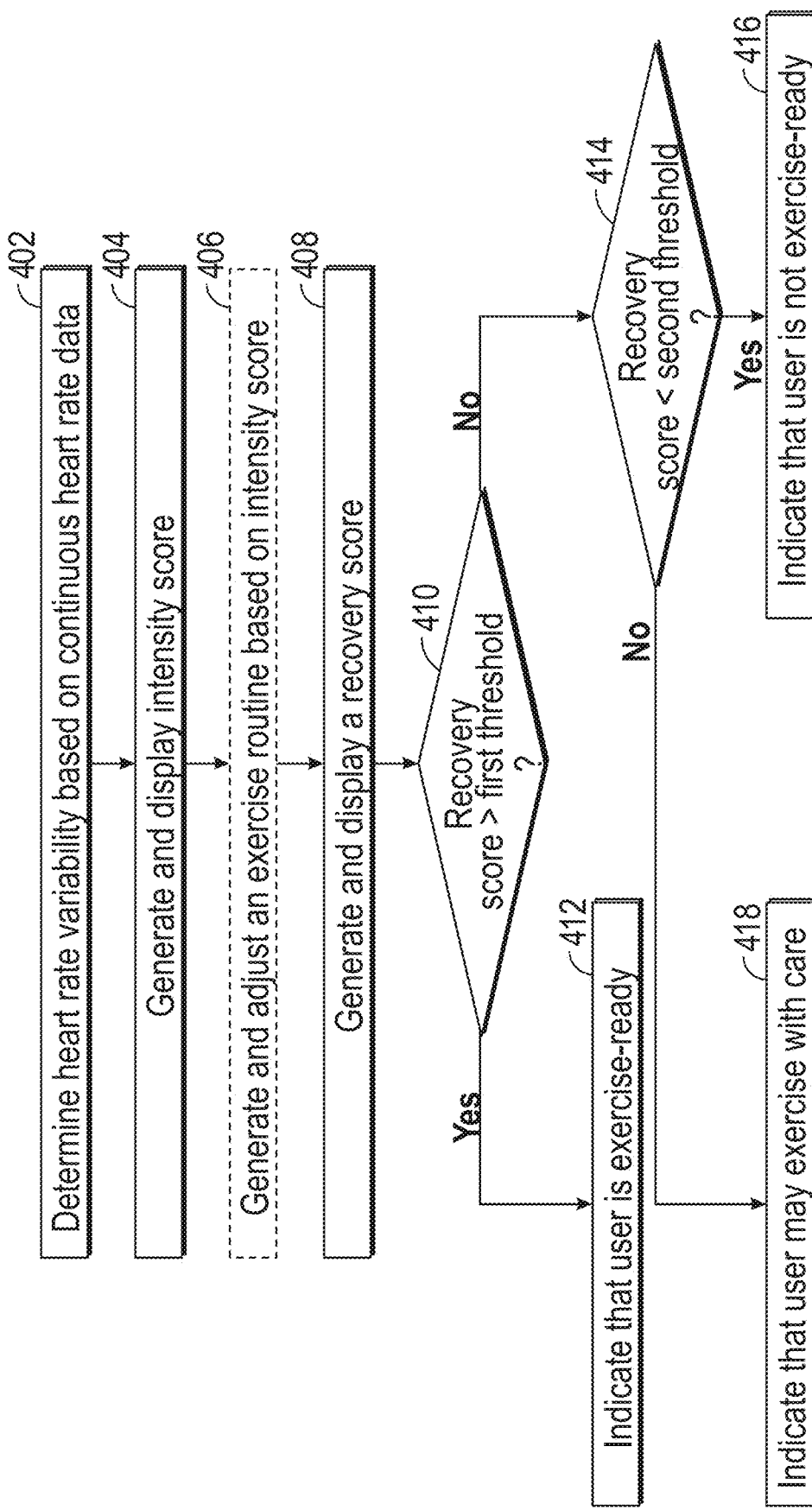
FIG. 4 is a flow chart illustrating a method by which a user may use intensity and recovery scores.

FIG. 4 is a flow chart illustrating an exemplary method by which a user may use intensity and recovery scores. In step 402, the wearable physiological measurement system may begin determining heart rate variability (HRV) measurements based on continuous heart rate data collected by an exemplary physiological measurement system. In some cases, it may take the collection of several days of heart rate data to obtain an accurate baseline for the HRV.

In step 404, the analytics system may generate and display intensity score for an entire day or an exercise routine. In some cases, the analytics system may display quantitative and/or qualitative information corresponding to the intensity score.

In step 406, in an exemplary embodiment, the analytics system may automatically generate or adjust an exercise routine or regimen based on the user's actual intensity scores or desired intensity scores. For example, based on inputs of the user's actual intensity scores, a desired intensity score (that is higher than the actual intensity scores) and a first exercise routine currently performed by the user (e.g., walking), the analytics system may recommend a second different exercise routine that is typically associated with higher intensity scores than the first exercise routine (e.g., running).

In step 408, at any given time during the day (e.g., every morning), the analytics system may generate and display a recovery score. In some cases, the analytics system may display quantitative and/or qualitative information corresponding to the intensity score. For example, in step 410, in an exemplary embodiment, the analytics system may determine if the recovery is greater than (or equal to or greater than) a first predetermined threshold (e.g., about 60% to about 80% in some examples) that indicates that the user is recovered and is ready for exercise. If this is the case, in step 412, the analytics system may indicate that the user is ready to perform an exercise routine at a desired intensity or that the user is ready to perform an exercise routine more challenging than the past day's routine. Otherwise, in step 414, the analytics system may determine if the recovery is lower than (or equal to or lower than) a second predetermined threshold (e.g., about 10% to about 40% in some examples) that indicates that the user has not recovered. If this is the case, in step 416, the analytics system may indicate that the user should not exercise and should rest for an extended period. The analytics system may, in some cases, determine the duration of recommended rest. Otherwise, in step 418, the analytics system may indicate that the user may exercise according to his/her exercise regimen while being careful not to overexert him/herself. The thresholds may then, in some cases, be adjusted based on a desired intensity at which the user desires to exercise. For example, the thresholds may be increased for higher planned intensity scores.

Figure 5:
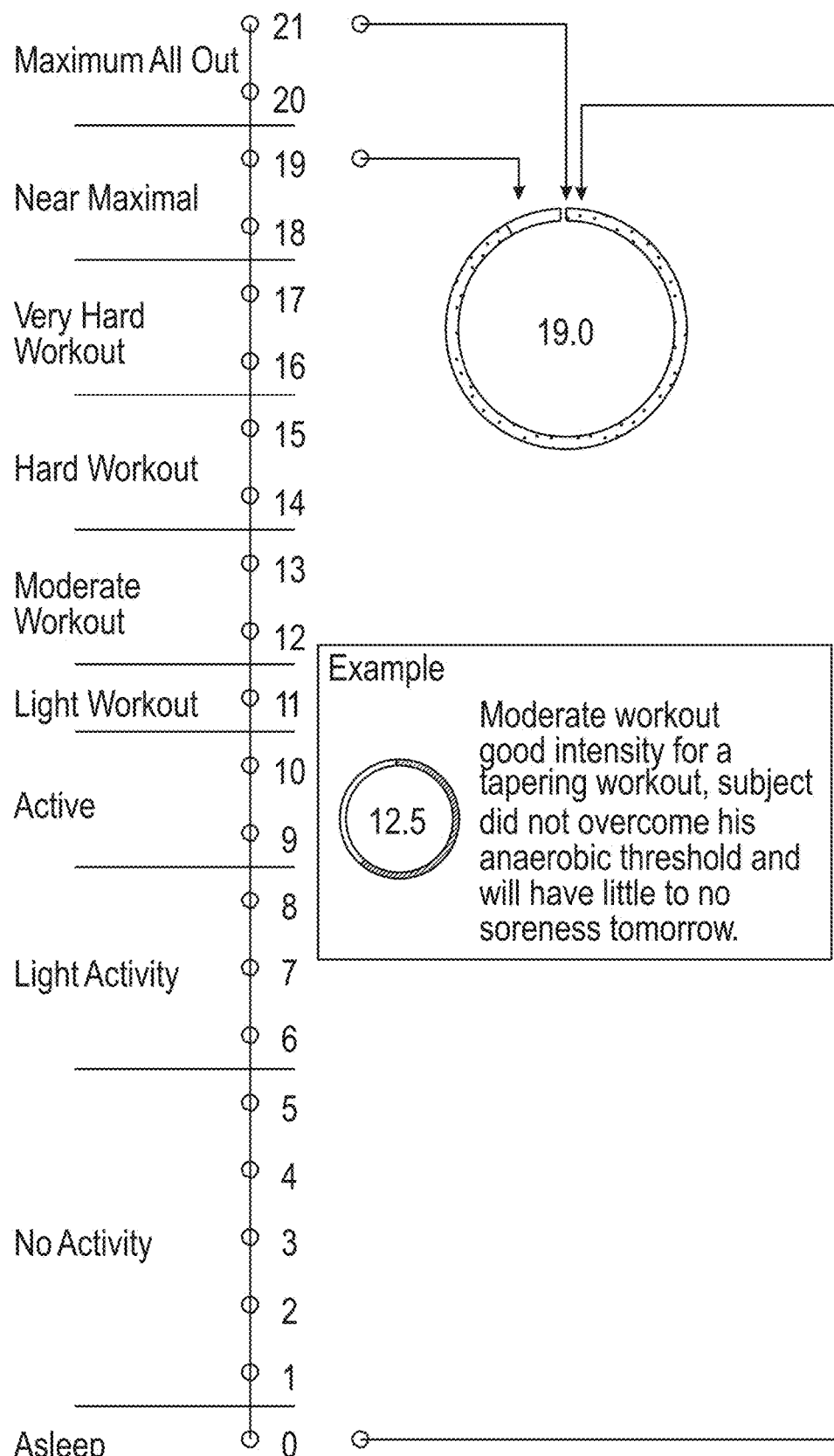
FIG. 5 illustrates a display of an intensity score index indicated in a circular graphic component with an exemplary current score of 19.0 indicated.

FIG. 5 illustrates an exemplary display of an intensity score index indicated in a circular graphic component with an exemplary current score of 19.0 indicated. The graphic component may indicate a degree of difficulty of the exercise corresponding to the current score selected from, for example, maximum all out, near maximal, very hard, hard, moderate, light, active, light active, no activity, asleep, and the like. The display may indicate, for example, that the intensity score corresponds to a good and tapering exercise routine, that the user did not overcome his anaerobic threshold and that the user will have little to no soreness the next day.

Figure 6:
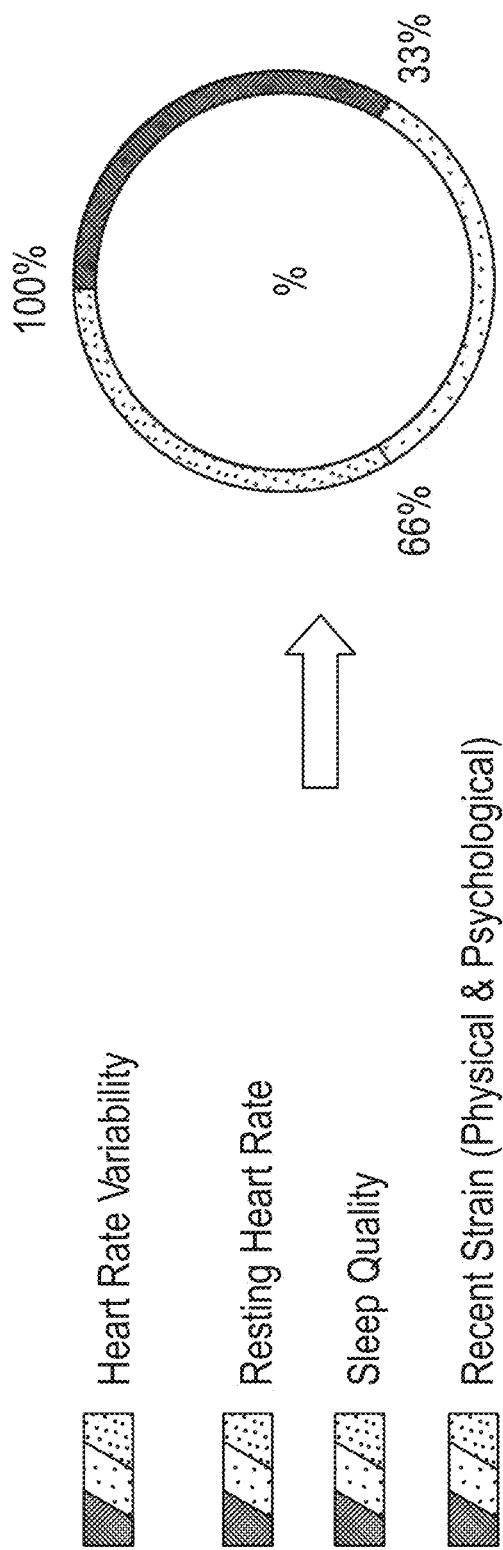
FIG. 6 illustrates a display of a recovery score index indicated in a circular graphic component with a first threshold of 66% and a second threshold of 33% indicated.

FIG. 6 illustrates an exemplary display of a recovery score index indicated in a circular graphic component with a first threshold of 66% and a second threshold of 33% indicated.

Figure 7A:
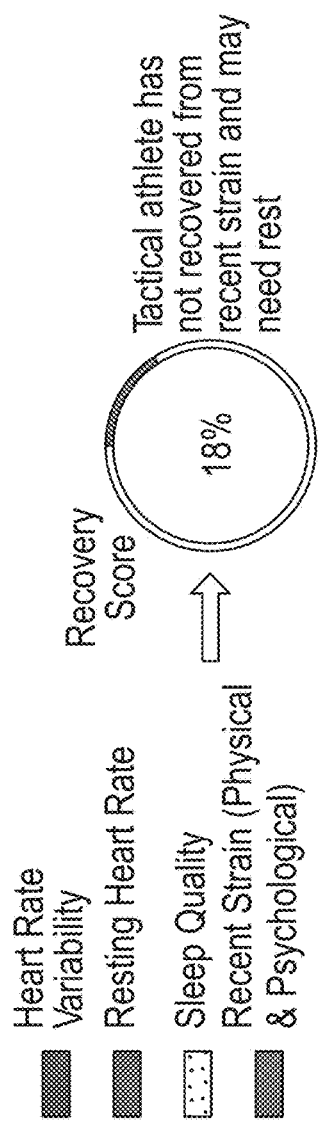
FIG. 7A illustrates a recovery score graphic component with a recovery score and qualitative information corresponding to the recovery score.
Figure 7B:
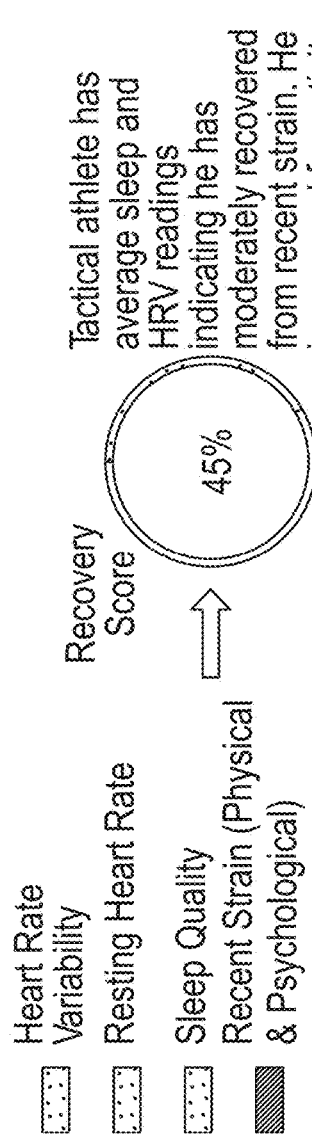
FIG. 7B illustrates a recovery score graphic component with a recovery score and qualitative information corresponding to the recovery score.
Figure 7C:
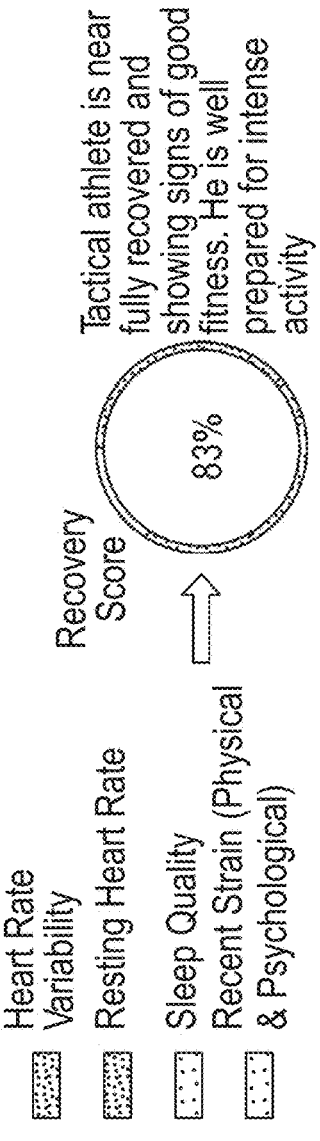
FIG. 7C illustrates a recovery score graphic component with a recovery score and qualitative information corresponding to the recovery score.

FIGS. 7A-7C illustrate the recovery score graphic component with exemplary recovery scores and qualitative information corresponding to the recovery scores.

Optionally, in an exemplary embodiment, the analytics system may automatically generate or adjust an exercise routine or regimen based on the user's actual recovery scores (e.g., to recommend lighter exercise for days during which the user has not recovered sufficiently). This process may also use a combination of the intensity and recovery scores.

The analytics system may, in some embodiments, determine and display the intensity and/or recovery scores of a plurality of users in a comparative manner. This enables users to match exercise routines with others based on comparisons among their intensity scores.

III. Exemplary Computing Devices

Various aspects and functions described herein may be implemented as hardware, software or a combination of hardware and software on one or more computer systems. Exemplary computer systems that may be used include, but are not limited to, personal computers, embedded computing systems, network appliances, workstations, mainframes, networked clients, servers, media servers, application servers, database servers, web servers, virtual servers, and the like. Other examples of computer systems that may be used include, but are not limited to, mobile computing devices, such as wearable devices, cellular phones and personal digital assistants, and network equipment, such as load balancers, routers, and switches.

Figure 8:
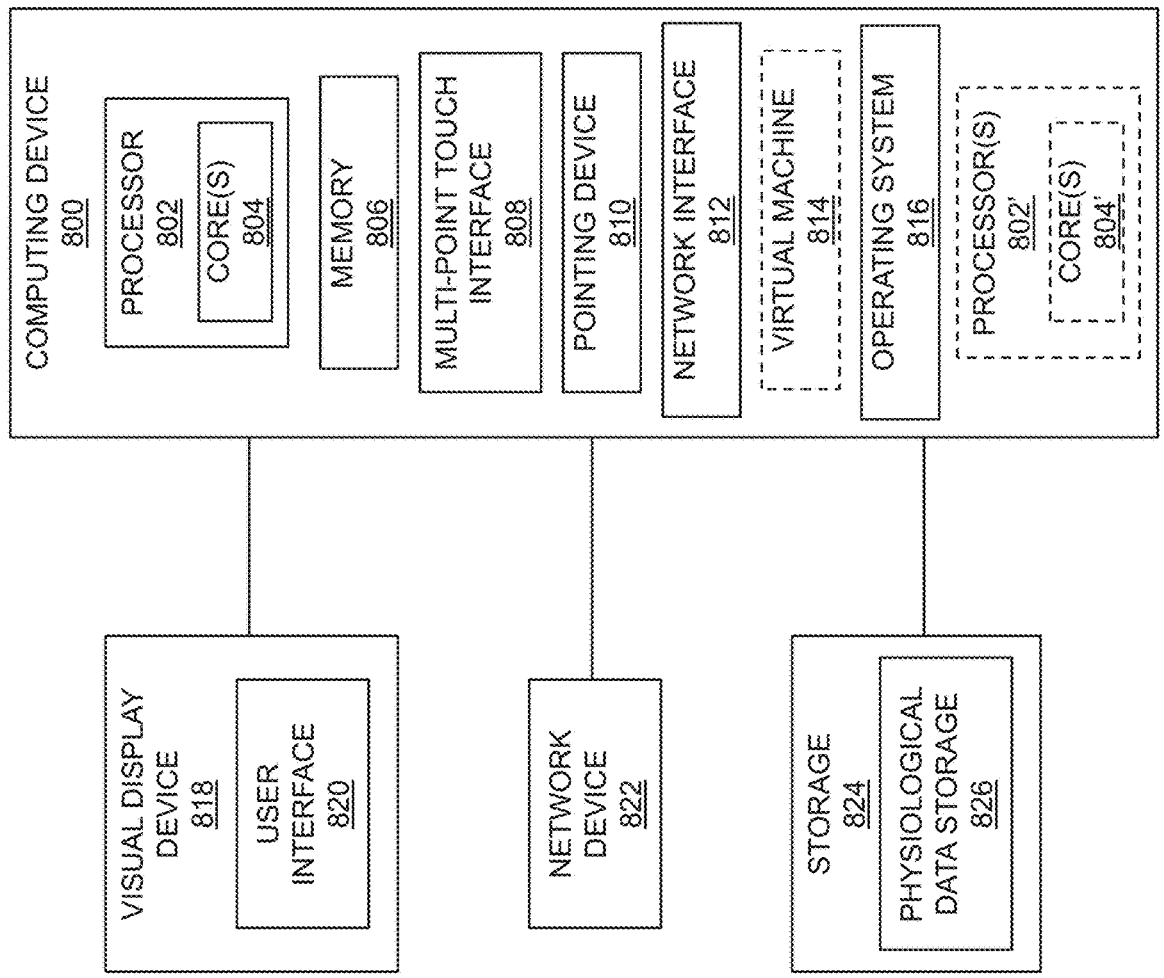
FIG. 8 is a block diagram of a computing device that may be used herein.

FIG. 8 is a block diagram of an exemplary computing device 800 that may be used in to perform any of the methods provided by exemplary embodiments. The computing device may be configured as an embedded system in the integrated circuit board(s) of a wearable physiological measurements system and/or as an external computing device that may receive data from a wearable physiological measurement system.

The computing device 800 includes one or more non-transitory computer-readable media for storing one or more computer-executable instructions or software for implementing exemplary embodiments. The non-transitory computer-readable media may include, but are not limited to, one or more types of hardware memory, non-transitory tangible media (for example, one or more magnetic storage disks, one or more optical disks, one or more USB flash drives), and the like. For example, memory 806 included in the computing device 800 may store computer-readable and computer-executable instructions or software for implementing exemplary embodiments. The computing device 800 also includes processor 802 and associated core 804, and optionally, one or more additional processor(s) 802' and associated core(s) 804' (for example, in the case of computer systems having multiple processors/cores), for executing computer-readable and computer-executable instructions or software stored in the memory 806 and other programs for controlling system hardware. Processor 802 and processor(s) 802' may each be a single core processor or multiple core (804 and 804') processor.

Virtualization may be employed in the computing device 800 so that infrastructure and resources in the computing device may be shared dynamically. A virtual machine 814 may be provided to handle a process running on multiple processors so that the process appears to be using only one computing resource rather than multiple computing resources. Multiple virtual machines may also be used with one processor.

Memory 806 may include a computer system memory or random access memory, such as DRAM, SRAM, EDO RAM, and the like. Memory 806 may include other types of memory as well, or combinations thereof.

A user may interact with the computing device 800 through a visual display device 818, such as a computer monitor, which may display one or more user interfaces 820 that may be provided in accordance with exemplary embodiments. The visual display device 818 may also display other aspects, elements and/or information or data associated with exemplary embodiments, for example, views of databases, photos, and the like. The computing device 800 may include other I/O devices for receiving input from a user, for example, a keyboard or any suitable multi-point touch interface 808, a pointing device 810 (e.g., a mouse). The keyboard 808 and the pointing device 810 may be coupled to the visual display device 818. The computing device 800 may include other suitable conventional I/O peripherals.

The computing device 800 may also include one or more storage devices 824, such as a hard-drive, CD-ROM, or other computer readable media, for storing data and computer-readable instructions and/or software that implement exemplary methods as taught herein. Exemplary storage device 824 may also store one or more databases 826 for storing any suitable information required to implement exemplary embodiments. The databases 826 may be updated by a user or automatically at any suitable time to add, delete or update one or more items in the databases.

The computing device 800 may include a network interface 812 configured to interface via one or more network devices 822 with one or more networks, for example, Local Area Network (LAN), Wide Area Network (WAN) or the Internet through a variety of connections including, but not limited to, standard telephone lines, LAN or WAN links (for example, 802.11, T1, T3, 56 kb, X.25), broadband connections (for example, ISDN, Frame Relay, ATM), wireless connections, controller area network (CAN), or some combination of any or all of the above. The network interface 812 may include a built-in network adapter, network interface card, PCMCIA network card, card bus network adapter, wireless network adapter, USB network adapter, modem, or any other device suitable for interfacing the computing device 800 to any type of network capable of communication and performing the operations described herein. Moreover, the computing device 800 may be any computer system, such as a workstation, desktop computer, server, laptop, handheld computer, tablet computer (e.g., the iPad® tablet computer), mobile computing or communication device (e.g., the iPhone® communication device), or other form of computing or telecommunications device that is capable of communication and that has sufficient processor power and memory capacity to perform the operations described herein.

The wearable physiological measurement system may record and transmit at least the following types of data to an external computing system, mobile communication system or the Internet: raw continuously-detected data (e.g., heart rate data, movement data, galvanic skin response data) and processed data based on the raw data (e.g., RR intervals determined from the heart rate data). Transmission modes may be wired (e.g., using USB stick inserted into a USB port on the system) or wireless (e.g., using a wireless transmitter). The raw and processed data may be transmitted together or separately using different transmission modes. Since a raw data file is typically substantially larger than a processed data file, the raw data file may be transmitted using WiFi or a USB stick, while the processed data file may be transmitted using Bluetooth.

An exemplary wearable system may include a 2G, 3G or 4G chip that wirelessly uploads all data to the website disclosed herein without requiring any other external device. A 3G or 4G chip may be used preferably as a 2G connection on a Nokia 5800 was found to transfer data at a rate of 520 kbps using 1.69 W, while a 3G connection transferred at 960 kbps using 1.73 W. Therefore, the 3G chip would use negligibly more power for almost twice the transfer speed, thereby halving half the transfer time and using much less energy from the battery.

In some cases, the wearable system may opportunistically transfer data when in close proximity to a streaming outlet. For example, the system may avoid data transmission when it is not within close proximity of a streaming outlet, and, when nearby a streaming outlet (e.g., a linked phone), may send the data to the external device via Bluetooth and to the Internet via the external device. This is both convenient and "free" in the sense that it utilizes existing cellular data plans.

Limiting the frequency with which data is streamed increases the wearable system's battery life. In one non-limiting example, the system may be set to stream automatically in the morning and following a time stamp. Regardless of the data transmission scheme, the system may store all the data it collects. Data may also be streamed on demand by a user, for example, by turning a physical component on the system and holding it or by initiating a process on the mobile application or receiving device. In some embodiments, the data frequency may be automatically adjusted based on one or more physiological parameters, e.g., heart rate. For example, higher heart rates may prompt more frequent and real-time streaming transmission of data.

The computing device 800 may run any operating system 816, such as any of the versions of the Microsoft® Windows® operating systems, the different releases of the Unix and Linux operating systems, any version of the MacOS® for Macintosh computers, any embedded operating system, any real-time operating system, any open source operating system, any proprietary operating system, any operating systems for mobile computing devices, or any other operating system capable of running on the computing device and performing the operations described herein. In exemplary embodiments, the operating system 816 may be run in native mode or emulated mode. In an exemplary embodiment, the operating system 816 may be run on one or more cloud machine instances.

Figure 9:
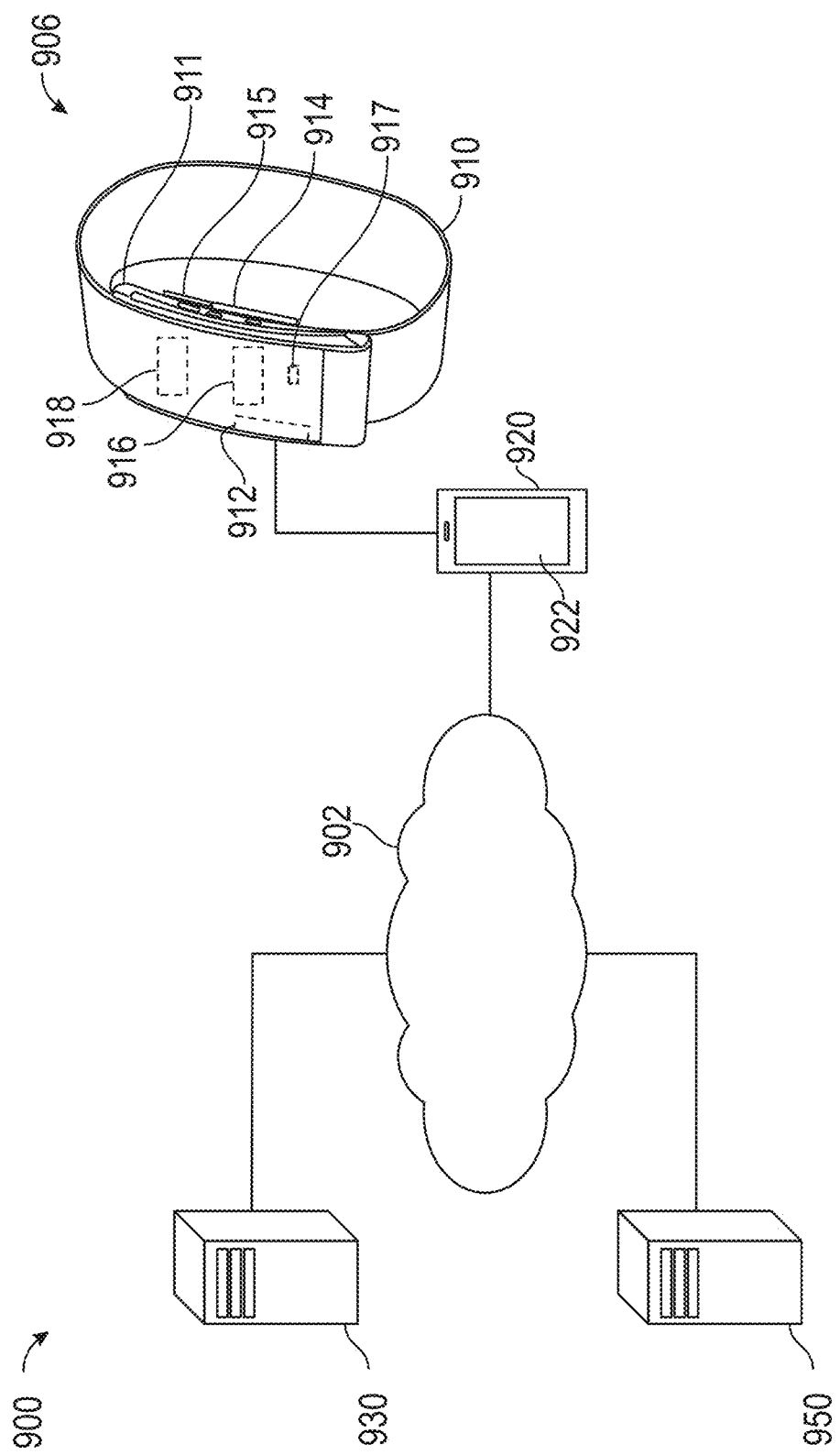
FIG. 9 illustrates a physiological monitoring system.

FIG. 9 illustrates a physiological monitoring system. More specifically, FIG. 9 illustrates a physiological monitoring system 900 that may be used with any of the methods or devices described herein. In general, the system 900 may include a physiological monitor 906, a user device 920, a remote server 930 with a remote data processing resource (such as any of the processors or processing resources described herein), and one or more other resources 950, all of which may be interconnected through a data network 902.

The data network 902 may be any of the data networks described herein. For example, the data network 902 may be any network(s) or internetwork(s) suitable for communicating data and information among participants in the system 900. This may include public networks such as the Internet, private networks, telecommunications networks such as the Public Switched Telephone Network or cellular networks using third generation (e.g., 3G or IMT-900), fourth generation (e.g., LTE (E-UTRA) or WiMAX-Advanced (IEEE 802.16m)), fifth generation (e.g., 5G), and/or other technologies, as well as any of a variety of corporate area or local area networks and other switches, routers, hubs, gateways, and the like that might be used to carry data among participants in the system 900. This may also include local or short range communications networks suitable, e.g., for coupling the physiological monitor 906 to the user device 920, or otherwise communicating with local resources.

The physiological monitor 906 may, in general, be any physiological monitoring device, such as any of the wearable monitors or other monitoring devices described herein. Thus, the physiological monitor 906 may generally be shaped and sized to be worn on a wrist or other body location and retained in a desired orientation relative to the appendage with a strap 910 or other attachment mechanism. The physiological monitor 906 may include a wearable housing 911, a network interface 912, one or more sensors 914, one or more light sources 915, a processor 916, a haptic device 917 (and/or any other type of component suitable for providing haptic or other sensory alerts to a user), a memory 918, and a wearable strap 910 for retaining the physiological monitor 906 in a desired location on a user.

In general, the physiological monitor 906 may include a wearable physiological monitor configured to acquire heart rate data and/or other physiological data from a wearer. More specifically, the wearable housing 911 of the physiological monitor 906 may be configured such that a user can acquire heart rate data and/or other physiological data from the user in a substantially continuous manner. The wearable housing 911 may be configured for cooperation with a strap 910 or the like, e.g., for engagement with an appendage of a user.

The network interface 912 may be configured to coupled one or more participants of the system 900 in a communicating relationship, e.g., with the remote server 930, either directly, e.g., through a cellular data connection or the like, or indirectly through a short range wireless communications channel coupling the physiological monitor 906 locally to a wireless access point, router, computer, laptop, tablet, cellular phone, or other device that can relay data from the physiological monitor 906 to the remote server 930 as necessary or helpful for acquiring and processing data.

The one or more sensors 914 may include any of the sensors described herein, or any other sensors suitable for physiological monitoring. By way of example and not limitation, the one or more sensors 914 may include one or more of a light source, an optical sensor, an accelerometer, a gyroscope, a temperature sensor, a galvanic skin response sensor, a capacitive sensor, a resistive sensor, an environmental sensor (e.g., for measuring ambient temperature, humidity, lighting, and the like), a geolocation sensor, a temporal sensor, an electrodermal activity sensor, and the like. The one or more sensors 914 may be disposed in the wearable housing 911, or otherwise positioned and configured for capture of data for physiological monitoring of a user. In one aspect, the one or more sensors 914 include a light detector configured to provide data to the processor 916 for calculating a heart rate variability. The one or more sensors 914 may also or instead include an accelerometer configured to provide data to the processor 916, e.g., for detecting activities such as a sleep state, a resting state, a waking event, exercise, and/or other user activity. In an implementation, the one or more sensors 914 measure a galvanic skin response of the user.

The processor 916 and memory 918 may be any of the processors and memories described herein, and may be suitable for deployment in a physiological monitoring device. In one aspect, the memory 918 may store physiological data obtained by monitoring a user with the one or more sensors 914. The processor 916 may be configured to obtain heart rate data from the user based on the data from the sensors 914. The processor 916 may be further configured to assist in a determination of a condition of the user, such as whether the user has an infection or other condition of interest as described herein.

The one or more light sources 915 may be coupled to the wearable housing 911 and controlled by the processor 916. At least one of the light sources 915 may be directed toward the skin of a user's appendage. Light from the light source 915 may be detected by the one or more sensors 914.

The system 900 may further include a remote data processing resource executing on a remote server 930. The remote data processing resource may be any of the processors described herein, and may be configured to receive data transmitted from the memory 918 of the physiological monitor 906, and to process the data to detect or infer physiological signals of interest such as heart rate, heart rate variability, respiratory rate, pulse oxygen, blood pressure, and so forth. The remote server 930 may also or instead evaluate a condition of the user such as a recovery state, sleep quality, daily activity strain, and any health conditions that might be detected based on such data.

The system 900 may also include one or more user devices 920, which may work together with the physiological monitor 906, e.g., to provide a display for user data and analysis, and/or to provide a communications bridge from the network interface 912 of the physiological monitor 906 to the data network 902 and the remote server 930. For example, physiological monitor 906 may communicate locally with a user device 920, such as a smartphone of a user, via short-range communications, e.g., Bluetooth, or the like, e.g., for the exchange of data between the physiological monitor 906 and the user device 920, and the user device 920 may communicate with the remote server 930 via the data network 902. Computationally intensive processing, such as infection monitoring, may be performed at the remote server 930, which may have greater memory capabilities and processing power than the physiological monitor 906 that acquires the data.

The user device 920 may include any computing device as described herein, including without limitation a smartphone, a desktop computer, a laptop computer, a network computer, a tablet, a mobile device, a portable digital assistant, a cellular phone, a portable media or entertainment device, and so on. The user device 920 may provide a user interface 922 for access to data and analysis by a user, and/or to control operation of the physiological monitor 906. The user interface 922 may be maintained by a locally-executing application on the user device 920, or the user interface 922 may be remotely served and presented on the user device 920, e.g., from the remote server 930 or the one or more other resources 950.

In general, the remote server 930 may include data storage, a network interface, and/or other processing circuitry. The remote server 930 may process data from the physiological monitor 906 and perform infection monitoring/analyses or any of the other analyses described herein, and may host a user interface for remote access to this data, e.g., from the user device 920. The remote server 930 may include a web server or other programmatic front end that facilitates web-based access by the user devices 920 or the physiological monitor 906 to the capabilities of the remote server 930 or other components of the system 900.

The other resources 950 may include any resources that can be usefully employed in the devices, systems, and methods as described herein. For example, these other resources 950 may include without limitation other data networks, human actors (e.g., programmers, researchers, annotators, editors, analysts, and so forth), sensors (e.g., audio or visual sensors), data mining tools, computational tools, data monitoring tools, algorithms, and so forth. The other resources 950 may also or instead include any other software or hardware resources that may be usefully employed in the networked applications as contemplated herein. For example, the other resources 950 may include payment processing servers or platforms used to authorize payment for access, content, or option/feature purchases, or otherwise. In another aspect, the other resources 950 may include certificate servers or other security resources for third-party verification of identity, encryption or decryption of data, and so forth. In another aspect, the other resources 950 may include a desktop computer or the like co-located (e.g., on the same local area network with, or directly coupled to through a serial or USB cable) with a user device 920, wearable strap 910, or remote server 930. In this case, the other resources 950 may provide supplemental functions for components of the system 900.

The other resources 950 may also or instead include one or more web servers that provide web-based access to and from any of the other participants in the system 900. While depicted as a separate network entity, it will be readily appreciated that the other resources 950 (e.g., a web server) may also or instead be logically and/or physically associated with one of the other devices described herein, and may for example, include or provide a user interface 922 for web access to a remote server 930 or a database in a manner that permits user interaction through the data network 902, e.g., from the physiological monitor 906 or the user device 920, with processing and data resources of the remote server 930.

Figure 10:
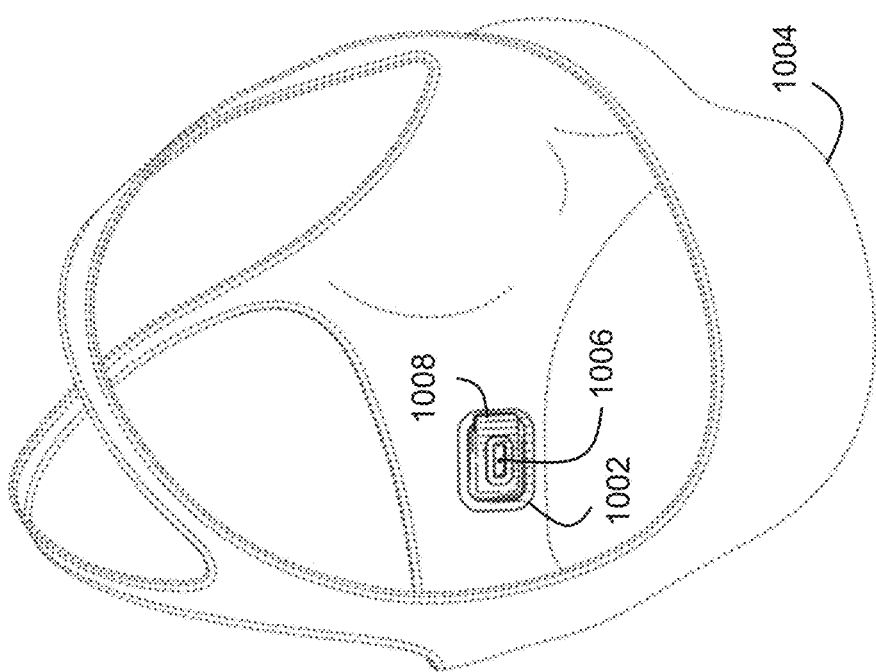
FIG. 10 shows a modular physiological monitoring system.

FIG. 10 shows a modular physiological monitoring system. In general, a pocket 1002 for a monitoring device, such as any of the sensing devices described herein, may be integrated into an article of clothing 1004. The pocket 1002 may be adapted for use with a removable and replaceable physiological monitoring device or the like, and may be configured to secure the device in a desired position, e.g., for monitoring during physical activity, while facilitating removal and replacement of the device as needed.

Integration of a wearable physiological monitor with a garment, as distinguished from a wristband, can provide numerous advantages. Wristbands (or ankle bands or the like) are typically constrained to certain positions and orientations on specific body parts and may often be inconvenient to wear or remove when a user is engaged in certain activities. For example, a user engaged in boxing may be unable to access a wrist-worn device while wearing boxing gloves. A user may also or instead wish to free up space on ankles or wrists for aesthetic reasons (e.g., to wear a bracelet or other fashion accessory) or functional reasons (e.g., to wear a watch or other wrist-worn device) from time to time, or to otherwise conceal a physiological monitor for some period of time. Despite these advantages, alternative locations present numerous challenges including providing stable positioning, ensuring adequate contact force for high quality monitoring, and so forth. The garment-based pockets described herein advantageously address these challenges to support modular, garment-based physiological monitoring while also providing a useful pathway for users to migrate monitoring devices as needed from a wrist to a concealed or otherwise more convenient location.

It will be understood that the pocket 1002 may be structurally configured for receiving a monitoring device therein, e.g., with only a predetermined portion of the monitoring device, a sensing region 1006, exposed through an opening (see the opening 1211 in FIG. 12) that provides a physical window for direct physical contact between a monitoring device and a user's body in a manner that facilitates physiological sensing. FIG. 10 shows the pocket 1002 with a monitoring device disposed therein, and the sensing region 1006 exposed through the opening 1211 so that the monitoring device can contact a user's skin in order to capture a physiological signal from a corresponding location on a wearer of the article of clothing 1004. In some embodiments, a housing of the monitoring device may be configured as a wearable bracelet with a detachable strap in order to facilitate movement of the monitoring device between a wrist of the user and the garment as necessary or desired. The monitoring device may include any of the devices described herein, such as a wearable physiological monitoring device that uses photoplethysmography (PPG), or more generally, any device configured to monitor physiological data that might usefully be moved between a wrist and another body location such as the torso, arm, leg, etc.

The article of clothing 1004 may be any article of clothing that might be worn by a user including athletic wear such as an athletic undergarment (e.g., a sports bra, underpants, compression garment, and so forth), as well as any other garment that can retain a monitoring device in contact with a user in a manner that permits sensing of physiological signals, e.g., as described herein. For example, where shorts or a t-shirt include skin-tight regions such as a waist band or sleeves, the pocket 1002 may usefully be positioned at such a location. Other articles of clothing or accessories may also or instead be used, such as a wrist band, a sock, a shoe, a bicep band, a calf band, a chest band, a headband, pants, leggings, an undershirt, a sports pad, a helmet, a hat, and so forth.

The pocket 1002 may generally secure the monitoring device in the article of clothing 1004 in a position to permit sensing and capture of physiological signals from a wearer of the article of clothing 1004. In one aspect, the position may advantageously be located where physiological measurements can be easily captured (e.g., the wrist or bicep), and/or at a location where the article of clothing 1004 can impart sufficient normal forces on the monitoring device in the pocket 1002 to engage the monitoring device for physiological monitoring. This may include a location such as a waist band of underpants or an elastic torso band on a sports bra. The position of the pocket 1002 may also or instead be located where the monitoring device would not interfere with or otherwise impede movement of a wearer and/or a physical activity of the wearer. For example, the pocket 1002 may be positioned on the wearer's chest while the wearing is cycling. In some embodiments, the pocket 1002 may be a permanent fixture on the article of clothing 1004. In such embodiments, the pocket 1002 may be designed with materials durable enough to withstand a wide range of wash cycles and weather conditions without losing its original structure. Alternatively, the pocket 1002 may be removeable from the article of clothing 1004, and retained in a removable and replaceably manner on the article of clothing using an attachment mechanism such hook-and-loop fasteners, adhesive tapes, zippers, snaps, buckles, cuff links, and the like.

An access port 1008 for the pocket 1002 may facilitate removal of the monitoring device from, and replacement of the monitoring device to, the pocket 1002. The access port 1008 may be positioned along an edge of the pocket 1002 and may be releasably sealed with a seal such as a zipper, snaps, hook-and-loop fasteners, or the like. In general, the access port 1008 may be shaped and sized to receive the monitoring device. The seal of the access port 1008 may advantageously seal the pocket 1002 in a manner that applies a force on the monitoring device to urge the monitoring device into the pocket 1002 and to create tension and frictional engagement within the pocket 1002 around the monitoring device so that the monitoring device retains a location within the garment (and as a result, relative to the user's body). The seal may, for example, urge the monitoring device into the pocket to induce an elastic deformation within material of the pocket 1002 and securely engage the monitoring device within the pocket 1002.

Figure 11:
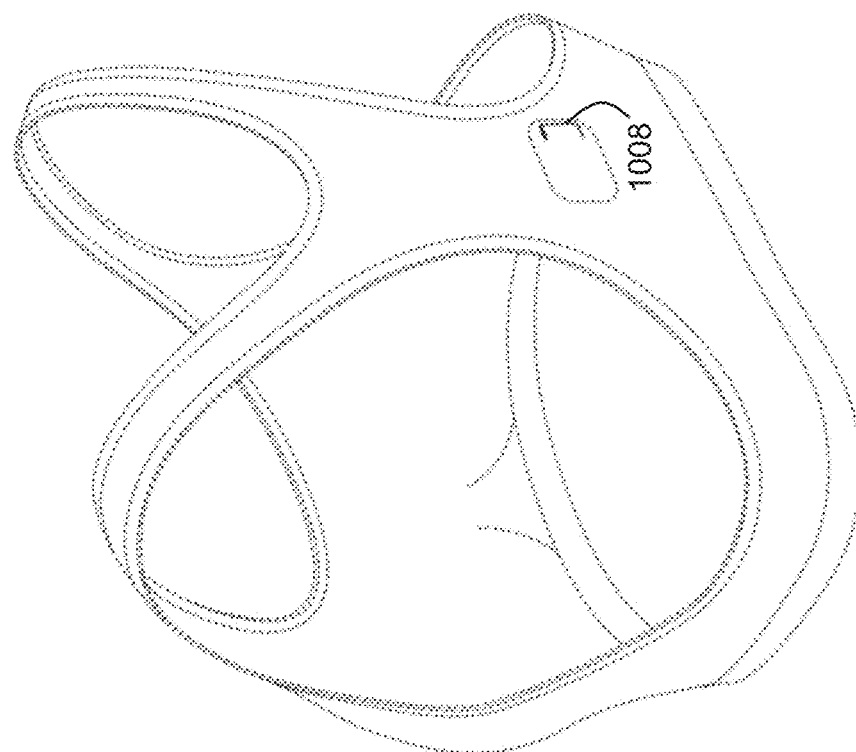
FIG. 11 shows a modular physiological monitoring system.

In one aspect, the access port 1008 is accessible through a first surface on an interior of the article of clothing 1004 when the article of clothing 1004 is in use (e.g., on a wearer)—this configuration is shown for example in FIG. 10. This configuration may allow for a user to conceal the pocket 1002 in situations where inconspicuousness is valued. In another aspect, the access port 1008 is accessible through a second surface on an exterior of the article of clothing 1004 facing away from a wearer when the article of clothing 1004 is in use—this configuration is shown in FIG. 11. This placement facilitates user access without requiring removal of the article of clothing 1004, although it may produce visible artifacts on other garments worn over the article of clothing 1004. In another aspect, an access port 1008 may be included on both the first surface and the second surface of the article of clothing 1004, so as to allow easy swapping of the monitoring device from the inside or outside of the article of clothing 1004.

Figure 12:
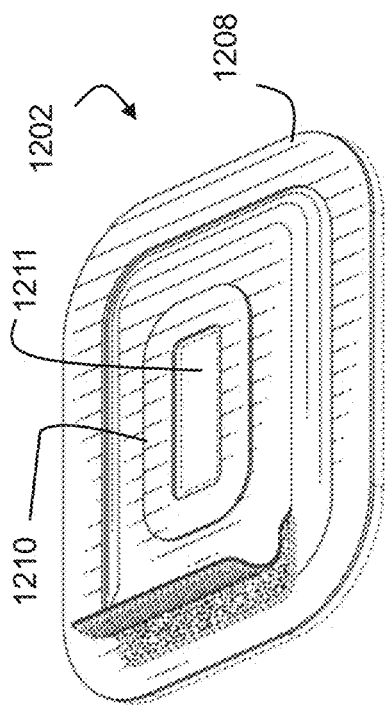
FIG. 12 shows a pocket for a monitoring device.

FIG. 12 shows a pocket 1202 for a monitoring device, such as any of the pockets described herein, except where specifically noted otherwise. The pocket 1202 may be included on, in, or otherwise engaged with an article of clothing as shown, for example, in FIG. 10.

A retaining ring 1208 may bound an interior surface of the pocket 1202. The retaining ring 1208 may be shaped to surround the perimeter of the monitoring device and may be raised above a surface of the article of clothing to inhibit lateral movement of a bottom surface of the monitoring device along the surface of the article of clothing when the monitoring device is placed for use in the pocket 1202. That is, the retaining ring 1208 may form a wall around the monitoring device, when placed for use, to resist lateral movement. The retaining ring 1208 may, for example, be formed of a material such as neoprene or the like, and may have a thickness of about 0.5 to about 1.5 millimeters or more to provide a suitable sidewall for laterally retaining the monitoring device.

A window 1210 may be positioned along an interior region of the article of clothing (e.g., the area contacting a wearer's skin) and facing a target surface in order to expose the sensor(s) of a monitoring device to the target surface through an opening 1211 when the monitoring device is placed for use in the pocket 1202 and an accompanying garment is being worn. In this context, it will be understood that the "window" refers to the material bounding the window, and the "opening" refers to the void space bounded by the window so that a monitoring device can directly contact a user through the window. The window 1210 may be encircled by the retaining ring 1208 and protrude away from the interior surface bounded by retaining ring 1208. The window 1210 may be formed of a relatively inelastic material so that the window 1210 maintains a shape to expose the sensor(s) of the monitoring device during use. The window 1210 may also be sized smaller than a projection of the monitoring device (normal to a plane of the window) when the monitoring device is placed for use in order to prevent the window 1210 from deforming and permitting the monitoring device to physically pass through the window 1210 and out of the pocket 1202 during use. In this context, the phrase "relatively inelastic" should be understood to mean generally less deformable or stretchable than other materials such as the material for a garment, and/or sufficiently inelastic to prevent deformation that permits the monitoring device to pass through the window 1210 during use. Thus, in one aspect, the window 1210 may be formed of a sheet material that is substantially inelastic relative to a material of an interior of the pocket 1202, and/or a material of the article of clothing to which the pocket 1202 is attached. The sheet material of the window 1210 may include any combination of elastomeric or other materials suitable for retaining the monitoring device in this manner. The window 1210 may thus generally include a border region (e.g., having the structural properties described above) defining an opening 1211 to expose the sensing region 1006 of the monitoring device during use. The opening 1211 may be completely open in some aspects, and in other aspects, the opening 1211 may be covered by a material through which the sensing region 1006 can still function (e.g., a clear material allowing light to pass through such as glass or plastic), or may be partially covered by an open mesh or the like that permits direct contact between the monitoring device and the skin while generally retaining the sensing region of the monitoring device within the pocket.

While the window 1210 may generally provide an opening for direct contact between sensors and a target surface such as the skin, and the foregoing description emphasizes this type of window as useful for photoplethysmography or similar optical sensing, it will be understood that the window may more generally be any arrangement that permits functional engagement between one or more sensors and the target surface. Thus, for example, where the sensors are optical sensors, the opening in the window 1210 may include or be filled with an optically clear material such as a sheet of plastic or the like, or any other material that otherwise fills the window while permitting optical sensing of a surface on one side of the window 1210 by a sensor system on the other side of the window 1210. Similarly, where the sensors include electrical sensors such as muscle activity sensors, the window 1210 may border a conductive pad or the like that permits a detection of electrical signals originating on one side of the window 1210 by sensors on the other side of the window 1210 (and/or the sourcing of electrical signals from one side of the window 1210 into a target surface on the other side of the window 1210, e.g., where the sensor system uses an electrical stimulus for sensing or imaging). As another example, where the sensor system includes acoustic sensing systems, the window 1210 may border a material that mechanically couples the sensor system on one side of the window 1210 with a target surface on the other side of the window 1210. In this latter example, the mechanical coupling is preferably with a material and in a configuration that mitigates or prevents signal attenuation through the window 1210, i.e., that transmits mechanical signals through the window 1210 with minimal loss. More generally, the window 1210 may provide any suitable medium for functionally engaging a sensor system on one side of the window 1210 with a target surface on the other side of the window 1210.

Figure 13:
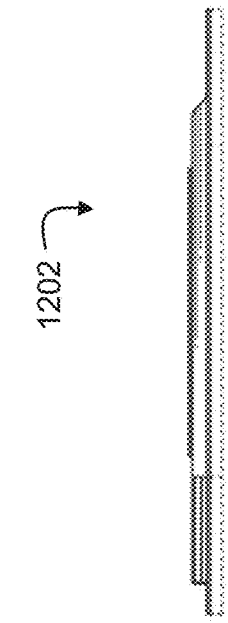
FIG. 13 is a side view of the pocket of FIG. 12 without a monitoring device placed therein.

FIG. 13 is a side view of the pocket 1202 of FIG. 12 without a monitoring device placed therein. In the absence of a monitoring device or other insert, the pocket 1202 may reside in a collapsed state such the thickness of the pocket 1202 is 10 mm or less, e.g., as an elastic fabric coupling the retaining ring 1208 to the window 1210 relaxes and draws the window against a substrate for the pocket 1202. The window 1210 may lie flat against an interior surface of the pocket 1202 such that the window 1210 lies on a plane of the access port 1008. This relatively flat configuration may improve user comfort when wearing the garment without a monitoring device, e.g., in a manner similar to other garments that include no such pockets 1202. That is, the pocket 1202 in a flattened state may be structurally configured to be relatively inconspicuous or unnoticeable, and/or to not interfere with the comfort and/or movement of the wearer of a garment that includes the pocket 1202.

Figure 14:
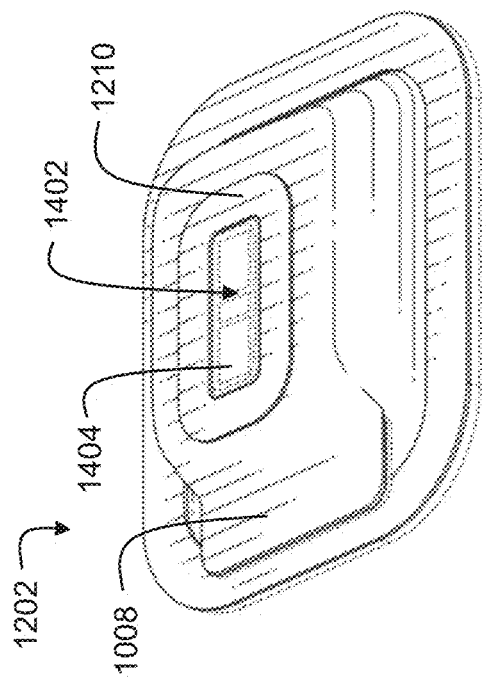
FIG. 14 is a perspective view of the pocket of FIG. 12 with a monitoring device placed therein.

FIG. 14 is a perspective view of the pocket 1202 of FIG. 12 with a monitoring device placed therein. In general, an elastic material of the pocket 1202 may expand in thickness to accommodate the monitoring device. After expanding, the pocket 1202 may, for example, have a maximum thickness of about 20 mm or less. When the pocket 1202 is in an occupied state, the window 1210 may lie on a plane parallel to but separate from a plane of the access port 1008. For example, the window 1210 may be at a vertical extremity of the pocket 1202 (in the upward direction, in FIG. 15), e.g., to facilitate placement of sensors for the monitoring device in contact with a user's skin through the window 1210, whereas the access port 1008 may be at a lower vertical position, and may more specifically be placed at or near a height of the retaining ring 1208 or an underlying substrate such as the fabric or elastic band of a garment. A top surface 1402 of the monitoring device may be at or above a height of the window 1210. The top surface 1402 may contain one or more sensors 1404 (e.g., one or more photoplethysmography sensors) exposed through an opening in the window 1210 and configured to monitor physiological data at a target surface such as a wearer's skin.

Figure 15:
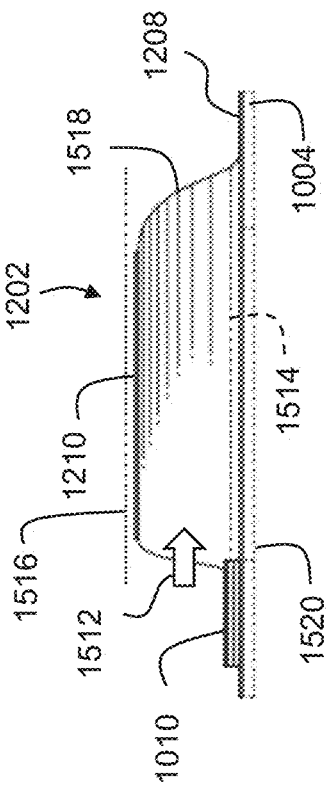
FIG. 15 is a side view of the pocket of FIG. 12 with a monitoring device placed therein.

FIG. 15 is a side view of the pocket 1202 of FIG. 12 with a monitoring device placed therein. As shown in FIG. 15, the retaining ring 1208 may rest near an article of clothing 1004 that provides a substrate for the pocket 1202, and the window 1210 may be displaced away from the article of clothing 1004 (and the retaining ring 1208, which may be affixed to the article of clothing 1004) when the monitoring device is inserted in the pocket 1202. The access port 1008 may generally urge the monitoring device into the pocket 1202 when closed, as indicated by an arrow 1512 so that the elastic materials of the pocket 1202 create tension retaining the monitoring device inside. A bottom surface 1514 of the monitoring device may rest on an interior surface 1520 of the pocket 1202 surrounded by the retaining ring 1208. The sensing region 1006 of the monitoring device may face towards a target surface 1516, with the sensing region 1006 in direct contact with the target surface 1516 when the monitoring device is in the pocket 1202 and the garment is worn by a user. The target surface 1516 may be a surface of any body part on which physiological data can be measured, such as a wrist, an arm, a leg, chest, torso, or the like.

The retaining ring 1208 and the window 1210 may be coupled by a wall 1518 with a relatively high elasticity in order to elastically yield and permit separation of the window 1210 from the retaining ring 1208 to receive the monitoring device, as illustrated in FIG. 15. The wall 1518 may stretch to extend from a plane of the retaining ring 1208 to a plane of the window 1210 when a monitoring device is placed in the pocket 1202. In one aspect, the wall 1518 may be formed of a nylon blend woven material or other elastic sheet material or the like. The monitoring device may be inserted into the pocket 1202 within an interior cavity of the pocket 1202 formed by the wall 1518 and other surfaces.

The interior surface 1520 of the pocket 1202 (farthest from the target surface) may be bounded by the retaining ring 1208, which is preferably formed of a material with a lower elasticity than the material of the wall 1518 so that the wall 1518 yields more than the retaining ring 1208 and underlying sheet materials when a device is placed into the pocket 1202. The interior surface 1520 may, for example, be formed of neoprene or the like, and may be about 1 mm thick or more. In this configuration, when the access port 1008 is closed, the wall 1518 can yield elastically about the perimeter of the monitoring device to urge the monitoring device away from the interior surface 1520 and toward the window 1210 and the target surface for the sensing region 1006. More generally, the relatively elastic and inelastic surfaces of the pocket 1202 may be arranged to impart a normal force on a monitoring device away from a plane of the underlying garment and into a target surface such as a wearer's skin. This more generally causes the monitoring device to protrude from the article of clothing into a target surface for improved engagement of the sensing region 1006 with the target surface when the article of clothing is worn. As used in this context to describe the material of the wall 1518, the phrase "relatively high elasticity" describes the generally higher elasticity of the material of the wall 1518, as compared to the interior surface 1520 and/or the window 1210, that urges the monitoring device to protrude from the article of clothing 1004 to engage the target surface as described herein. While specific elasticity characteristics of various fabrics and other sheet materials used in garments are well known, the precise elasticity of each component is less important than a generally higher elasticity of the wall 1518 that encourages the sensing region 1006 of a monitoring device to extend in this manner.

A high-friction surface such as a tackified surface, low durometer polymer, or the like, may be applied to the interior surface 1520 of the pocket 1202 where the pocket 1202 is bounded by the retaining ring 1208 to further inhibit lateral movement of the monitoring device along the interior surface 1520 when the monitoring device is placed for use in the pocket 1202. In one aspect, the material of the interior surface 1520 may include a high friction surface facing an interior of the pocket 1202, where the high friction surface has a greater coefficient of sliding friction than other interior surfaces of the pocket 1202. In another aspect, the interior surface 1520 may include a high-friction surface treatment having a greater coefficient of sliding friction than other interior surfaces of the pocket 1202 to inhibit lateral movement of a device within the pocket 1202 along the first surface. In another aspect, the monitoring device may have a high-friction surface treatment.

According to the foregoing, there is described herein a pocket for securing a modular device within an article of clothing. The pocket may include: a first surface formed of a first sheet material having a first elasticity and providing a substrate for a monitoring device when inserted into the pocket; a retaining ring formed of a second material, the retaining ring forming a raised perimeter to inhibit movement of a device in the pocket along the first surface; a wall formed of a third material having a higher elasticity than the first sheet material, the wall including an opening positioned to expose a sensor of a device when placed for use in the pocket, and the third material selected to elastically yield to the device when inserted into the pocket; a window formed of a fourth material positioned around the opening, the fourth material having a lower elasticity than the third material of the wall; and an access port configured to receive the device into the pocket when opened, and configured to secure the device within the pocket against an elastic force of the wall when closed.

FIG. 16 illustrates a layer-based fabrication process for a pocket. In one aspect, the pocket may be fabricated from one or more layers 1600 of sheet material. This advantageously permits fabrication of the pocket in a layered manufacturing process independent of fabrication of the clothing (unless the access port passes through the clothing), after which the pocket may be adhered to the clothing in a desired location using a commercial adhesive or the like. In some embodiments, the pocket may be fabricated from eight or more layers. The layers 1600 may include the following, which may in one aspect be assembled in order to fabricate the pocket. The layers 1600 may include a fixing ring layer 1602 to serve as the retaining ring described above. The layers 1600 may include a hook-and-loop fastener layer 1604 for use in securing the access port. The layers 1600 may include a lock ring layer 1606 to serve as the window described above, or more particularly, the frame/perimeter of a window as described herein. The layers 1600 may include an inside layer 1608 to provide, inter alia, the elastic sidewalls described above. The layers 1600 may include an open ended glue layer 1610 for securing a portion of the retaining ring to a substrate or to the inside layer 1608. The layers 1600 may include an adhesive 1612 for securing a nonstick material 1614 such as a Griptech material to a base layer 1616 of the pocket. The sheet material for the layers 1600 may include one or more of Bemis STR4000, Velcro, Nylon body fabric, 1 mm Neoprene, Bemis Griptech ET3150033, and Bemis 3415. Intermediate layers may be adhered to one another using industrial sheet adhesives such as Bemis 3415 Sewfree Tape available from Bemis Associates, Inc., or any other soft elastomeric adhesive film, hot melt glue, or the like. Additionally, the high-friction surfaces described above may be applied as additional layers in a manufacturing process where helpful. For example, the high-friction surfaces may be formed of Bemis Griptech ET3150033 or any other polymer, tackifier, or the like providing a high-grip or high-coefficient-of-friction surface.

An assembly process using these adhesives and sheet materials advantageously permits automated or manual manufacturing without machine stitching or other time-intensive and labor-intensive processes requiring specialized machinery.

FIG. 17 illustrates a physiological monitoring device 1702, such as any of the monitoring devices described herein. The monitoring device 1702 may include a housing 1704 providing a protective enclosure (e.g., waterproof enclosure) for a battery 1706 of the monitoring device 1702 and sensing circuitry 1708 powered by the battery 1706. The housing 1704 may include a pair of functional guide surfaces 1710 on opposing sides of the exterior thereof. Each of the functional guide surfaces 1710 may form a curved draw path 1712 for attaching and detaching a wireless battery, along with a detent 1714 (which may also be curved) for retaining the wireless battery in a position to wirelessly couple to and provide power for the battery 1706 in the housing 1704. Alternatively, the detent 1714 may be a projection, with the wireless battery having a corresponding detent for receiving the projection. This removable and replaceably wireless batter supports continuous physiological monitoring while the wireless battery recharges the battery 1706, without the need to remove the monitoring device 1702 from a user. Instead, the wireless battery may be easily removed from the monitoring device 1702 and replaced without hindering a user engaged in a variety of activities. The curved draw path 1712 may have a radius of curvature of about 227 millimeters, or more generally between about 200 millimeters to about 250 millimeters, or still more generally between about 150 millimeters and about 300 millimeters. This curvature supports good fit to a human wrist, while inhibiting displacement of the battery under high speed linear displacement of the housing 1704. Alternatively, the draw path 1712 may be a straight line running on opposing sides of the housing 1704.

In one aspect, the housing 1704 may include a waterproof enclosure. As described herein, features that are "waterproof" or "substantially waterproof" may be engineered to prevent ingress of water, e.g., according to any suitable national or international standard for degrees of protection provided by enclosures such as the International Protection Code or IP Code, for short, or any other objective standard or the like. In one aspect, the housing 1704 (or any related components or enclosures) may conform to IPX7 of the International Protection Code, which specifies no ingress of water in harmful quantities during immersion in water having a depth of at least one meter for at least thirty minutes. This facilitates use of the housing 1704, e.g., while swimming. Other more or less rigorous ingress/protection standards may also or instead be used, and may be appropriate for high diving or deep water activities. In some embodiments, the housing 1704 may be formed of water-resistant materials such as rubber, nylon, polytetrafluoroethylene, or the like. The housing 1704 may also or instead be lined with a sealant for further waterproofing.

FIG. 18 illustrates a wireless battery 1810 coupled to a physiological monitoring device 1802. In general, the wireless battery 1810 may be a wireless recharging battery (also referred to herein simply as a "recharging battery") removably and replaceably coupled to the physiological monitoring device 1802 in a manner that securely retains the wireless recharging battery in a precise location relative to a corresponding wireless power interface of the monitoring device 1802, while facilitating intuitive and easy removal and replacement of the wireless recharging battery by a user. In this manner, the monitoring device 1802 may continuously monitor physiological data of a user with minimal effort needed from the user to keep the battery (i.e., the internal battery) of the monitoring device 1802 charged. In general, the wireless battery 1810 may include a battery with sufficient power to recharge the battery of the monitoring device 1802, along with wireless power transfer circuitry providing a wireless power interface for wirelessly transferring the stored energy from the wireless battery 1810 to the monitoring device 1802. The wireless battery 1810 may straddle a head portion of the monitoring device 1802 while recharging the battery of the monitoring device 1802. In some embodiments, the wireless battery 1810 may be able to power the monitoring device 1802 on its own without the battery of the monitoring device 1802. A housing 1812 for the wireless battery 1810 may usefully provide a substantially waterproof enclosure meeting, e.g., the IPX7 standard for ingress protection described above, or any other suitable standard or the like for waterproofing. The housing 1812 may be formed of a polycarbonate blend, or any other polymer and/or other material(s) that are weatherproof/waterproof and suitably strong for removably and replaceably engaging with a monitoring device as described herein.

In one aspect, a wireless power interface may include a wireless power transmitter 1822 in the wireless battery 1810 and a wireless power receiver 1824 in the monitoring device 1802. By curving these otherwise planar structures along the radius of curvature of the monitoring device, the transmitter 1822 and the receiver 1824 can advantageously be placed closer together along a physical boundary between the wireless battery 1810 and the monitoring device 1802, thus supporting more efficient wireless power transfer (illustrated conceptually as arrows 1826) through the intervening space, e.g., of the housings and other hardware of the two components when the two components are coupled for charging.

The wireless battery 1810 may generally be configured for bidirectional mechanical and electromagnetic coupling to the monitoring device 1802. For example, the wireless battery 1810 may include a pair of wings (described in more detail below) that are substantially symmetrical about an axis normal to the draw path to facilitate bidirectional coupling of the recharging battery to the monitoring device 1802. The wireless battery 1810 may also be symmetrical about the normal axis. In this context, the draw path is the physical path that the wireless battery 1810 follows when engaging with the functional surfaces of the monitoring device 1802 to attach to or detach from the monitoring device 1802.

It should also be noted that wireless power transfer circuitry systems and methods are generally known in the art. The details of such circuitry and/or wireless power transfer interfaces vary according to the rate and total amount of power to be transferred, the form factor of the wireless interface, the size and expected distance between transceivers, and so forth. The details of such circuits are not described here, except to note that the techniques used herein advantageously enforce an accurate, consistent distance and orientation between a recharging battery and a monitoring device, thus permitting consistent alignment of transceivers and antennae, and correspondingly efficient wireless transfers of power, and advantageously support closer position of a wireless power transmitter and receiver by curving these devices to conform more closely to the physical surfaces of the housing for the wireless battery 1810 and the monitoring device 1802.

FIG. 19A illustrates a recharging battery 1902 aligned for coupling to a monitoring device, and FIG. 19B shows alternative views of the recharging battery 1902 aligned for coupling to the monitoring device. Specifically, FIGS. 19A-19B illustrate wings 1904 extending from a recharging battery 1902 for coupling the recharging battery 1902 to a monitoring device. The recharging battery 1902 may have two wings 1904 on opposing sides of the recharging battery 1902 that each flexibly yield to support engagement and disengagement with the monitoring device, although alternatively the recharging battery 1902 may have only one wing that flexes in this manner. The wings 1904 may be formed of a polycarbonate blend or any other material(s) of suitable strength for use as described herein. Each of the wings 1904 may have a curved flange 1906 shaped to guide the recharging battery 1902 along the curved draw path defined by the housing of the monitoring device by following a respective one of the functional guide surfaces. Further, each curved flange 1906 may be shaped to mate with a curved detent 1908 of the monitoring device to secure the recharging battery 1902 in a predetermined position relative to the monitoring device for wirelessly transferring power from a battery of the recharging battery 1902 to the battery of the monitoring device through a wireless power transfer circuit 1910. It will be understood that the recharging battery 1902 may also be wirelessly rechargeable, which permits removal of exterior metal contacts and the like along with accompanying improvements to water ingress protection. This advantageously permits use of the recharging battery 1902 to recharge the monitoring device under a greater range of conditions, e.g., in the rain, in the shower, while swimming, and so forth. The recharging battery 1902 may also or instead include a plug or other electromechanical port or the like for wired recharging.

The wireless power transfer circuitry 1910 may contain an antenna 1912 having a normal axis 1914. The antenna 1912 may be a planar antenna shaped and sized for non-contact power transfer. In another aspect, the antenna 1912 may have a three-dimensional surface shape conforming to a lateral surface of a right cylinder, which in turn may have a curvature corresponding to the radius of curvature of a surface of the monitoring device 1802 and/or the curved flanges 1906 of the monitoring device 1802. In this manner, the antenna 1912 may generally follow the shape of the draw path 1712 for coupling to a physiological monitoring device as described above, and more generally, the shape of exterior mating surfaces of the recharging battery 1920 and the monitoring device 1802 so that the antennae used to transfer power from the recharging battery 1920 to the monitoring device 1802 may be placed in closer proximity to one another. The normal axis 1914 of the antenna 1912 may be at or near a center of the antenna 1912, or in any other location where an antenna of the recharging battery lies parallel to an antenna of a monitoring device. The wings 1904 may extend from the housing parallel to the normal axis 1914. As described above, the monitoring device 1802 may have a second antenna with a curvature corresponding to the radius of curvature of the antenna of the recharging battery 1920, which permits closer placement of the surfaces of the two antennae for more efficient power transfer when the wireless battery 1810 is coupled to the monitoring device 1802.

Figure 20:
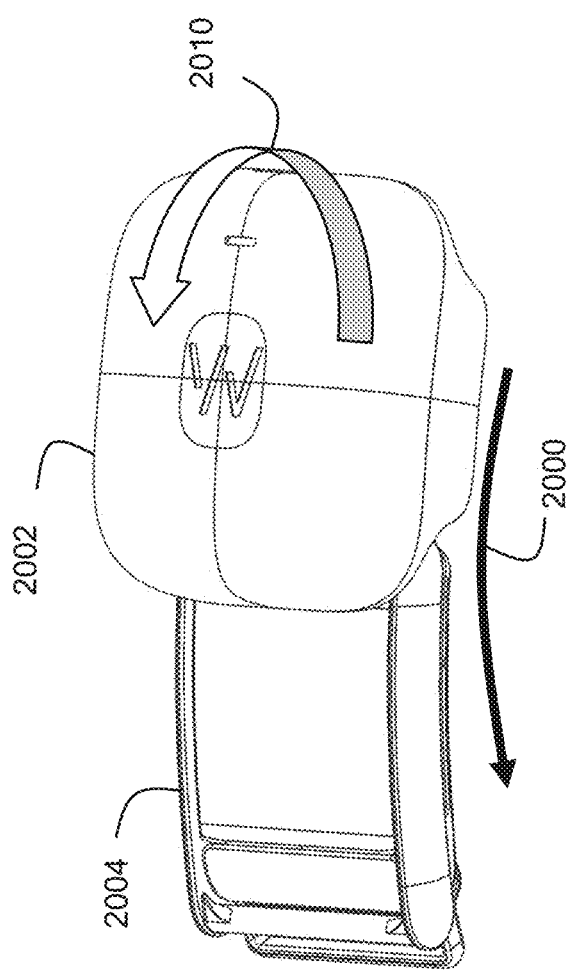
FIG. 20 illustrates a draw path for a wireless battery to slidably engage a monitoring device.

FIG. 20 illustrates a draw path 2000 for a wireless battery 2002 to slidably engage a monitoring device 2004. As noted above, the wireless battery 2002 may also or instead be attached in an opposite orientation, e.g., with the wireless battery 2002 rotated 180 degrees as shown by an arrow 2010. In this manner, a user may engage the wireless battery 2002 with the monitoring device 2004 without the need to determine a specific orientation of the wireless battery 2002. Further, although the wings 1904 and detents 1908 shown in FIG. 19 are intended to permit attachment of the wireless battery 2002 only from one side of the monitoring device 2004, the interface between these components may be adapted so that the wireless battery 2002 may also or instead be attached from an opposite end of the monitoring device 2004. That is, although the wireless battery 2002 is shown in this figure as being coupled to the monitoring device 2004 from its right side moving left as shown by the draw path 2000, in certain aspects, the wireless battery 2002 may also or instead be configured to couple to the monitoring device 2004 from its left side moving right, in a direction opposing the draw path 2000 as shown.

Figure 21:
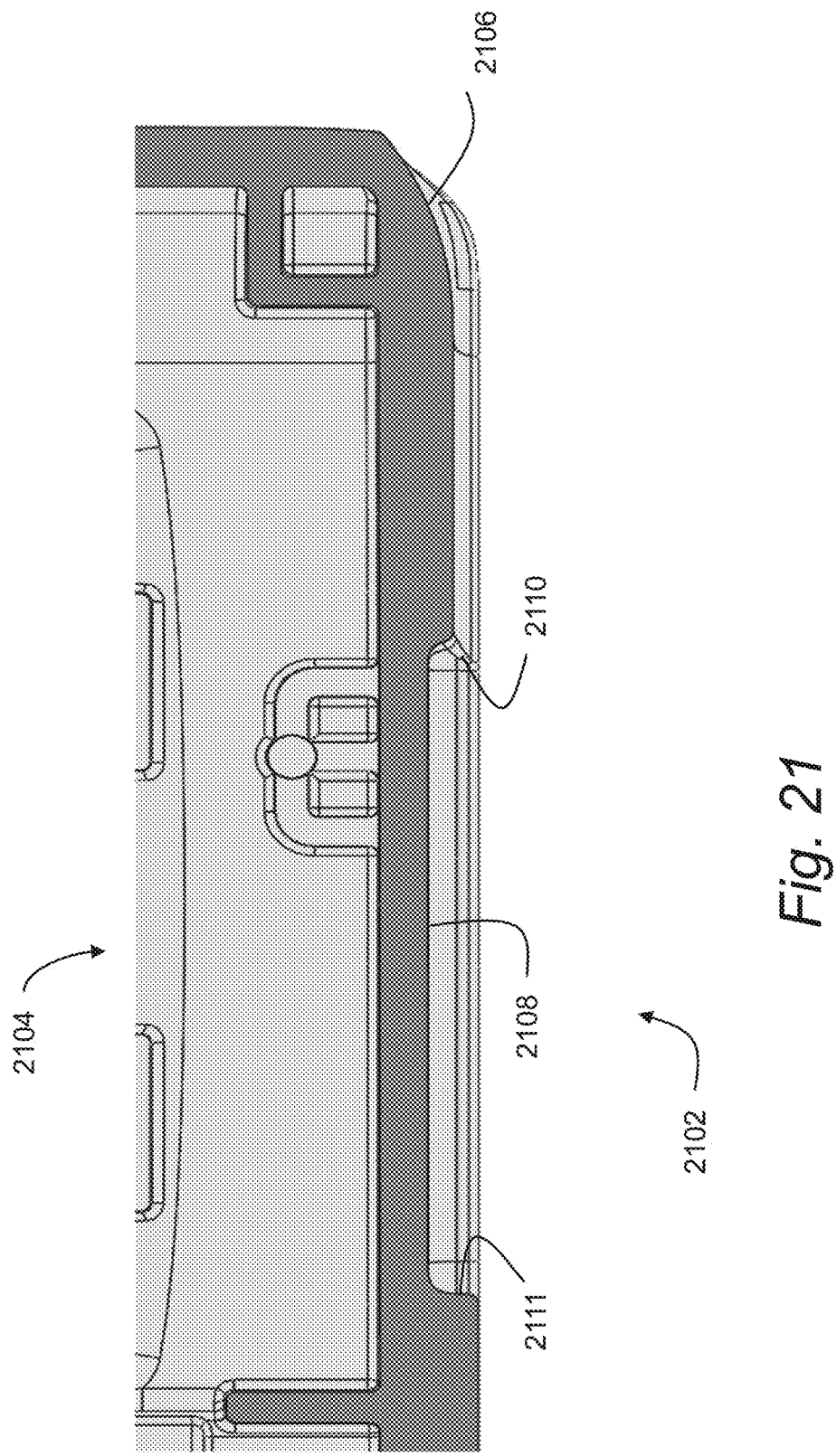
FIG. 21 is a top view of functional surfaces of a monitoring device that slidably engage a wireless battery.

FIG. 21 is a top view of functional surfaces 2102 of a monitoring device that slidably engage a wireless battery as described herein. In general, these functional surfaces 2102 may cooperate with the wings and flanges of the wireless battery described above, or any other similarly mechanical topological features, to impose a desired attachment and detachment force for the wireless battery along the draw path. The monitoring device may additionally have side rails 2104 surrounding the functional surfaces 2102 that help enforce the draw path. It will be understood that the functional surfaces 2102 depicted in FIG. 21 may advantageously be mirrored on an opposing side of the monitoring device for balanced, bidirectional operation, although this is not required.

In one aspect, the functional guide surfaces 2102 may include a ramp 2106 for progressively displacing a corresponding one of the wings of the recharging battery away from the monitoring device to receive the recharging battery as the recharging battery travels along the curved draw path. For example, the ramp 2106 may progressively displace one of the wings about 0.5 millimeters (in a direction away from the monitoring device), or more specifically, one of the curved flanges extending from one of the wings. In one aspect, each of the curved flanges may yield at least about 0.5 millimeters away from the monitoring device (and/or the opposing curved flange of the other wing) in response to an outward force of about 20 Newtons. By angling the ramp 2106 appropriately, this results in a maximum insertion force of about 8 Newtons for coupling the recharging battery to the monitoring device along the curved draw path, which facilitates relatively easy securement of the recharging battery with the monitoring device. More generally, the ramp 2106 and the wings may be designed to cooperatively generate a maximum insertion force of about 5 Newtons to about 15 Newtons. Other ranges of forces are instead possible.

It will be understood that the insertion force may generally vary as the recharging battery moves along the functional guide surfaces 2102 according to one or more of the speed of motion, an amount of surface contact between the recharging battery and the monitoring device, the slope of the ramp 2106, and so forth. As such, a nominal insertion force engineered for the system may vary during use, and may vary over time due to wear and strain. The maximum insertion force, or the maximum insertion force along the draw path, is used herein to describe the greatest expected insertion force during use of the devices. In some embodiments, the maximum insertion force may occur at the start of the draw path, to avoid unintentional attachment of the recharging battery to the monitoring device.

The functional guide surfaces 2102 may include a detent 2108 such as any of the curved detents or the like described above. In general, the detent 2108 may provide a recess or other similar mechanically keyed interface to receive a flange of the recharging battery and secure the recharging battery (against reverse displacement along the draw path to remove the recharging battery) at a location selected for wireless delivery of power from the recharging battery to the battery of the monitoring device.

The functional guide surfaces 2102 may include a second ramp 2110 at an endpoint of the detent 2108 that progressively displaces a corresponding one of the wings to release the recharging battery from the detent 2108 when removing the recharging battery along the curved draw path. In this respect, the functional guide surfaces 2102 may be shaped to create a maximum removal force for uncoupling the recharging battery from the monitoring device along the curved draw path of about 18 Newtons. In one aspect, the functional guide surfaces 2102 may create a maximum removal force for uncoupling the recharging battery from the monitoring device that is significantly greater than the insertion force in order to securely engage and retain the recharging battery once it is attached. This may generally include a maximum removal force along the curved draw path of about 10 Newtons to about 35 Newtons or any other force or range of forces that make it more difficult to remove the recharging battery than to attach the recharging battery. In this manner, the functional guide surfaces 2102 may ensure that the recharging battery is secured onto the monitoring device at a precise location.

The functional guide surfaces 2102 may also include a hard stop 2111 that prevents movement of the recharging battery along the draw path beyond the detents 2106 that receive the flanges of the recharging battery. The hard stop 2111 may be any protrusion large enough to prevent movement of the recharging battery beyond the detents 2106. In this manner, the functional guide surfaces 2102 may enforce an endpoint along the draw path where the flanges engage the detents 2106, which may be more specifically be selected to ensure good alignment of antennae between the recharging battery and the monitoring device as described herein.

In general, the flanges of the recharging battery and the functional surfaces 2102 of the monitoring device may cooperate to enforce a draw path and create desired insertion and removal forces for the recharging battery as described above. The side rails for the functional surfaces 2102, along with the mechanical properties of the wings of the recharging battery, may also cooperate to securely retain the recharging battery along the draw path, and prevent displacement off of the draw path. For example, the curved flanges may require at least 100 Newtons of outward force to separate the recharging battery from the functional guide surfaces 2102 in a direction off the curved draw path, or may more generally require a non-draw-path displacement force sufficient to securely enforces movement along the draw path during attachment and removal of the recharging battery, and/or to prevent displacement of the batter from the monitoring device during use.

According to the foregoing, in one aspect there is described herein removable and replaceable wireless recharging battery for use with a physiological monitoring device. The recharging battery may include a battery; wireless power transfer circuit including an antenna having a normal axis; a housing enclosing the battery and the wireless power transfer circuit, wherein the housing encloses the battery and the wireless power transfer circuit to prevent ingress of water in harmful quantities during immersion in water to at least one meter for at least thirty minutes; and two wings extending from the housing parallel to the normal axis of the antenna, each wing having a curved flange extending toward an opposing one of the two wings, wherein each of the wings yields about 0.5 millimeters to an outward force of between ten and thirty Newtons, and wherein each of the curved flanges has a radius of curvature of between two hundred and two hundred fifty millimeters.

Figure 22:
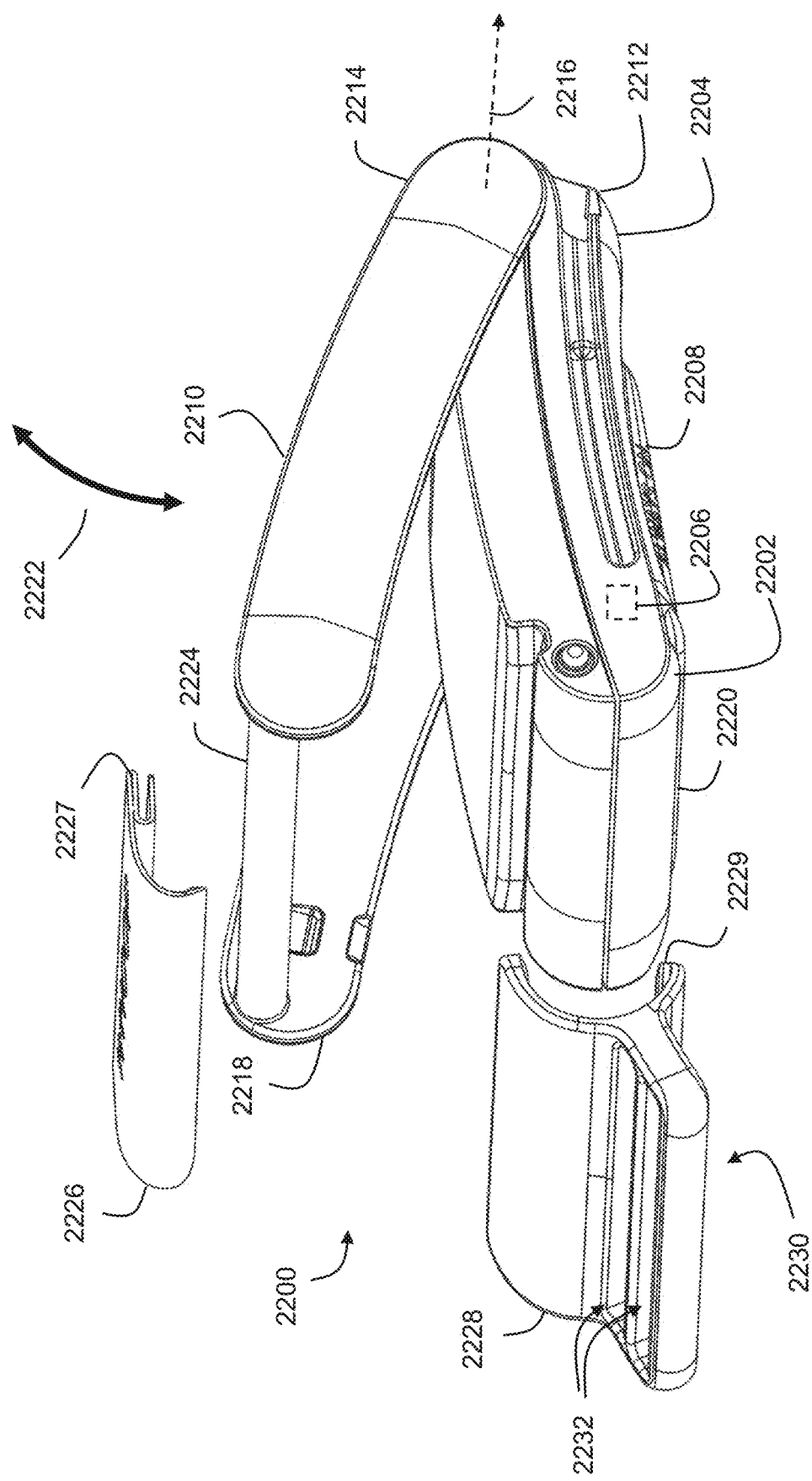
FIG. 22 shows a system including a wearable physiological monitor.

FIG. 22 shows a system 2200 including a physiological monitoring device 2202 that is structurally configured for use with an adjustable strap or band. In general, a strap, which may be any of the bands of elastic material or other straps described herein, may usefully be adjusted to a desired tension for a particular user. To this end, an adjustable strap may include a buckle on one end that removably and replaceably couples to a monitoring device while retaining a length of the strap as the buckle and strap are removed from and replaced. This advantageously permits a number of straps to be used interchangeably without requiring readjustment of strap length each time a strap is changed.

The monitoring device 2202 may be any device configured to monitor physiological data, such as a wearable physiological monitoring device that uses photoplethysmography (PPG) or the like to continuously monitor heart rate variability (HRV) and the like, or any other device described herein. The monitoring device 2202 may include a housing 2204 for sensing circuitry 2208 and a battery 2206. The housing 2204 may enclose the battery 2206 and sensing circuitry 2208 in a substantially waterproof enclosure that prevents ingress of water in harmful quantities during immersion in water to at least one meter for at least thirty minutes.

The system 2200 may include a clasp 2210 pivotally mounted to a first end 2212 of the monitoring device 2202 on a first end 2214 of the clasp 2210 where there is a rotation axis 2216. A second end 2218 of the clasp 2210 may be rotatable between a first position adjacent to a second end 2220 of the monitoring device 2202 and a second position away from the second end 2220 of the monitoring device 2202 as generally illustrated by an arrow 2222. The clasp 2210 may be rotatable around the rotation axis 2216 over an angle of 180 degrees or more. The clasp 2210 may include a cross member 2224 on the second end 2218 of the clasp 2210 having an axis aligned to the rotation axis 2216 for the clasp 2210.

The strap may be any of the adjustable bands or other straps described herein and may generally secure the physiological monitoring device 2202 in a desired location on a user's body. The strap may include a band of elastic material with a first end and a second end to provide a combination of tension to secure the device for physiological monitoring and elasticity to accommodate diameter changes resulting from user movement. The length of the band from the first end to the second end may be sufficient to wrap around a variety of body parts and accessories. In this manner, the strap may accommodate a variety of wearer sizes and shapes, as well as physical movements by the wearer. The elastic material of the band may include any material designed to resist permanent deformation such as rubber, nylon, synthetic fiber, or the like. In general, the strap may interconnect a hook 2226 and a buckle 2228, each of which may be coupled to the monitoring device 2202 and the strap as described herein. In one aspect, the strap may include a high friction material on a surface contacting the monitoring device 2202 when the clasp 2210 is in the first position. This can help to secure the strap against the monitoring device 2202 and prevent lateral or lengthwise slippage.

The hook 2226 may be crimped, adhered, or otherwise attached to the strap. In one aspect, the hook 2226 may be coupled to the strap in a non-adjustable manner, e.g., crimped or otherwise affixed to a first end 2214 of the strap. The buckle 2228 may be attached to the strap in a manner that permits adjustment of a position of the buckle 2228 along the strap in order to adjust a length of the strap, and a corresponding tension of the strap about a wrist or other body part of a user. The buckle 2228 may, for example, provide a fixture 2230 defining an overlapping path for adjustably retaining a length of a band of elastic material between the buckle 2228 and the hook 2226. In this embodiment, the strap may be woven through two adjacent slits 2232 along the overlapping path through the fixture 2230 to secure the buckle 2228 at a desired position along the strap. In some embodiments, the fixture 2230 may be a rigid structure extending from the buckle 2228. Alternatively, the fixture 2230 may be collapsed to lie unobtrusively against the buckle 2228. Other adjustment techniques are known in the art, which may also or instead be used to adjustably couple the buckle 2228 to the strap. It will be understood, however, that the hook 2226 may also or instead be adjustably coupled to the strap. The crimp 2227 of the hook 2226 may conveniently permit the hook 2226 to fold against the monitoring device 2202 with a low profile that lies flush with the clasp 2210, the strap, and other hardware. In one aspect, a circumferential tension along the strap may help to secure the hook 2226 in a rotational orientation that prevents decoupling of the hook 2226 from the rotation axis 2216 of the clasp 2210 when the clasp 2210 is in a closed position, e.g., about a wrist of a wearer.

Figure 23:
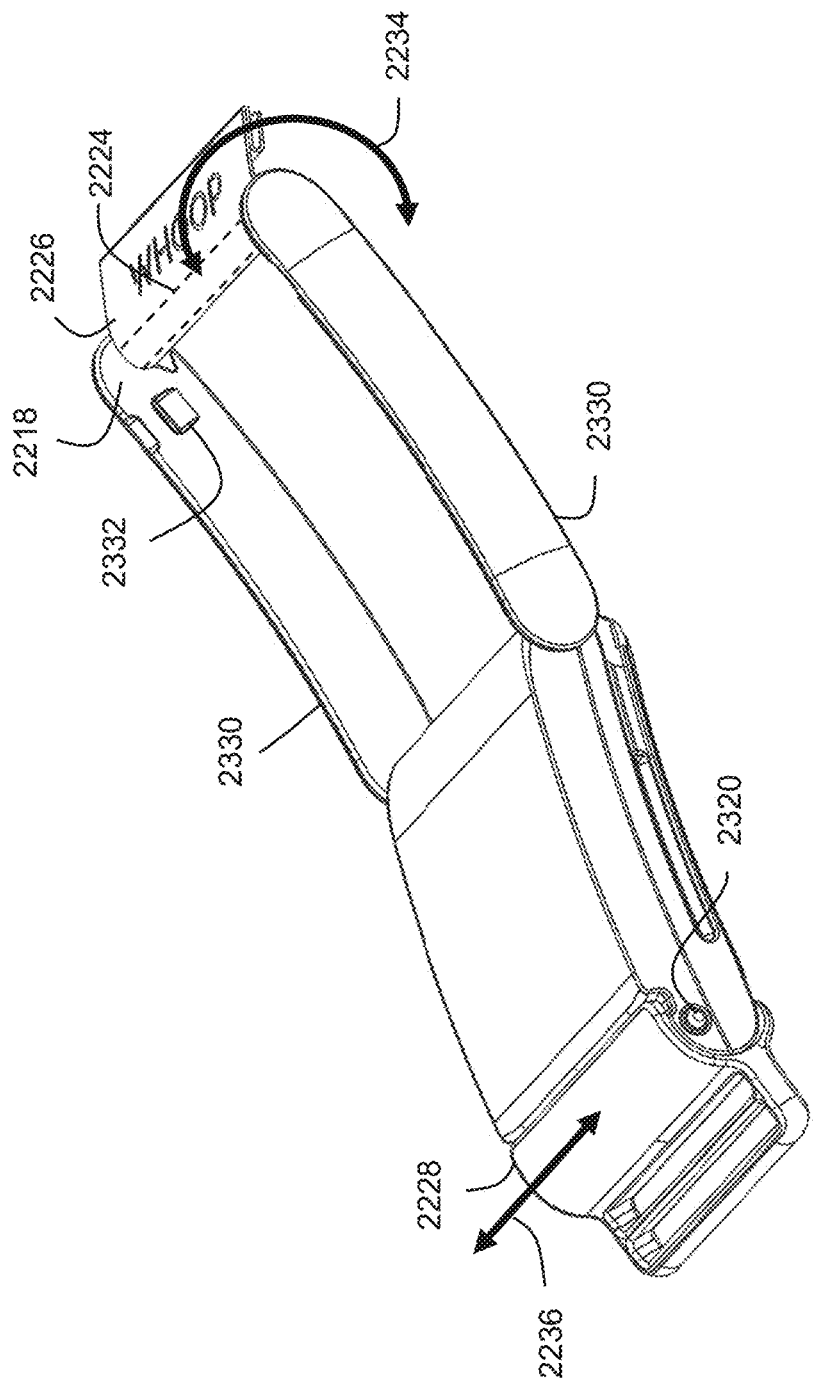
FIG. 23 shows a system including a wearable physiological monitor.

As shown in FIG. 23, the hook 2226 may be rotatably coupled to the cross member 2224 on the second end 2218 of the clasp 2210, and rotatable as indicated by an arrow 2234 to decouple the hook 2226 from the cross member 2224. Decoupling the hook 2226 in this manner may prevent unwanted couplings of the hook 2226 to the buckle 2228 to aid in removal of the monitoring device 2202.

The buckle 2228 may be linearly removable from and replaceable to the second end 2220 of the monitoring device 2202 along a second axis parallel to the rotation axis 2216 for the clasp 2210 as indicated by an arrow 2236. The buckle 2228 may include a fixture as described above providing an overlapping path for adjustably retaining a length of the band of elastic material between the hook 2226 and the buckle 2228. The buckle 2228 may, for example, have a c-shaped cross section along the second axis shaped and sized to couple to a partially cylindrical surface on the second end 2220 of the monitoring device 2202. As shown in FIG. 22, the c-shaped cross section may also include a tooth 2229 or other flange or the like shaped and sized to engage an indent in the second end 2220 of the monitoring device 2202 when the buckle 2228 is aligned for use along the second axis.

In one aspect, the monitoring device 2202 may include a spring bar 2320 or similar feature with protruding surfaces that retain the clasp 2210 in a closed position and prevent rotational movement of the clasp 2210. The clasp 2210 may include a pair of arms 2330 extending from the first end 2214 of the clasp 2210 to the second end 2218 of the clasp

2210. When closed, indents 2332 or the like may engage the protruding portions of the spring bar 2320 to secure the clasp 2210 in a closed position (or vice-versa, regarding indents/ protrusions).

Figure 24:
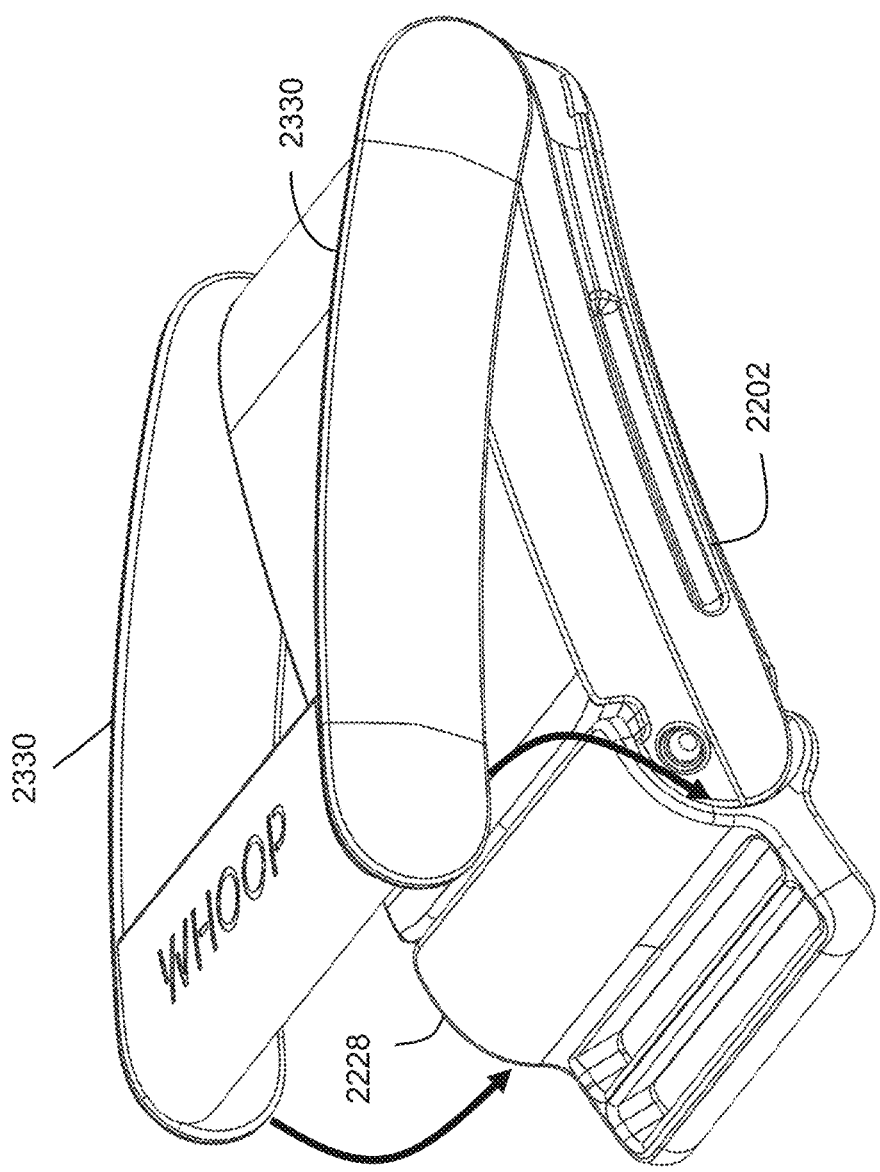
FIG. 24 shows a system including a wearable physiological monitor.

As shown in FIG. 24, when closed, the pair of arms 2330 may also overlap the ends of the buckle 2228 in order to secure the buckle 2228 against displacement along the second axis, e.g., parallel to the rotation axis 2216 of the clasp 2210. The pair of arms 2330 may generally rotate away from the second end 2220 of the monitoring device 2202 when in a second position (or open position) to permit linear movement of the buckle 2228 along the second axis to decouple the buckle 2228 from the monitoring device 2202. In this manner, the buckle 2228 may retain a target length of the strap for a user as the buckle 2228 is removed from and replaced to the monitoring device 2202, or as the user changes among different straps over time.

Figure 25:
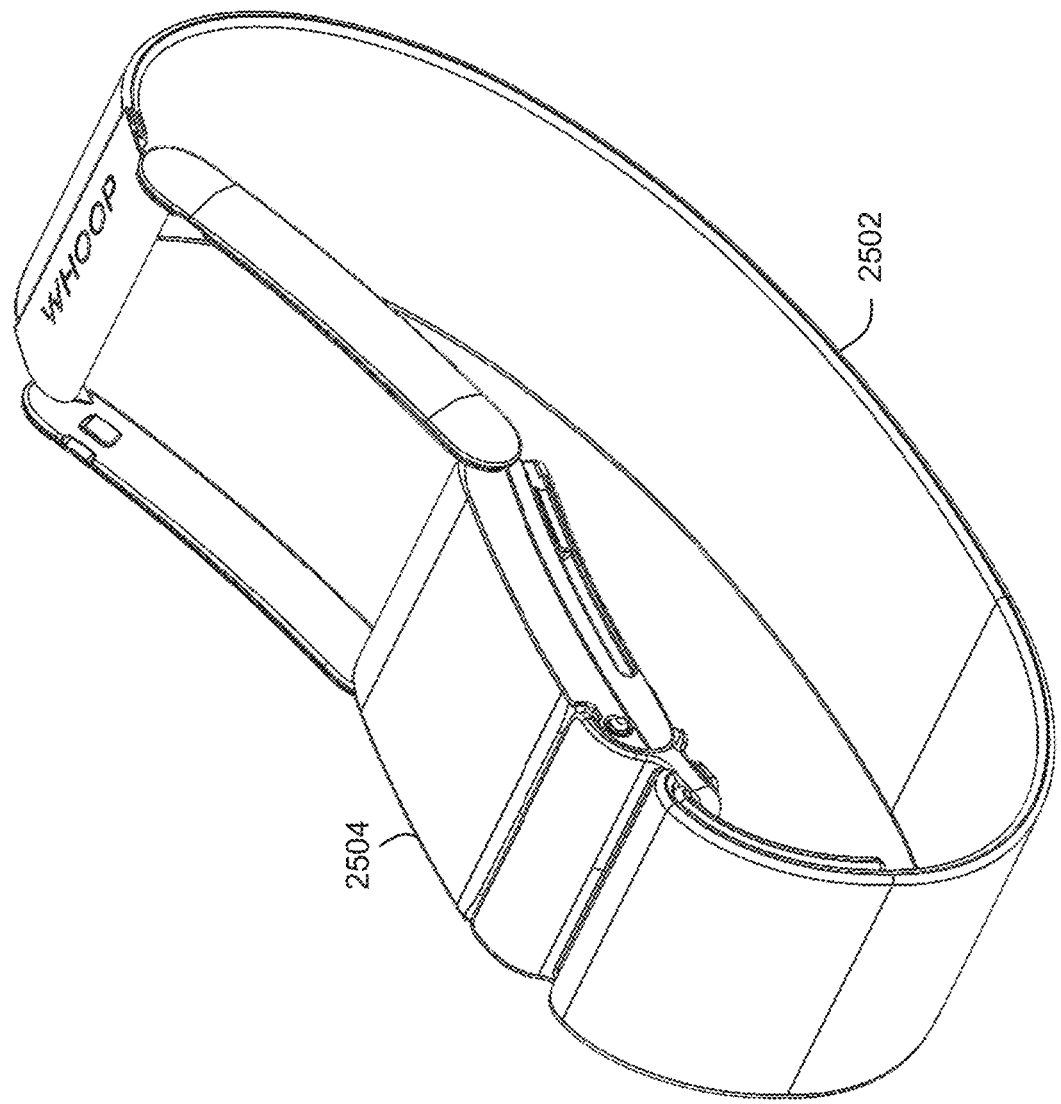
FIG. 25 shows a wearable physiological monitor with a strap.

FIG. 25 shows a wearable physiological monitor with a band such as an elastic wrist band. In general, the elastic wrist band 2502 may be an adjustable band of elastic material selected to couple to other components and/or the physiological monitor 2504 for use in retaining the physiological monitor in a desired location, e.g., on a wrist of a user. As used herein, terms such as "strap," "band," "elastic band," "adjustable band," "adjustable strap," and the like are used interchangeably to describe a band of elastic material or the like used to secure a physiological monitoring device to a wrist or other region of a user's body, unless a more specific meaning is otherwise provided or clear from the context. It will be further understood that, in some implementations, the band is relatively inelastic.

According to the foregoing, there is described herein an adjustable band for a wearable physiological monitoring device. The adjustable band may include a band of an elastic material, the band having a first end and a second end; a hook affixed to the first end of the band; and a buckle coupled to the second end of the band, the buckle having a pair of arms forming a c-shaped cross section along an axis transverse to the band, each of the arms having a flange for engaging the buckle with a device under a circumferential tension on the band, the buckle including a fixture providing an overlapping path for adjustably securing the band of material in the buckle to retain a length of the band of elastic material between the hook and the buckle under the circumferential tension on the band.

Garments

One limitation on wearable sensors is body placement. Devices are typically wrist-based, and may occupy a location that a user would prefer to reserve for other devices or jewelry, or that a user would prefer to leave unadorned for aesthetic or functional reasons. This location also places constraints on what measurements can be taken, and may also limit user activities. For example, a user may be prevented from wearing wear boxing gloves while wearing a sensing device on their wrist. To address this issues, physiological monitors may also or instead be embedded in clothing, which may be specifically adapted for physiological monitoring with the addition of communications interfaces, power supplies, device location sensors, environmental sensors, geolocation hardware, payment processing systems, and any other components to provide infrastructure and augmentation for wearable physiological monitors. Such "smart garments" offer additional space on a user's body for supporting monitoring hardware, and may further enable sensing techniques that cannot be achieved with single sensing devices. For example, embedding a plurality of physiological sensors or other electronic/communication devices in a shirt may allow electrocardiogram (ECG) based heart rate measurements to be gathered from a torso region of the wearer; wireless antennas to be placed above the upper portion of the thoracic spine to achieve desired communications signals; a contactless payment system to be embedded in a sleeve cuff for interactions with a payment terminal; and muscle oxygen saturation measurements to be gathered from muscles such as the pectoralis major, latissimus dorsi, biceps brachii, and other major muscle groups. This non-exhaustive list illustrates just some examples of technology that may be incorporated into a single garment.

Smart garments may also free up body surfaces for other devices. For example, if sensors in a wrist-worn device that provide heart rate monitoring and step counting can be instead embedded in a user's undergarments, the user may still receive the biometric information they desire, while also being able to wear jewelry or other accessories for suitable occasions.

The present disclosure is generally directed to smart garment systems and techniques. It will be understood that a "smart garment" as described herein generally includes a garment the incorporates infrastructure and devices to support, augment, or complement various physiological monitoring modes. Such a garment may include a wired, local communication bus for intra-garment hardware communications, a wireless communication system for intra-garment hardware communications, a wireless communication system for extra-garment communications and so forth. The garment may also or instead include a power supply, a power management system, processing hardware, data storage, and so forth, any of which may support enriched functions for the smart garment.

Figure 26:
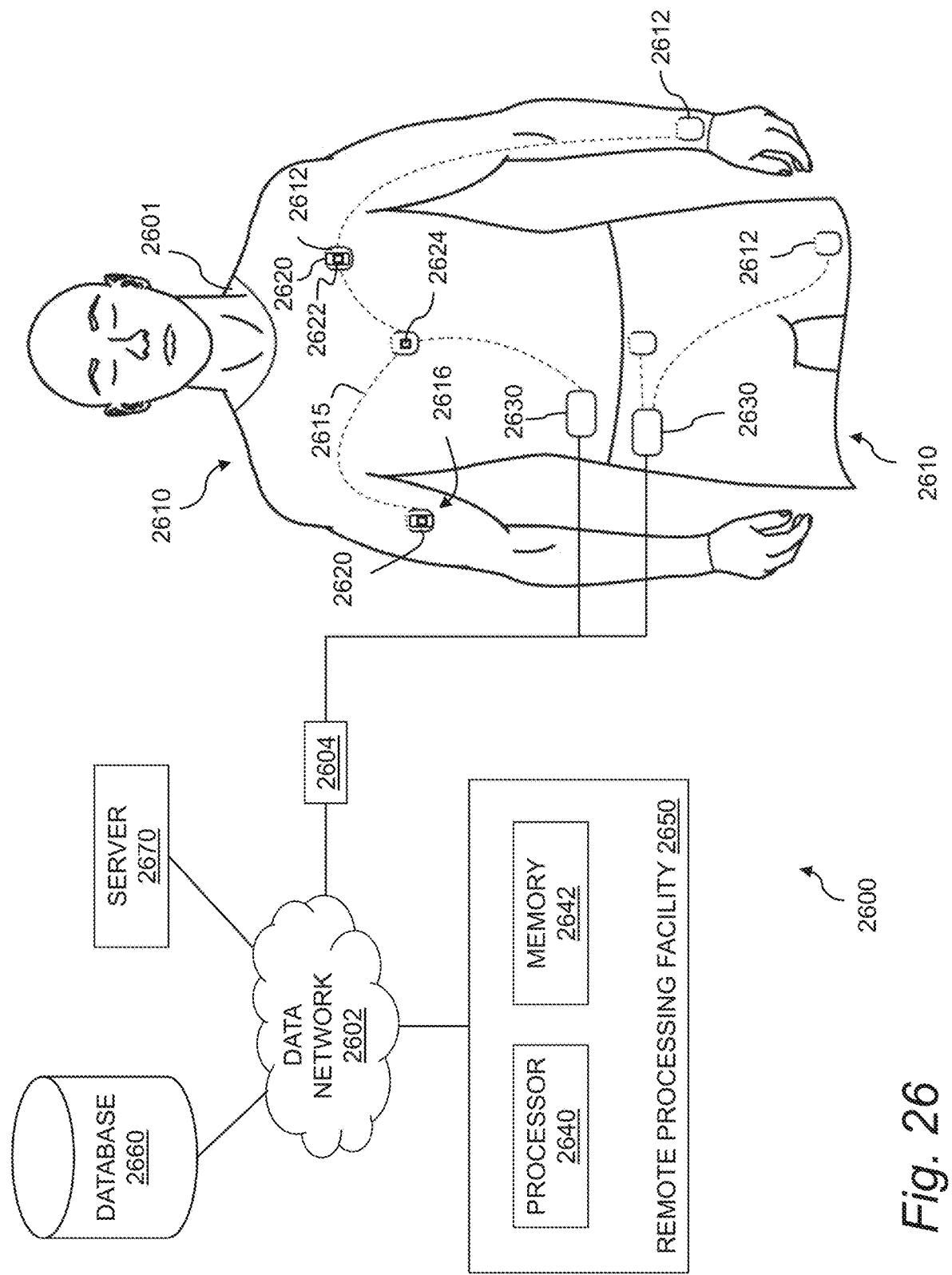
FIG. 26 shows a smart garment system.

FIG. 26 shows a smart garment system. In general, the system 2600 may include a plurality of components—e.g., a garment 2610, one or more modules 2620, a controller 2630, a processor 2640, a memory 2642, and so on—capable of communicating with one another over a data network 2602. The garment 2610 may be wearable by a user 2601 and configured to communicate with a module 2620 having a physiological sensor 2622 that is structurally configured to sense a physiological parameter of the user 2601. As discussed herein, the module 2620 may be controllable by the controller 2630 based at least in part on a location 2616 where the module 2620 is located on or within the garment 2610. This position-based information may be derived from an interaction and/or communication between the module 2620 and the garment 2610 using various techniques. It will be understood that, while two controllers 2630 are shown, the garment 2610 may include a single inter-garment controller, or any number of separate controllers 2630 in any number of garments 2610 (e.g., one per garment, or one for all garments worn by a person, etc.), and/or controllers may be integrated into other modules 2620.

For communication over the data network 2602, the system 2600 may include a network interface 2604, which may be integrated into the garment 2610, included in the controller 2630, or in some other module or component of the system 2600, or some combination of these. The network interface 2604 may be configured to wirelessly communicate data through the data network 2602. The data network 2602 may include any communication network through which computer systems may exchange data. For example, the data network 2602 may include, but is not limited to, the Internet, an intranet, a LAN (Local Area Network), a WAN (Wide Area Network), a MAN (Metropolitan Area Network), a wireless network, a cellular data network, an optical network, and the like. To exchange data via the data network

2602, the system 2600 and the data network 2602 may use various methods, protocols, and standards including, but not limited to, token ring, Ethernet, wireless Ethernet, Bluetooth, TCP/IP, UDP, HTTP, FTP, SNMP, SMS, MMS, SS7, JSON, XML, REST, SOAP, CORBA, HOP, RMI, DCOM and Web Services. To ensure data transfer is secure, the system 2600 may transmit data via the data network 2602 using a variety of security measures including, but not limited to, TSL, SSL and VPN. By way of example, some embodiments of the system 2600 may be configured to stream information wirelessly to a social network, a data center, a cloud service, and so forth.

In some embodiments, data streamed from the system 2600 to the data network 2602 may be accessed by the user 2601 (or other users) via a website. The network interface 2604 may thus be configured such that data collected by the system 2600 is streamed wirelessly to a remote processing facility 2650, database 2660, and/or server 2670 for processing and access by the user. In some embodiments, data may be transmitted automatically, without user interactions, for example by storing data locally and transmitting the data over available local area network resources when available. In some embodiments, the system 2600 may include a cellular chip or other hardware for independently accessing network resources from the garment 2610 without requiring local network connectivity.

In one example, the network interface 2604 may be configured to stream data using Bluetooth or Bluetooth Low Energy technology, e.g., to a nearby device such as a cell phone or tablet for forwarding to other resources on the data network 2602. In another example, the network interface 2604 may be configured to stream data using a cellular data service, such as via a 3G, 4G, or 5G cellular network. It will be understood that the network interface 2604 may include a computing device such as a mobile phone or the like. The network interface 2604 may also or instead include or be included on another component of the system 2600, or some combination of these. Where battery power or communications resources can advantageously be conserved, the system 2600 may preferentially use local networking resources when available, and reserve cellular communications for situations where a data storage capacity of the garment 2610 is reaching capacity. Thus, for example, the garment 2610 may store data locally up to some predetermined threshold for local data storage, below which data is transmitted over local networks when available. The garment 2610 may also transmit data to a central resource using a cellular data network only when local storage of data exceeds the predetermined threshold.

The garment 2610 may include one or more of a shirt (or other top), shorts/pants (or other bottom), an undergarment (e.g., undershirt, underwear, brassiere, and so on), a sock or other footwear, a shoe, a facemask, a hat or helmet (or other head adornment), a compression sleeve, a sweatband, kinesiology tape or elastic therapeutic tape, a glove, and the like. More generally, the garment 2610 may include any type(s) of wearable clothing or adornment suitable for wearing by a user and retaining one or more sensing modules as contemplated herein.

The garment 2610 may include one or more designated areas 2612 for positioning a module to sense a physiological parameter of the user 2601 wearing the garment 2610. One or more of the designated areas 2612 may be specifically tailored for receiving a module 2620 therein or thereon. For example, a designated area 2612 may include a pocket structurally configured to receive a module 2620 therein. Also or instead, a designated area 2612 may include a first fastener configured to cooperate with a second fastener disposed on a module 2620. One or more of the first fastener and the second fastener may include at least one of a hook-and-loop fastener, a button, a clamp, a clip, a snap, a projection, and a void.

The designated areas 2612 may include at least one of a torso region, a spinal region, an extremity region (e.g., one or more of an arm region such as a sleeve, and a leg region such as a pant leg), a waistband region, a cuff region, and so on. Also or instead, one or more of the designated areas 2612 may include at least a region adjacent to one or more muscle groups of the user 2601—e.g., muscle groups including at least one of the pectoralis major, latissimus dorsi, biceps brachii, and so on.

By placing a pocket or the like in one of these designated areas 2612, a position of a module 2620 can be controlled, and where an RFID tag, sensor, or the like is used, the designated area 2612 can specifically sense when a module 2620 is positioned there for monitoring, and can communicate the detected location to any suitable control circuitry. In this manner, a garment 2610 may facilitate the installation of modules 2620 in many different, discrete locations, the placement of which can be controlled by the configuration of the garment 2610, and the use of which can be automatically detected when corresponding control modules 2620 are placed there for use. Also or instead, the garment 2610 may facilitate the placing of the modules 2620 over relatively large regions of the garment 2610. For example, a garment 2610 may include a relatively large region (in terms of surface area) where a module 2620 can be affixed or otherwise secured, e.g., by loops, straps, buttons, sheets of hook-and-loop fasteners, and so forth.

In general, each designated area 2612 may include a pocket such as any of those described above, or any other mounting fixture or combination of fixtures. Where a pocket is used, the pocket may be configured as describe above to preferentially urge a module 2620 within the pocket toward the user's skin under normal pressure. Without limiting the generality of the foregoing, this may generally include an exterior layer of the pocket that is less elastic than an interior surface of the pocket so that when circumferential tension is applied (e.g., when the garment 2610 is donned), the pocket preferentially urges a contact surface of the sensor inward toward the intended target surface with at least a predetermined normal force (when the garment 2610 is properly sized for the user). In this respect, it will be understood that although some variation in normal force among users and garments is inevitable, typical tensions for comfortable use of properly fitted athletic wear are generally known, and adequate contact force to obtain a high quality physiological signal is generally known, and in any event readily observable in acquired data. As such, adequate circumferential tensions and resulting normal contact forces needed to promote good contact between sensing regions of the module 2620 (such as LEDs, capacitive touch sensors, photodiodes, and the like) and the user's skin may readily be determined, and can advantageously facilitate the use of wrist-worn sensor housings such as those described above with one of the garments 2610 described herein for off-wrist monitoring if/when desired.

In one aspect, the designated areas 2612 may usefully be positioned where reinforcing elastic bands are typically provided on garments, e.g., around the mid-torso for a sports bra, around the waist on shorts or underwear, or on the sleeves of a t-shirt. In one aspect, the designated areas 2612 may also usefully be positioned according to the intended physiological measurement, e.g., near major arteries suitable for heart rate detection using photoplethysmography. In one aspect, the garment 2610 may usefully distribute these designated areas 2612 (and supporting infrastructure such as wired connectors, location identification tags, and the like) at the intersection of regions where good physiological signals can be obtained and regions where adequate normal forces for good sensor contact can be generated by clothing. For example, this may include the ankles, the waist, the mid-torso, the biceps, the wrists, the forehead, and so on.

The garment 2610 may also or instead incorporate other infrastructure 2615 to cooperate with a module 2620. For example, the garment infrastructure 2615 may include wires or the like embedded in the garment 2610 to facilitate wired data or power transfer between installed modules 2620 and other system components (including other modules 2620). The infrastructure 2615 may also or instead include integrated features for, e.g., powering modules, supporting data communications among modules, and otherwise supporting operation of the system 2600. The infrastructure 2614 may also or instead include location or identification tags or hardware, a power supply for powering modules 2620 or other hardware, communications infrastructure as described herein, a wired intra-garment network, or supplemental components such as a processor, a Global Positioning System (GPS), a timing device, e.g., for synchronizing signals from multiple garments, a beacon for synchronizing signals among multiple modules 2620, and so forth. More generally, any hardware, software, or combination of these suitable for augmenting operation of the garment 2610 and a physiological monitoring system using the garment 2610 may be incorporated as infrastructure 2615 into the garment 2610 as contemplated herein.

The modules 2620 may generally be sized and shaped for placement on or within the one or more designated areas 2612 of the garment 2610. For example, in certain implementations, one or more of the modules 2620 may be permanently affixed on or within the garment 2610. In such instances, the modules 2620 may be washable. Also or instead, in certain implementations, one or more of the modules 2620 may be removable and replaceable relative to the garment 2610. In such instances, the modules 2620 need not be washable, although a module 2620 may be designed to be washable and/or otherwise durable enough to withstand a prolonged period of engagement with a designated area 2612 of the garment 2610. A module 2620 may be capable of being positioned in more than one of the designated areas 2612 of the garment 2610. That is, one or more of the plurality of modules 2620 may be configured to sense data using a physiological sensor 2622 in a plurality of designated areas 2612 of the garment 2610.

Removable and replaceable modules 2620 may provide several advantages such as ease of garment care (e.g., washing) and power management (e.g., removal for recharging). Furthermore, removability may facilitate replacement and/or repositioning of modules within the garment 2610 for different sensing activities or other reconfigurations, replacement of damaged or defective modules 2620, and so forth.

A module 2620 may include one or more physiological sensors 2622 and a communications interface 2624 programmed to transmit data from at least one of the physiological sensors 2622. For example, the physiological sensors 2622 may include one or more of a heart rate monitor, an oxygen monitor (e.g., a pulse oximeter), a thermometer, an accelerometer, a gyroscope, a position sensor, a Global Positioning System, a clock, a galvanic skin response (GSR) sensor, or any other electrical, acoustic, optical, or other sensor or combination of sensors and the like useful for physiological monitoring, environmental monitoring, or other monitoring as described herein. In one aspect, the physiological sensors 2622 may include a conductivity sensor or the like used for electromyography, electrocardiography, electroencephalography, or other physiological sensing based on electrical signals. The data received from the physiological sensors 2622 may include at least one of heart rate data, muscle oxygen saturation data, temperature data, movement data, position/location data, environmental data, temporal data, and so on.

In one aspect, a module 2620 may be configured for use on multiple body locations. For example, the module 2620 may be one of the wrist-worn sensors described above. The module 2620 may be adapted for use with a garment 2610 in various ways. In one aspect, the module 2620 may have relatively smooth, continuous exterior surfaces to facilitate sliding into and out of a pocket, such as any of the pockets described herein, or any other suitable retaining structure(s). In another aspect, an LED and/or sensor region may protrude from a surface of the module 2620 sufficiently to extend beyond a restraining garment material and into a contact surface of a user. The module 2620 may also include hardware to facilitate such uses. For example, a module 2620 may usefully incorporate a contact sensor for detecting contact with a user. However, the exposed contact surfaces of the module 2620 may different when retained by a wrist strap (or other limb strap) than when retained by a garment pocket. To facilitate multiple retaining modes, the module 2620 may usefully incorporate two or more contact sensors (such as capacitive sensors or other touch sensors, switches, or the like) at two different locations, each positioned to detect contact with a wearer in a different retaining mode. For example, a module 2620 may include a capacitive sensor adjacent to an optical sensing system that contacts the user's skin when the module 2620 is retained with a wrist strap. The module 2620 may also or instead optically detect contact when the capacitive sensor is covered by a garment fabric or the like that prevents direct skin contact, or a second capacitive sensor may be placed within another region exposed by the garment 2610 retaining system. In another aspect, the garment 2610 may include a capacitive sensor that provides a signal to the module 2620, or to some other system controller or the like, when a region of the garment near the module 2620 is in contact with a user's skin.

In one aspect, the physiological sensors 2622 may include a heart rate monitor or pulse sensor, e.g., where heart rate is optically detected from an artery, such as the radial artery. In one embodiment, the garment 2610 may be configured such that a module 2620 is positioned on a user's wrist, where a physiological sensor 2622 of the module 2620 is secured over the user's radial artery or other blood vessel. Secure connection and placement of a pulse sensor over the radial artery or other blood vessel facilitates measurement of heart rate, pulse oxygen, and the like. It will be understood that this configuration is provided by way of example only, and that other sensors, sensor positions, and monitoring techniques may also or instead be employed without departing from the scope of this disclosure.

In some embodiments, heart rate data may be acquired using an optical sensor coupled with one or more light emitting diodes (LEDs), all in contact with the user 2601. To facilitate optical sensing, the garment 2610 may be designed to maintain a physiological sensor 2622 in secure, continual contact with the skin, and reduce interference of outside light with optical sensing by the physiological sensor 2622.

Thus, certain embodiments include one or more physiological sensors 2622 configured to provide continuous measurements of heart rate using photoplethysmography or the like. The physiological sensor 2622 may include one or more light emitters for emitting light at one or more desired frequencies toward the user's skin, and one or more light detectors for received light reflected from the user's skin. The light detectors may include a photo-resistor, a phototransistor, a photo-diode, and the like. A processor may process optical data from the light detector(s) to calculate a heart rate based on the measured, reflected light. The optical data may be combined with data from one or more motion sensors, e.g., accelerometers and/or gyroscopes, to minimize or eliminate noise in the heart rate signal caused by motion or other artifacts. The physiological sensor 2622 may also or instead provide at least one of continuous motion detection, environmental temperature sensing, electrodermal activity (EDA) sensing, galvanic skin response (GSR) sensing, and the like.

The system 2600 may include different types of modules 2620. For example, a number of different modules 2620 may each provide a particular function. Thus, the garment 2610 may house one or more of a temperature module, a heart rate/PPG module, a muscle oxygen saturation module, a haptic module, a wireless communication module, or combinations thereof, any of which may be integrated into a single module 2620 or deployed in separate modules 2620 that can communicate with one another. Some measurements such as temperature, motion, optical heart rate detection, and the like, may have preferred or fixed locations, and pockets or fixtures within the garment 2610 may be adapted to receive specific types of modules 2620 at specific locations within the garment 2610. For example, motion may preferentially be detected at or near extremities while heart rate data may preferentially be gathered near major arteries. In another aspect, some measurements such as temperature may be measured anywhere, but may preferably be measured at a single location in order to avoid certain calibration issues that might otherwise arise through arbitrary placement.

In another aspect, the system 2600 may include two or more modules 2620 placed at different locations and configured to perform differential signal analysis. For example, the rate of pulse travel and the degree of attenuation in a cardiac signal may be detected using two or more modules at two or more locations, e.g., at the bicep and wrist of a user, or at other locations similarly positioned along an artery. These multiple measurements support a differential analysis that permits useful inferences about heart strength, pliability of circulatory pathways, and other aspects of the cardiovascular system that may indicate cardiac age, cardiac health, cardiac conditions, and so forth. Similarly, muscle activity detection might be measured at different locations to facilitate a differential analysis for identifying activity types, determining muscular fitness, and so forth. More generally, multiple sensors can facilitate differential analysis. To facilitate this type of analysis with greater precision, the garment infrastructure may include a beacon or clock for synchronizing signals among multiple modules, particularly where data is temporarily stored locally at each module, or where the data is transmitted to a processor from different locations wirelessly where packet loss, latency, and the like may present challenges to real time processing.

The communications interface 2624 may be any as described herein, for example including any of the features of the network interface 2604 described above. The communications interface 2624 may be a separate device that provides the ability for the modules 2620 to communicate with one another and/or with other components of the system 2600), or there may be a central module that communicates with other modules 2620 (or with another component of the system 2600). It will be understood that communications may usefully be secured using any suitable encryption technology in order to ensure privacy and security of user data. This may, for example, include encryption for local (wired or wireless) communications among the modules 2620 and/or controller 2630 within the garment 2610. This may also or instead include encryption for remote communications to a server and other remote resources. In one aspect, the garment 2610 and/or controller 2630 may provide a cryptographic infrastructure for securing local communications, e.g., by managing public/private key pairs for use in asymmetric encryption, authentication, digital signatures, and so forth. The keys for this infrastructure may also or instead be managed by an external, trusted third-party.

The controller 2630 may be configured, e.g., by computer executable code or the like, to determine a location of the module 2620. This may be based on contextual measurements such as accelerometer data from the module 2620, which may be analyzed by a machine learning model or the like to infer a body position. In another aspect, this may be based on other signals from the module 2620. For example, signals from sensors such as photodiodes, temperature sensors, resistors, capacitors, and the like may be used alone or in combination to infer a body position. In another aspect, the location may be determined based on a proximity of a module 2620 to a proximity sensor, RFID tag, or the like at or near one of the designated areas 2612 of the garment 2610. Based on the location, the controller 2630 may adapt operation of the module 2620 for location-specific operation. This may include selecting filters, processing models, physiological signal detections, and the like. It will be understood that operations of the controller 2630, which may be any controller, microcontroller, microprocessor, or other processing circuitry, or the like, may be performed in cooperation with another component of the system 2600 such as the processor 2640 described herein, one or more of the modules 2620, or another computing device. It will also be understood that the controller 2630 may be located on a local component of the system 2600 (e.g., on the garment 2610, in a module 2620, and so on) or as part of a remote processing facility 2650, or some combination of these. Thus, in an aspect, a controller 2630 is included in at least one of the plurality of modules 2620. And, in another aspect, the controller 2630 is a separate component of the garment 2610, and serves to integrate functions of the various modules 2620 connected thereto. The controller 2630 may also or instead be remote relative to each of the plurality of modules 2620, or some combination of these.

Location detection may also usefully be recorded and used in a number of ways by a human user and/or by the system 2600. For example, a detected location may be stored, along with the corresponding garment, so that a user can retrieve a placement history and replace the module 2620 to a previous location for a particular garment as desired. In another aspect, the detected location may be used by the system 2600 to analyze data and make garment specific recommendations. For example, the system 2600 may evaluate the quality of a signal, e.g., using any conventional metrics such as signal-to-noise ratio, or using quality metrics more specific to physiological signals such as correlation to an expected signal or pulse shape, consistency with a rate or magnitude typical for a sensor, pulseto-pulse consistency for a particular user, or any other measure of signal quality using statics, machine learning, digital signal processing techniques, or the like. A quality metric, however derived, may be used in turn to recommend specific placements of a module 2620 on a garment 2610 for a user, or to recommend a particular garment 2610 for the user. Thus, for example, after acquiring data over a range of garments and activities, the system 2600 may generate a user-actionable recommendation such as, "It appears that when you are jogging, the most accurate heart rate signals can be obtained when you are wearing an XL shirt model number xxxxxx. You may wish to wear this shirt for active workouts, and you may wish to purchase more of this type of shirt for regular use." Or, "It appears that one of your modules is not obtaining accurate temperature readings when located on your sleeve elastic band. You may wish to try a different location for this module, or to try a different garment." More generally, data quality may be measured for a number of different modules at different locations in different garments during different activities, and this data may be used to generate customized recommendations for a user on a per-garment and per-location basis. These recommendations may also be tailored to specific activity types where this data is accurately recorded by the system 2600, either from user input, automatic detection, or some combination of these.

The controller 2630 may be configured to control one or more of (i) sensing performed by a physiological sensor 2622 of the module 2620 and (ii) processing by the module 2620 of the data received from a physiological sensor 2622. That is, in certain aspects, the combination of sensors in the module 2620 may vary based on where it is intended to be located on a garment 2610. In another aspect, processing of data from a module 2620 may vary based on where it is located on a garment 2610. In this latter aspect, a processing resource such as the controller 2630 or some other local or remote processing resource coupled to the module 2620 may detect the location and adapt processing of data from the module 2620 based on the location. This may, for example, include a selection of different models, algorithms, or parameters for processing sensed data.

In another aspect, this may include selecting from among a variety of different activity recognition models based on the detected location. For example, a variety of different activity recognition models may be developed such as machine learning models, lookup tables, analytical models, or the like, which may be applied to accelerometer data to detect an activity type. Other motion data such as gyroscope data may also or instead be used, and activity recognition processes may also be augmented by other potentially relevant data such as data from a barometer, magnetometer, GPS system, and so forth. This may generally discriminate, e.g., between being asleep, at rest, or in motion, or this may discriminate more finely among different types of athletic activity such as walking, running, biking, swimming, playing tennis, playing squash, and so forth. While useful models may be developed for detecting activities in this manner, the nature of the detection will depend upon where the accelerometers are located on a body. Thus, a processing resource may usefully identify location first using location detection systems (such as tags, electromechanical bus connections, etc.) built into the garment 2610, and then use this detected location to select a suitable model for activity recognition. This technique may similarly be applied to calibration models, physiological signals processing models, and the like, or to otherwise adapt processing of signals from a module 2620 based on the location of the module 2620.

Determining the location of a module 2620 may include receiving a sensed location for the module 2620. The sensed location may be provided by a proximity detection circuit such as a near-field-communication (NFC) tag, an (active or passive) RFID tag, a capacitance sensor, a magnetic sensor, an electrical contact, a mechanical contact, and the like. Any corresponding hardware for such proximity detections may be disposed on the module 2620 and the garment 2610 for communication therebetween to detect location when appropriate. For example, in one aspect, an NFC tag may be disposed on or within the garment 2610, and the module may include an NFC tag sensor 2620 that can detect the tag and read any location-specific information therefrom. Proximity detection may also or instead be performed using capacitively detected contact, electromagnetically detected proximity, mechanical contact, electrical coupling, and the like. In this manner, a garment 2610 may provide information to an installed module 2620 to inform the module 2620, among other things, where the module 2620 is located, or vice-versa.

Thus, communication between a module 2620 and the garment 2610 (or a processor of the garment 2610) may be used to determine the location of a module 2620 on the garment 2610. Communication of location information may be enabled using active techniques, passive techniques, or a combination thereof. For example, a thin, flexible, cheap, washable NFC tag may be sewn into the garment 2610 in various locations where a module 2620 may be placed. When a module 2620 is placed in the garment 2610, the module 2620 may query an adjacent NFC tag to determine its location. Furthermore, the NFC technique or other similar techniques may provide other information to the module 2620, including details about the garment 2610 such as the size, whether it is a gender specific piece, the manufacturer information, model or serial number of the garment, stock keeping unit (SKU), and more. Similarly, the tag may encode a unique identifier for the garment 2610 that can be used to obtain other relevant information using an online resource. The module 2620 may also or instead advertise information about itself to the garment 2610 so that the garment 2610 can synchronize processing with other modules 2620, synchronize communication among modules 2620, control or condition signals from the module 2620, and so forth. The module 2620 can then configure itself within the context of the current garment 2610 and associated modules 2620, and/or to perform certain types of monitoring or data processing.

Determining the location of a module 2620 may also or instead be based, at least in part, on an interpretation of the data received from a physiological sensor 2622 of the module 2620. By way of example, movement of a module 2620 as detected by a sensor may provide information that can be used to predict a position on or within the garment 2610. Also or instead, the type of data that is being received from a module 2620 may indicate where the module 2620 is located on the garment 2610. For example, locations may produce unique signatures of acceleration, gyroscope activity, capacitive data, optical data, temperature data, and the like, depending on where the module 2620 is located, and this data may be fused and analyzed in any suitable manner to obtain a location prediction.

According to the foregoing, determining the location of a module 2620 may also or instead include receiving explicit input from the user 2601, which may identify one of the designated areas on the garment 2610, or a general area of the body (e.g., left wrist, right ankle, and so forth). Because the location of the module 2620 relative to the garment 2610 may be determined from an analysis of a plurality of data sources, the system 2600 may include a component (e.g., the processor 2640) that is configured to reconcile one or more potential sources of location of information based on expected reliability, measured quality of data, express user input, and so forth. A prediction confidence may also usefully be generated in this context, which may be used, for example, to determine whether a user should be queried for more specific location information. More generally, any of the foregoing techniques may be used along or in combination, along with a failsafe measure the requests user input when location cannot confidently be predicted. Also or instead, a user may explicitly specify a prediction preemptively, or as an override to an automatically generated prediction.

Once determined using any of the techniques above, the location of a module 2620 may be transmitted for storage and analysis to a remote processing facility 2650, a database 2660, or the like. That is, in addition to the module 2620 using this information locally to configure itself for the location in which it is worn, the module 2620 may communicate this information to other modules 2620, peripherals, or the cloud. Processing this information in the cloud may help an organization determine if a module 2620 has ever been installed on a garment 2610, which locations are most used, and how modules 2620 perform differently in different locations. These analytics may be useful for many purposes, and may, for example, be used to improve the design or use of modules 2620 and garments 2610, either for a population, for a user type, or for a particular user.

As stated above, the system 2600 may further include a processor 2640 and a memory 2642. In general, the memory 2642 may bear computer executable code configured to be executed by the processor 2640 to perform processing of the data received from one or more modules 2620. One or more of the processor 2640 and the memory 2642 may be located on a local component of the system 2600 (e.g., the garment 2610, a module 2620, the controller 2630, and the like) or as part of a remote processing facility 2650 or the like as shown in the figure. Thus, in an aspect, one or more of the processor 2640 and the memory 2642 is included on at least one of the plurality of modules 2620. In this manner, processing may be performed on a central module, or on each module 2620 independently. In another aspect, one or more of the processor 2640 and the memory 2642 is remote relative to each of the plurality of modules 2620. For example, processing may be performed on a connected peripheral device such as smart phone, laptop, local computer, or cloud resource.

The memory 2642 may store one or more algorithms, models, and supporting data (e.g., parameters, calibration results, user selections, and so forth) and the like for transforming data received from a physiological sensor 2622 of the module 2620. In this manner, suitable models, algorithms, tuning parameters, and the like may be selected for use in transforming the data based on the location of the module 2620 as determined by the controller 2630 and/or processor 2640 as described herein. By way of example, algorithms that convert data from an accelerometer in a module 2620 into a count of a user's steps may be different depending on whether the module 2620 is worn on the user's wrist or on the user's waist band. Similarly, the intensity of an LED and corresponding sensitivity of a photodetector may be different for a PPG device placed on the wrist or the thigh. Thus, the module 2620 may self-configure for a location by controlling one or more of sensor types, sensor parameters, processing models, and so forth based on a detected location for the module 2620.

Selection of an algorithm may also or instead include an analysis of one or more of the sensor data, metadata, and the like. By way of example, an algorithm may be selected at least in part based on metadata received from one of the module 2620 and the garment 2610. This metadata may be derived from communication between the module 2620 and the garment 2610—e.g., between a tag and tag reader for exchanging information therebetween. For example, the garment 2610 may include stored in a tag garment-specific metadata that is readable by or otherwise transmittable to one or more of the plurality of modules 2620, the controller 2630, and the processor 2640. Such garment-specific metadata may include at least one of a type of garment 2610, a size of the garment 2610, garment dimensions, a gender configuration of the garment 2610, a manufacturer, a model number, a serial number, a SKU, a material, fit information, and so on. In one aspect, this information may be provided with one or more of the location identification tags described herein. In another aspect, the garment 2610 may include an additional tag at a suitable location (e.g., near or accessible to a processor or controller) that provides garment-specific information while other tags provide location-specific information.

The metadata may also or instead include at least one of a gender of the user 2601, a weight of the user 2601, a height of the user 2601, an age of the user 2601, metadata associated with the garment 2610 (e.g., the garment size, type, material, etc.), and the like. The metadata may be derived, at least in part, from user-provided input, or otherwise from information derived from the user 2601 such as a user's account information as a participant in the system 2600. By way of example, a processing algorithm may be selected depending on the material of the garment 2601 as communicated by its serial or model number in an identification tag, the physiology of the user 2601 as implied by the garment size, and so on. The metadata may also or instead be used to verify the authenticity of the garment 2610, and otherwise control access to the garment 2610 and/or modules 2620 coupled to the garment 2610. In one aspect, metadata (e.g., size, material) may be encoded directly into the garment metadata. In another aspect, the garment 2610 may publish a unique identifier that can be used to retrieve related information from a manufacturer or other data source. This latter approach advantageously permits correlation of garment-specific data with other user-specific data such as height, weight, body composition, and so forth.

Simply knowing a priori where a module 2620 is positioned may allow for the use of algorithms that have been developed to perform optimally in that particular location. This can relieve a significant computational burden otherwise borne by the module 2620 to analytically evaluate location based on available signals. Other information may also or instead be used to select an optimal algorithm. For example, based on the gender or dimensions of a garment, the algorithm may employ different models or different model parameters.

The processor 2640 may be configured to assess the quality of the data received from a physiological sensor 2622 of the module 2620. For example, the processor 2640 may be configured to provide, based on the quality of the data, a recommendation regarding at least one of the location of a module 2620 and an aspect of the garment 2610 (e.g., size, fit, material, and so on). For example, the processor 2640 may be configured to detect when the garment does not properly fit the wearer for acquisition of physiological data, for example, by detecting when a module is moving (e.g., from accelerometer data) but data quality is poor or absent for a sensed physiological signal. In general, the garment 2610 may store its own identifier and/or metadata, e.g., as described herein, or garment identification data may be stored in tags, e.g., at designated areas 2612 of the garment 2610. The processor 2640 may be configured to use this garment identification information and/or metadata to provide a recommendation regarding a different garment 2610 for the user 2601, or for an adjustment to the current garment 2610. For example, if a particular garment 2610 seems to result in low-quality data, the user 2601 could be encouraged to select an alternative size, or to make some other adjustment. Moreover, data on how many times a garment 2601 is used may be gathered and used to inform business decisions, for example, which garments 2601 provide the highest-quality data, and which garments 2610 are most preferred by users 2601.

The system 2600 may further include a database 2660, which may be located remotely and in communication with the system 2600 via the data network 2602. The database 2660 may store data related to the system 2600 such as any discussed herein—e.g., sensed data, processed data, transformed data, metadata, physiological signal processing models and algorithms, personal activity history, and the like. The system 2600 may further include one or more servers 2670 that host data, provide a user interface, process data, and so forth in order to facilitate use of the modules 2620 and garments 2610 as described herein.

It will be appreciated that the garment 2610, modules 2620, and accompanying garment infrastructure and remote networking/processing resources, may advantageously be used in combination to improve physiological monitoring and achieve modes of monitoring not previously available. A variety of such techniques using the systems and methods above are now described in greater detail.

Differential Analysis Techniques

Wearable technology has facilitated, among many other things, the collection of a wide variety of biometric data from the wearer. Some common sensor modalities in wearable devices include, but are not limited to, photoplethysmography (PPG), acceleration, angular velocity, electrocardiography (EKG), electromyography (EMG), electroencephalography (EEG), temperature, and the like. Due to the discrete nature of most existing wearable devices, a user will typically wear a limited number of devices, with each device collecting a unique set of signals. For example, a user may wear a device on their wrist to gather acceleration and PPG data, while simultaneously wearing a chest-strap to collect EKG data. A single source of data may be sufficient to extract metrics that are of interest to the user—for example, the PPG signal in the aforementioned example from one sensor may be processed to extract a heart rate, which can be a valuable metric for assessing cardiovascular load.

However, smart garments can greatly reduce limitations on the type and location of sensors, allowing data to be gathered from multiple sources. This data can be collectively analyzed to form specific physiological and health insights. For example, instead of a single wrist-worn device gathering data from a single PPG sensor, or requiring a user to attach many discrete devices all over their body, a smart garment may incorporate multiple PPG sensors (or other sensors), where each can gather data from a different location, such as a smart garment in the form of a shirt having sensors gathering data from a wrist, a bicep, chest, back, and/or shoulder. This non-limiting example may be expanded to include many sensor modalities across multiple locations in many different types of garments, and an underlying benefit of this approach can include facilitating data capture from many different locations.

Access to multiple signals may also or instead facilitate the ability to extract metrics that would otherwise be difficult or impossible to obtain. For example, if PPG sensors are located on a wearer's wrist and bicep of the same arm and are simultaneously collecting data, a time delay in the arterial pressure wave as it travels down the wearer's arm may provide information about blood volumetric flow rate, pressure, and/or other metrics of interest that may not be possible with only one of these sensor locations. Similarly, the collection of data from both the right and left wrist of a user can provide information about bilateral differences in circulation.

It will be understood that, while some examples emphasize PPG sensing, implementations may include other sensors and metrics. Similarly, although a smart garment formed as a shirt provides a useful example of the present teachings, implementations may include smart garments in other forms, as well as combinations of different smart garments. By way of example, differential measurements of metrics at or near the head can be useful given the presence of the brain, and thus smart garments may include hats, headdresses, headbands, and the like.

It will be further understood that, while teachings of a plurality of sensors exist—such as those disclosed in U.S. Pat. No. 10,105,98, which is incorporated by reference herein—these teachings typically focus on reducing noise in a physiological signal (e.g., noise associated with EMG sensors) and/or capturing motion of a wearer (e.g., using accelerometers, gyroscopes, and the like), rather than performing differential analyses as contemplated herein, as well as the use of other sensor modalities as contemplated herein.

Thus, the present teachings may include the use of multiple sensors located around a wearer's body to enable the determination of metrics that would be difficult or impossible with only one sensor. To this end, a smart garment can provide a convenient solution to deploy sensors throughout the body of a wearer. However, although differential analyses described herein may emphasize the use of multiple sensors disposed in one or more smart garments, it will be understood that the techniques described herein do not necessarily require that sensors be deployed in a garment. For example, in some instances, multiple devices may be independently worn on different limbs to facilitate various types of differential analysis.

Some classes of differential measurements that can be used with multiple sensors dispersed throughout a wearer's body (e.g., via inclusion on or within a smart garment) will now be described—e.g., concurrent measurements, synchronous measurements, asynchronous measurements, and bilateral measurements. However, it should be understood that these classes are not exclusive or exhaustive, but are useful examples of certain implementations of the present teachings.

Implementations may include obtaining and analyzing substantially concurrent or synchronous measurements. It will be understood that "concurrent measurements" in this context shall include measurements taken from two or more locations (and/or two or more different sensors at a single location) substantially simultaneously that are intended to reflect the same physiological moment. As a practical matter, it may not be possible to achieve perfect concurrence between two measurements, however measurements may be considered concurrent or substantially concurrent as understood herein if they are sufficiently close in time to be treated as concurrent for the purposes of further processing such as evaluation of physiological phenomena as described herein (e.g., within a few milliseconds of each other, or for some measurements, preferably within one millisecond or less of each other). "Synchronous" measurements may occur at different times and/or be taken in different places, but will generally be recorded at known relative times within a global frame of reference for time tracking. That is, the chronology or relative timing of synchronous measurements is known so that changes in a measurement (or among measurements from different sensors and/or locations) as a function of time can be determined and evaluated. The relevant time span may be short (e.g., a second or a fraction thereof) or long (e.g., over an interval of minutes or hours), provided the passage of time from the one measurement to the next is known. Concurrent measurements can be particularly useful when measuring and analyzing parameters that are expected to have different, concurrent values at different locations, e.g., pressure waves traveling through arteries, where the pressure wave might usefully be detected at two or more locations at the same time. Similarly, synchronous measurements can be particularly useful when measuring a change in a signal over a time interval, e.g., peak to peak variations in heart rate at different points during the day, or the rate at which a physiological signal such as a pulse travels down an artery. Moreover, calculating a time delay between pulses as they traverse the body with each heartbeat, or comparing variations in time or shape as such pulses traverse the body, may provide additional information about a user's cardiovascular health, and/or can facilitate the calculation of other parameters such as blood pressure.

Similarly, different types of physiological signals may be interrelated. For example, a differential analysis as described herein may compare Pulse Transit Time (PTT) and Pulse Arrival Time (PAT), where the latter is the time between an EKG R-peak (when the heart beat "fires") and the pulse pressure wave arriving at some location in the body as measured by PPG, whereas the former is the time delay between the pulse traveling between two different arterial sites.

Concurrent measurements can be useful for relating quantities that are less meaningful when measured and analyzed independently, where more useful information is formed from a comparison of different measurements taken at the same (or substantially the same) instant in time. Additionally or alternatively, concurrent measurements can be useful for situations where multiple simultaneous measurements are desired for consensus of an underlying measurement. By way of example, temperature readings from certain places on the skin may be influenced by environmental factors and it may be difficult or impossible to draw any useful insights from a single measurement. Thus, where a sensor metric includes temperature and multiple sensors are dispersed throughout a wearer's body, concurrent readings from multiple locations on the body can provide a consensus into the actual thermal state of the wearer's body.

Implementations may also or instead include obtaining and analyzing asynchronous measurements. "Asynchronous measurements" in this context will be understood to include measurements taken at different times with an unknown intervening interval. This may optionally be from two or more different locations. Thus, two or more physiological sensor measurements need not occur simultaneously in order to draw insights from an analysis or comparison thereof. For example, PPG signals gathered on a user's wrist during certain sleep periods and PPG signals obtained on the user's ankle during other, different sleep periods can be useful for analysis. Specifically, these PPG signals will likely produce significantly different waveforms, and a comparison of these waveforms can be used to predict or diagnose potential blood flow issues to the lower extremities. As another example, measurements taken generally at different times during the day (e.g., morning, noon, evening) or separated by a significant period of time such as days or weeks, may contain useful physiological information although the precise interval between sets of measurements is not known. Stated more generally, different temporal measurements (even across different days) may provide value for a user by comparing PPG waveform features or otherwise comparing and analyzing the data even where the interval between measurements is not known with precision, or is not known at all.

Implementations may also or instead include obtaining and analyzing bilateral measurements. It will be understood that "bilateral measurements" in this context shall include measurements taken to compare one side of a wearer's body to another, different side of a wearer's body, or more generally to compare one region of the body to another, different region. For example, because the human body is substantially symmetrical in most subjects, comparison of physiological signals obtained from opposing sides of the human body can provide useful insights. By way of example, the difference in amplitude of a PPG wave between a user's left and right sides may indicate asymmetries in blood flow between the two sides. It will be understood that bilateral measurements can be obtained and analyzed concurrently and/or asynchronously.

For one or more of the above measurements, useful comparisons of differential sensor data may require the sensors to be deployed in known locations. However, it is possible that data can be compared across a plurality of sensors and useful insights can be gathered therefrom even without knowing the specific locations of one or more of the sensors. By way of example, feedback to a user could simply indicate that a particular measurement is different from others; and a user, themselves knowing the location of that particular sensor, can infer something useful from that feedback.

It will be understood that additional timing infrastructure may be required to support synchronous or concurrent measurements. Where individual sensors are coupled by wires directly to a processing hub (such as any of the controllers or processors described herein) for storage and analysis, e.g., where the garment infrastructure includes a wired communications bus, transit times may generally be assumed to be instantaneous, and signals may be time stamped or otherwise associated with a global timing reference based on the time they are received at the processing hub. However, where signals from different modules are sent wirelessly and/or through some indirect communication channel to a central location for storage and processing, an additional timing reference may be required. In one aspect, individual modules may be synchronized, e.g., to a GPS timing reference or some other generally available global timing reference. In another aspect, the garment may issue a timing signal or a beacon for use by modules in time stamping sensed data. Thus, in one aspect, a module may include a receiver to receive timing data from a timing reference (e.g., in the garment infrastructure or available from some global timing source), and may be configured, e.g., by computer code, to synchronize a local clock based on the timing data and to time stamp measurements using the local clock as they are captured. In another aspect, the timing reference may be a continuous timing signal that is used to directly time-stamp concurrent measurements. More generally, any suitable technique for synchronizing modules to support concurrent and/or synchronous signal acquisition may be used in a garment infrastructure as contemplated herein.

Various sensor modalities that can be used in differential analyses according to the present teachings will now be described by way of example. However, it will be understood that different sensing hardware and techniques may also or instead be used.

In one aspect, the sensors may use PPG. PPG measurements from different sensors and locations in a smart garment or the like can yield insights with respect to blood pressure, heart health, circulatory system condition (e.g., blood vessel stiffness, blood viscosity, and so on), and the like. For example, comparing a PPG waveform taken from a location on the chest of a user to those taken on the wrist, ankle, head, or elsewhere, can provide insight into peripheral circulation.

The sensors may also or instead measure temperature, which may include skin temperature, body temperature, core temperature, and the like. Body temperature (e.g., temperature of the skin) can be influenced by environmental conditions and/or different activities. Temperature may also be regulated by blood flow, and, in this manner, differential temperature measurements may provide additional cues to circulation. Temperatures may also include an ambient or environmental temperature, which may affect strain experienced by a user during various activities, and may be used to adjust strain calculations accordingly, e.g., by increasing a calculated strain score as temperatures deviate from a typical room temperature range (e.g., of about 68-72 degrees Fahrenheit).

The sensors may also or instead measure muscle oxygen (SmO2). Muscle oxygen can vary widely between different muscles, and can be highly dependent on an activity in which a user is engaged. Thus, insights yielded from an analysis of differential measurements of muscle oxygen can be used to recognize activities of the user, or assist in automated activity recognition, or to calculate corresponding strain, recovery, and so forth. Muscle oxygen (SmO2) measurements can also or instead by applied to tissue, and be used to detect the oxygen level in other organs or parts of the body non-invasively. For example, tissue oxygen measurements of the breast may be used to detect the presence of cancer, and/or its response to an intervention such as chemotherapy over time based on the hypermetabolic state of a tumor versus healthy tissue and its corresponding difference in tissue oxygen saturation. Further, tissue oxygen measurements, when performed on the head, can indicate the oxygenation state of the brain.

In general, muscle oxygenation represents the balance in oxygen supply (via the cardiopulmonary system) and demand (by the muscle) and can therefore be an excellent indicator of muscular load. And, unlike heart rate, which is generally a systemic parameter used to indicate cardiovascular load, muscle oxygen levels can differ between muscles due in large part to the potentially different levels of exertion by each of these different muscles during different activities. As such, the differential analysis techniques described herein when applied to muscle oxygen measurements can provide an advantageous picture of the state of muscular load of the wearer.

Other factors that may contribute to differences in muscle oxygen measurements can be from the supply-side, for example inhibited blood flow to certain muscle or other tissue. This can be caused by a natural regulation by the body, or by some other condition or illness (e.g., peripheral arterial disease), or due to an operation or the like.

Regardless, muscle oxygen measurements when considered in the context of training and differential analysis may provide useful cues to a user that they can act on.

For example, the body's natural regulation of blood flow relates to warmup, and can be well quantified by differential analysis techniques. Light activity during warmup can induce increased blood flow to certain muscles, indicating a state of readiness, while other muscles may not experience the same level of increased blood flow during the same time. This feedback can be used to adjust the activity the user is engaged in so as to promote blood flow to all desired muscles and ensure they reach a desired state of readiness. Failure to do so can put the user in a state where they are more prone to injuries when improperly prepared.

Muscle oxygen measurements can also indicate a state of muscular fatigue, which may also be an indication that the wearer is in a state where injuries are more likely to occur. This may also be another indication as to which muscles are limiting athletic performance, therefore prompting a user to train to improve these deficiencies. Additionally, a user may alter their form so as to better engage muscles that are less fatigued and give a rest to those which are more fatigued.

The above examples are similarly applicable to the case of "asynchronous" measurements. One day to the next, a user may engage in activity at different levels of exertion, which can be quantified via muscle oxygen measurements. These measurements can track an overall training intensity during subsequent training sessions and also measure physiological changes over time. For example, a runner who consistently runs a roughly fixed distance in a fixed amount of time, but continually does so at increased oxygen levels, can indicate improving of the oxygen delivery to the muscles. Similarly, muscle oxygen measurements can be used to track the body's response to hypoxic conditions (e.g., high altitude) over time.

Generally, a relatively high level of oxygen supply to the muscle is beneficial for a user, as mentioned in the examples above. However, a user's body should also be able to use the supplied oxygen effectively. To this end, extensions of the examples above may also or instead include cases where it is desirable to sufficiently desaturate oxygen in the muscle. For example, if a user is engaged in maximal effort activity and unable to desaturate, it can indicate poor oxygen uptake by the muscle, thus indicating a deficiency which can be targeted via training. More generally, muscle usage and fatigue can be measured using an array of sensors in one or more smart garments, and this data can be used to improve physiological monitoring by supporting activity recognition, improving measurements of strain and recovery, and providing coaching suggestions and analysis related to prior workouts and potential future workouts.

The sensors may also or instead include pulse oximetry oxygen saturation (SpO2) sensors. The analyses of differential measurements of pulsatile oxygen may be similar to those possible with PPG measurements, but with additional information related to oxygen delivery.

It will be understood that sensors used to obtain differential measurements may include optical sensors. For example, optical sensors can be used to capture data related to PPG, SpO2, and SmO2—where each of these metrics may conveniently use similar wavelength ranges of light. The sensors may also or instead include other sensors, which may be optical or non-optical. By way of example, the sensors used to obtain differential measurements may include inertial sensors, electrical sensors (e.g., EKG, EMG, EEG, and the like), and so on.

Also or instead, in the context of smart garments, sensors used to obtain differential measurements may include resistive fabrics used to form at least a portion of a smart garment. Resistive fabrics such as piezo-resistive fabric sensors, conductive fabric threads, and the like have been used to detect respiration, and may usefully be incorporated into a smart garment as described herein.

Differential analyses according to the present teachings can include an analysis of the same type of signal (e.g., the same metric) in different locations and/or at different times. Also or instead, differential analyses according to the present teachings can include an analysis of a different signal in different locations and/or at different times. By way of example, PPG data from a wearer's wrist analyzed in conjunction with inertial measurements on a wearer's foot can be used to evaluate a wearer's activity along with accompanying metrics such as strain. Various examples of use cases will now be described.

Example 1: Asynchronous Measurements of PPG for Insights Regarding Cardiovascular Health A combination of asynchronous measurements specific to PPG signals can provide insights into cardiovascular health based on multiple measurements from multiple locations. By way of example, using a differential analysis, the shape of the PPG signal at different locations can be used to infer properties such as arterial stiffness and cardiovascular health, which can in turn be used to produce a parameter such as a "cardiovascular age" or the like, which may be useful to a user, trainer, coach, health care professional, or the like. That is, certain parameters that govern cardiovascular health may vary slowly over time (e.g., on the time scale of years, as a human ages). These parameters may include, for example, arterial stiffness, arterial diameter, and arterial wall thickness. Other slowly-varying quantities such as body weight also influence these vascular parameters. Given that these parameters vary over a timescale of months and years, taking measurements from different locations one day to the next can be assumed to be fixed for certain analyses. Thus, PPG signals from multiple locations, even when not captured synchronously, can yield insight into the aforementioned cardiovascular parameters more so than measurement(s) from a single location. That is for properties that vary slowly over long time scales, differential analysis may usefully be performed without concurrent measurements, and a single sensor may advantageously be employed to capture multiple measurements at multiple locations, after which a differential pulse shape analysis or the like may be employed to draw inferences about cardiac health as describe above.

One example involves measuring the magnitude of PPG signals at different locations. By way of example, such measurements can provide the potential to diagnose postoperative or other issues with the circulatory system, where adequate blood supply may not be reaching certain parts of the body.

This example can also apply to the bilateral class of measurements described above. That is, the location of a sensor on a wearer's body (e.g., which can be determined from its location/presence in a garment, or otherwise) can provide a relatively straightforward path to determine differences in measurements. For example, if a sensor is located in a strap that is alternated periodically between a user's left and right wrist, the pulse shape at each of these locations can be characterized and compared. And simply identifying that the representative pulse shape between the left and right wrist is different can have value in a physiological health analysis. Using the techniques described herein, a wrist-worn or garment-worn monitor (or some combination of these) may be analyzed based on accelerometer data to determine when a sensor is on the left wrist and when the sensor is on the right wrist (or at any other locations suitable for bilateral analysis). Pulses captured at each of these locations without some useful time window (e.g., within a few days) may then be compared to identify differences between a left-side pulse shape and a right-side pulse shape.

Example 2: Synchronous Measurements of PPG and Transit Time for Insights Regarding Blood Pressure In one aspect, two or more PPG sensors can concurrently acquire data along the same branch of an arterial tree of a wearer. The pulse wave propagation along the branch can be quantified, yielding a transit time of the arterial pulse between the two locations, which in turn permits an inference about blood pressure. A variety of techniques for non-invasive, cuffless blood pressure monitoring are known in the art based on, e.g., empirical models, wavefront models, physical models (e.g., of arterial wall elasticity) and the like, with blood pressure generally inversely related to pulse transit time. Thus, in one aspect, there is disclosed herein a smart garment with two modules that capture PPG data at two locations along an arterial path and use this data to determine blood pressure based on transit time. In another aspect, this concept may be applied to different points along different arterial branches, e.g., where the relative distance of each to a source (i.e., the heart) is known. Similarly, synchronous EKG and PPG signals may provide useful pulse wave propagation information.

Practical considerations of synchronizing time across two (or more) devices to accurately determine transit time are known in the art—see, e.g., IEEE 1588-2002 describing the precision time protocol (PTP), which is incorporated by reference herein. Other techniques may also or instead be used, including beacons, time stamps, global timing references, and the like. It is thus possible to accurately determine blood pressure (and any other relevant physiological parameters) from transit time and other features resolved from synchronous PPG measurements, and to determine additional parameters (e.g., blood flow) from these features.

Example 3: Synchronous/Asynchronous Muscle Oxygen Measurements for Insights Regarding Muscular Exertion Muscle/tissue oxygen measurements may be more spatially dependent than other parameters like heart rate and/or blood pressure measurements. In this context, differential measurements may provide information regarding which muscles are limiting performance during an activity based on their state of oxygenation, and/or bilateral differences. Further, in the context of training, differential oxygen measurements can inform a user whether to target certain muscles over others, and/or whether to correct their form or otherwise change their activity. Moreover, differential oxygen measurements can be used to understand or diagnose one or more conditions such as poor circulation, peripheral arterial disease, diagnosing postoperative circulatory issues, and the like. By way of example, asynchronous muscle oxygen measurements in a user's legs shortly after receiving an angioplasty and coronary artery stent can reveal low oxygenation in one leg versus the other, thereby indicating poor circulation as a basis for prescribing additional diagnostics and intervention.

Smart Garments as Infrastructure for a Physiological Sensing System

As described above, embedding sensors and other wearable technologies in clothing can provide many advantages. For example, embedding wearable technology in a shirt may allow electrocardiogram (ECG) based heart rate measurements to be gathered more easily from the torso, wireless antennas to be placed above the upper portion of the thoracic spine to achieve better communications signal, a contactless payment system be embedded in a sleeve cuff for easy interactions with a payment terminal, and muscle oxygen saturation measurements to be gathered from muscles such as the pectoralis major, latissimus dorsi, biceps brachii, and other major muscle groups. Smart garments can similarly free up valuable real estate to accommodate other device or fashion accessories. For example, if sensors in a wrist-worn device that provide heart rate monitoring and step counting can be instead embedded in a user's undergarments, the user may still receive the biometric information they desire, while also being able to wear jewelry or other accessories on their wrist. Smart garments can also add technology to items that a user already wears, more seamlessly fitting into their habits and lifestyle, while removing the burden of having to wear additional items. However, a smart garment can do more than simply facilitate an alternative way to couple a sensor module to a wearer—it may offer other benefits made possible by the garment itself. Some nonlimiting examples are discussed below.

Utilizing a Separate Computing Device (e.g., a Smartphone)

A smart garment system may use capabilities or features of a separate computing device such as the mobile phone of a user. For example, a smart garment system may be able to detect the presence of a user's computing device and determine other information such as its location and orientation relative to a smart garment. This information can then be used to determine an activity of the user, determine a geographic location of the user (e.g., based on the computing devices geolocation capabilities), and so on. Also or instead, a smart garment system may use capabilities of the computing device such as communications and processing capabilities to offload physiological monitoring tasks.

Embedded Antenna

A smart garment system may include an antenna, e.g., on one or more sensing modules, on a control module, and/or as part of a garment itself. By way of example, a conductive antenna (passive trace) may be affixed to, or embedded within, a garment, so that the wireless communication range of a sensor module can be extended when it is placed in the garment.

System Hub

A smart garment may provide a functional hub for any attached devices. This may couple to or contain accessories such as power, user input/output, processing resources, networking resources, inter-device communications infrastructure, and so forth. The hub may also or instead serve as a wireless resource to wirelessly gather data from various sensors coupled to the smart garment, and to store the resulting sensor data and/or forward (e.g., opportunistically when a suitable receiving device is available) to a remote processing resource. This latter approach can advantageously reduce local data storage and communications requirements for sensing modules to permit smaller and/or more power efficient modules.

User Inputs/Feedback

In addition to measurements taken by one or more sensors within a smart garment, a smart garment system can provide a user interface including input or output for images/video, sound, vibration, and so forth. The user interface may include alternatives to a graphical user interface more suited to a garment. For example, a smart garment (e.g., a sensor module of a smart garment) may include a capacitive sensor, a force sensor pad, or the like, which can be structurally configured to allow a user to provide an input thereto—for example, to indicate when the wearer has run a lap on a track, to annotate various moments during exercise, to adjust a strain coach, to switch a sensor on or off, and so on.

In a similar manner, a smart garment or a module of a smart garment may include mechanisms for providing feedback to a user. This can include one or more of a visual indicator such as a light, a tactile indicator such as a vibration motor, an audio indicator such as a speaker (this can be especially advantageous if included in headwear), and so on. For example, such mechanisms for providing feedback to a user may help guide a user through breathing exercises as part of a meditation session, indicate expiration of a time interval, signal achievement of milestones, and so forth.

Powerpack

A smart garment or portion thereof may include a power source. For example, a centralized/discrete power pack module in a smart garment may provide a source of power to recharge various sensor modules. This power pack may include, or be powered or recharged by, a user's mobile phone, from which energy can be extracted wirelessly via reverse charging. In another aspect, one of the modules may include a battery pack or the like for powering or recharging other modules coupled to the smart garment.

Arrangement and Motion Detection

A smart garment or portion thereof may include one or more mechanisms for ascertaining a fit or arrangement of the smart garment or portion thereof. For example, a sensor module may be configured to detect a force or pressure (e.g., via a capacitive touch sensor or the like) in order to determine whether a garment is properly situated on a user (e.g., whether the fit is proper, too tight, or not tight enough). Motion detection may also be provided, e.g., where feedback can be used to guide a user through a desired motion when exercising or the like. Thus, in one aspect, a number of accelerometers may be integrated into a garment at useful locations (wrists, ankles, shoulders, etc.) and coupled wirelessly or through a wired communication bus in the garment to other system components. These motion sensors may be independently powered or powered by another module or power source for the smart garment, and may provide motion data to other resources within a smart garment infrastructure for use in activity detection and other physiological monitoring and the like.

Wearability Enhancements for Smart Garments

One or more of the modules as described herein (e.g., sensing or control modules) may be specifically tailored for wearability on a smart garment, e.g., throughout the body. By way of example, one or more modules may omit a graphical user interface, e.g., where the modules might be positioned in locations where such an interface would be impractical or undesirous—e.g., on an ankle or foot, on undergarments, and so on. Such modules may usefully present a programming interface that presents a human or computer useable interface to other devices in order to integrate such modules into a physiological monitoring system using the smart garment.

One or more of the modules may include inputs that are specifically designed for use in a smart garment system. For example, the inputs may be structurally configured to be accessed via a "tap detection" feature or a piezo-electric touch or tap sensitive surface. In this manner, a user can provide inputs to a device even in the absence of a graphical or mechanical user interface, and in particular, when a device is at a marginally accessible location such as under other layers of clothing. This can be a distinct advantage over other inputs such as buttons, a crown, a touchscreen, capacitive touch, and the like. Further, inputs that utilize such a tap detection technique can also help prevent false inputs to do inadvertent button presses and the like, although a multi-tap interface protocol may be used when appropriate to avoid interpretation of spurious contact as user input.

The above systems, devices, methods, processes, and the like may be realized in hardware, software, or any combination of these suitable for the control, data acquisition, and data processing described herein. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method described above, and combinations thereof may be embodied in computer executable code that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. The code may be stored in a non-transitory fashion in a computer memory, which may be a memory from which the program executes (such as random access memory associated with a processor), or a storage device such as a disk drive, flash memory or any other optical, electromagnetic, magnetic, infrared, or other device or combination of devices. In another aspect, any of the systems and methods described above may be embodied in any suitable transmission or propagation medium carrying computer-executable code and/or any inputs or outputs from same. In another aspect, means for performing the steps associated with the processes described above may include any of the hardware and/or software described above. All such permutations and combinations are intended to fall within the scope of the present disclosure.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y, and Z may include any method of directing or controlling any combination of such other individuals or resources to perform steps X, Y, and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity and need not be located within a particular jurisdiction.

It will be appreciated that the methods and systems described above are set forth by way of example and not of limitation. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims.

What is claimed is:

1. An adjustable band comprising:
   a monitoring device comprising a housing for a battery and physiological sensing circuitry powered by the battery;
   a clasp, wherein:
      the clasp includes a first end rotatably mounted to the monitoring device about a rotation axis,
      the clasp includes a second end opposing the first end, the second end including a cross member having an axis parallel to the rotation axis for the clasp,
      the clasp includes a pair of arms extending from the first end of the clasp to the second end of the clasp, and
      the clasp is rotatable about the rotation axis between a closed position overlapping the monitoring device and an open position extending away from the monitoring device;
   a band of an elastic material, the band having a first end and a second end;
   a hook affixed to the first end of the band, the hook rotatably coupled to the cross member on the second end of the clasp, and rotatable around the rotation axis to decouple the hook from the cross member; and
   a buckle coupled to the second end of the band, wherein;
      the buckle forms a c-shaped cross section along an axis transverse to the band and parallel to the rotation axis of the clasp, the c-shaped cross section including a pair of flanges shaped and sized to engage with a corresponding pair of indents in the monitoring device under a circumferential tension on the band,
      the buckle linearly removable from and replaceable to an end of the monitoring device along the axis transverse to the band,
      the buckle includes a fixture providing an overlapping path for adjustably securing the band in the buckle to retain a length of the band of the elastic material between the hook and the buckle under the circumferential tension on the band, the length of the band between the hook and the buckle is adjustable by a user and retained by the overlapping path of the buckle to secure the physiological sensing circuitry of the monitoring device in a position for physiological monitoring while accommodating diameter changes resulting from user movement, and the pair of arms of the clasp, when in the closed position, overlap the c-shaped cross section of the buckle to secure the buckle against displacement along the axis transverse to the band, whereby the buckle retains the length of the band for the user when the buckle is removed from and replaced to the monitoring device.

2. The adjustable band of claim 1, wherein the band of the elastic material includes a high friction material on a surface contacting the monitoring device when the clasp is in the closed position.

3. The adjustable band of claim 1, wherein the circumferential tension along the band of the elastic material secures the hook in a rotational orientation that prevents decoupling of the hook from the cross member of the clasp when the clasp is in the closed position.

4. The adjustable band of claim 1, wherein the band of the elastic material includes an elastic woven material.

5. The adjustable band of claim 1, wherein the hook includes a crimp permitting the hook to fold with a low profile and lie flush with the band.

6. The adjustable band of claim 1, wherein the fixture includes two adjacent slits along the overlapping path.

7. The adjustable band of claim 1, wherein the pair of arms of the clasp overlap a pair of opposing ends of the buckle along the axis transverse to the band when in the closed position.

8. The adjustable band of claim 1, wherein the pair of arms of the clasp rotate away from the end of the monitoring device when in the open position.

9. The adjustable band of claim 1, wherein the housing encloses the battery and the physiological sensing circuitry in a waterproof enclosure that prevents ingress of water during immersion in water to at least one meter for at least thirty minutes.

10. The adjustable band of claim 1, wherein the monitoring device includes a spring bar with protruding surfaces to retain the clasp in the open position.

11. The adjustable band of claim 10, wherein the clasp includes an indent to engage the protruding surfaces of the spring bar to retain the clasp in the open position.

12. The adjustable band of claim 1, wherein the buckle is sized to couple to a partially cylindrical surface of the monitoring device.

13. The adjustable band of claim 1, wherein the monitoring device is configured to monitor physiological data.

14. The adjustable band of claim 1, wherein the clasp is rotatable around the rotation axis over an angle of at least 180 degrees.

15. The adjustable band of claim 1, wherein the fixture may be collapsed to lie unobtrusively against the buckle.

16. The adjustable band of claim 1, wherein the fixture is a rigid structure extending from the buckle.

17. The adjustable band of claim 1, wherein the monitoring device includes a wireless battery removably and replaceably coupled to the monitoring device.

18. The adjustable band of claim 17, wherein the wireless battery is coupled to the monitoring device such that the wireless battery is retained in a precise location relative to a corresponding wireless power interface of the monitoring device.

19. The adjustable band of claim 17, wherein a housing of the wireless battery encloses the wireless battery and sensing circuitry in a waterproof enclosure that prevents ingress of water during immersion in water to at least one meter for at least thirty minutes.

20. The adjustable band of claim 17, wherein the wireless battery includes a pair of wings that are symmetrical about an axis normal to a path that the wireless battery follows when engaging with the monitoring device to attach to or detach from the monitoring device.

* * * * *